(12) United States Patent
Ikeda et al.

(10) Patent No.: US 7,494,721 B2
(45) Date of Patent: Feb. 24, 2009

(54) LIGHT-EMITTING DEVICE, CONDENSED POLYCYCLIC COMPOUND USED THEREIN AND METHOD FOR PRODUCING SAME

(75) Inventors: Masaaki Ikeda, Kita-ku (JP); Takaaki Kurata, Kita-ku (JP); Teppei Tsuchida, Kita-ku (JP); Chihaya Adachi, Chitose (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 97 days.

(21) Appl. No.: 10/542,085

(22) PCT Filed: Jan. 16, 2004

(86) PCT No.: PCT/JP2004/000306

§ 371 (c)(1),
(2), (4) Date: Jul. 13, 2005

(87) PCT Pub. No.: WO2004/065520

PCT Pub. Date: Aug. 5, 2004

(65) Prior Publication Data

US 2006/0051612 A1    Mar. 9, 2006

(30) Foreign Application Priority Data

| Jan. 17, 2003 | (JP) | ............... 2003-009304 |
| Jun. 11, 2003 | (JP) | ............... 2003-166799 |
| Jun. 18, 2003 | (JP) | ............... 2003-172896 |
| Jun. 26, 2003 | (JP) | ............... 2003-181925 |
| Aug. 28, 2003 | (JP) | ............... 2003-305338 |
| Nov. 12, 2003 | (JP) | ............... 2003-382625 |

(51) Int. Cl.
*H05B 33/14* (2006.01)
*C09K 11/06* (2006.01)
*C07D 493/02* (2006.01)
*C07D 495/02* (2006.01)

(52) U.S. Cl. .................. 428/690; 428/917; 313/504; 313/506; 257/40; 257/102; 257/103; 549/24; 549/381

(58) Field of Classification Search ............... 428/690, 428/917; 313/504, 506; 257/102, 103, E51, 257/40; 549/381, 24
See application file for complete search history.

(56) References Cited

U.S. PATENT DOCUMENTS 6,995,893 B2 * 2/2006 Kobayashi ............ 359/272

FOREIGN PATENT DOCUMENTS

| EP | 0 629 512 | 12/1994 |
| JP | 5-222362  | 8/1993  |

OTHER PUBLICATIONS

Sumio Tokita et al, "Benzo [1,23-kl:4,5,6-k'l']Dixanthene no Hitaishogata Ruijitai Oyobi Sono Endoperoxide no Gosei to Sorera no Photochromic Tokusei", Journal of the Chemical Society of Japan, 1992, No. 10, pp. 1097-1101.

(Continued)

*Primary Examiner*—D. L Tarazano
*Assistant Examiner*—Camie S Thompson
(74) *Attorney, Agent, or Firm*—Nields & Lemack

(57) ABSTRACT

The device according to the invention is a device having organic thin films containing a light-emitting layer between an anode and a cathode that emits light by application of electric energy, characterized in that the light-emitting device contains at least a compound having the basic skeleton represented by the following General Formula (1) or (2). Use of the condensed polycyclic compound according to the invention allows production of high-brightness, high-efficiency light-emitting device superior in color purity.

18 Claims, 1 Drawing Sheet

OTHER PUBLICATIONS

Sumio Tokita et al., "[1,2,3-kl:4,5,6-k'1']Dixanthene no Zokangata Ruien Kogobutsu Narabi ni Sorera no Endoperoxide no Gosei to Sorera no Photochromic Tokusei", Journal of the Chemical Society of Japan, 1989, No. 5, pp 876 to 879.

Sumio Tokita et al., "Benzo [1,2,3-kl:4,5,6-k'1']Dixanthene no Methyl Yodotai Oyobi Sono Endoperoxide no Gosei to Sorera no Photochromic Tokusei", Journal of the Chemical Society of Japan, 1988, No. 5, pp. 814 to 818.

T.Watanabe et al., "Photochromic Properties of Benzodixanthese Analogues Having Alkyl Group and Their Langmuir-Blodgett Films", J.Photoholymer Sci. and Technol, 1998, vol. 11, No. 1, pp. 41 to 46.

S. Tokita et al., "Molecular Design and Synthesis of Novel Analogues of Benzodixanthene and Anthradichromene", Mol.Cryst.Liq.Cryst., 1997, vol. 297, pp. 269-276.

J.B. Christensen et al., "Corbienes and Dioxapyrenes- New Weitz-Type Donors" Synthetic Metals, 1991, vol. 42, No. 3, pp. 2311-2313.

* cited by examiner

LIGHT-EMITTING DEVICE, CONDENSED POLYCYCLIC COMPOUND USED THEREIN AND METHOD FOR PRODUCING SAME

TECHNICAL FIELD

The invention relates to a light-emitting device having a thin film of organic compound that emits light by application of electricity, a condensed polycyclic compound for use therein, and the production method thereof. The light-emitting devices are usable in various fields including display device, flat panel display, backlight, illumination, interior goods, sign and mark, signboard, electrophotographic camera, optical signal generator, and the like.

BACKGROUND ART

Development of and studies on organic electronic parts using organic materials, have been conducted eagerly recently. Examples of such parts include organic electronic devices such as organic transistor, organic semiconductor laser, organic solar battery, and organic EL device. In particular, organic EL (electroluminescent) devices, promising high-quality display devices, are on the verge of commercialization. The organic EL devices, which are particularly lower in electric consumption and have various advantageous characteristics such as ultra-thin film, high-brightness light emission, and high visibility due to high self-luminescence, have been studied and developed intensively as next-generation display, planar light source, light-emitting device, and the like.

In typical configurations, the organic EL device using organic materials have a two-layer structure (single hetero structure) having an organic fluorescent material thin film (light-emitting layer) and a positive hole-transporting layer that are laminated to each other between a cathodic metal electrode and an anodic transparent electrode, a three-layer structure (double hetero structure) having an electron-transporting layer, a light-emitting layer, and a positive hole-transporting layer that are laminated to each other between a metal electrode and a transparent electrode, and the like. The positive hole-transporting layer has the functions of receiving positive holes from the anode, transporting the positive holes, and blocking electrons, while the electron-transporting layer has the functions of receiving electrons from the cathode and transporting the electrons. In addition, organic EL devices having a multilayer structure containing a positive hole-injecting layer, an electron-injecting layer or a positive hole-blocking layer, or the like additionally as needed were also developed. Each of these organic EL devices has its own unique structure functionally specialized from those of the organic EL devices having the two- or three-layer structure, for example, a structure functionally strengthened to receive positive holes or electrons or blocking leak electrons or positive holes, or allowing high brightness by more efficient recombination of electron and positive hole, improvement in durability, elongation of lifetime, or reduction in electric consumption by reduction of applied voltage.

In such light-emitting devices having organic thin films, a substrate of glass, plastic or a suitable material is placed outside the transparent electrode. Recombination of the electrons injected from a metal electrode and the positive holes injected from a transparent electrode, for example, of indium tin oxide (ITO) in the organic material thin film between the two electrodes generates excitons, which emit light in the process of emission inactivation, and the light is emitted outward via the transparent electrode and the glass substrate.

Characteristically, these devices are thinner in shape and allow, for example, high-brightness light emission at a lower drive voltage, and multi-color light emission by proper choice of the light-emitting material.

In representative configuration of the organic laminated thin film light-emitting device proposed by a research group in Eastman Kodak Company, a positive hole-transporting layer of diamine compound, light-emitting and also electron-transporting layers of tris(8-quinolinolato)aluminum complex, and a cathode of Mg:Ag (alloy) are formed in that order on an ITO glass substrate.

For producing for full-color displays, devices having blue, green, and red light-emitting devices coated on a substrate separately are now studied. Among the light-emitting devices, the green light-emitting material, which is formed by vapor deposition of a low-molecular weight compound, is higher in maturity and closer to commercialization, at a level superior in practicality such as brightness and durability. However, the red and blue light-emitting materials are left delayed in development, and in particular in red light-emitting materials, there is a problem that there are no such light-emitting materials that are superior in durability and show sufficient brightness and color purity. An orange device relatively higher in efficiency was prepared for production of a multi-colored display, but currently, the efficiency is still insufficient and the material expensive. Because of the problem of device deterioration, devices emitting white light have also been studied intensively. Even with these white light-emitting materials, there is also the problem that there are no materials that are superior in durability and show sufficient brightness and sufficient color purity.

Examples of the red light-emitting materials include perylenes such as bis(diisopropylphenyl)perylene, porphyrins, europium complexes, julolidine-substituted styryl compounds (e.g., Japanese Patent Application Laid-Open (JP-A) No. 2001-43974), and the like. The emission color (emission wavelength) is adjusted to a desired color used by doping method, i.e., by adding a trace amount of red fluorescence compound into the host material as a dopant. Examples of the host materials include metal complexes of quinolinol derivatives such as tris(8-quinolinolato)aluminum complex, bis(10-benzoquinolinolato)beryllium complexes, diarylbutadiene derivatives, stilbene derivatives, benzoxazole derivatives, benzothiazole derivatives, perynone derivatives, and the like. Examples of the dopants include red fluorescence compounds such as 4-(dicyanomethylene)-2-methyl-6-(p-dimethylaminostyryl)-4H-pyran (DCM), metalphthalocyanine compounds (MgPc, AlPcCl, etc.), squarylium compounds, coumarin compounds (see e.g., JP-A No. 10-060427), violanthrone compounds, nailered, 5-cyanopyrromethene-$BF_4$ complexes (see e.g., JP-A No. 11-176572); and red emission light is obtained by doping the host material with the compound.

However, among those light-emitting materials (host and dopant materials) commonly used in the art, there are many light-emitting materials that have inferior luminous efficiency prohibiting high brightness, have poor color purity and a pale orange emission light only even when doped, or have low durability and a shortened lifetime of the device; thus, there exists a serious problem that there is no material satisfying the requirements in color purity and brightness at the same time. In addition, the orange light-emitting devices are still unsatisfactory in efficiency. Further, there is currently no white device for use as backlight or others that are higher in brightness and in luminous efficiency, longer in lifetime, and favorable in color purity.

In such a light-emitting device, a transparent electrode formed on a glass or polymer substrate is generally used as an anode; and a positive hole-injecting layer, a positive hole-transporting layer, and others are normally formed thereon. These transparent electrodes for example of ITO generally have a work function significantly different from that of the positive hole-transporting layer, and are different in energy level from the positive hole-transporting layer and adhesion between the ITO layer and the positive hole-transporting layer is poorer, which occasionally lead to crystallization of the positive hole-transporting layer and decrease in efficiency due to higher applied voltage, consequently causing instability during operation. Although a method of forming the transparent electrode, for example, of ITO lastly, similarly to the top emission structure, was studied recently, there was still the problem of similar deterioration in efficiency.

Examples of the materials for the positive hole-injecting layer include the phthalocyanine derivatives described in JP-A Nos. 57-51781, 63-295695 and 8-199161; the low-molecular weight compounds such as thiophene derivatives (see JP-A No. 5-94877), aromatic amine derivatives (see JP-A No. 8-269445), hydrazone derivatives (see JP-A No. 4-320483); and polymers such as polythiophene, polyaniline, polythienylene vinylene, and polyphenylene vinylene (see JP-A No. 4-145192); and the like.

However, there are still problems at long-term operational stability, lifetime, luminescence brightness, luminous efficiency, and others. To overcome these problems, it is quite important to develop an inexpensive material having sufficiently high optical and mechanical properties that is favorable in coating properties and suitable for mass production. In particular, devices containing a phthalocyanine derivative as a positive hole-injecting material have been widely used because they are relatively better, but the injection efficiency is still unsatisfactory and the luminous efficiency of the devices remains to be improved. In addition, the phthalocyanine derivative, which is used as a blue pigment, often caused the problem that absorbing a red emission light, changed the emission color and decreased the luminous efficiency. Use of other low-molecular weight positive hole-injecting materials also often carried the problem that the devices are inferior in stability and heat resistance because of their low glass transition and melting points, while use of polymer positive hole-injecting materials often carried the problem that it was difficult to form a uniform film by wet casting and the lifetime of the device was shorter. Phosphorescence devices particularly superior in internal quantum efficiency are attracting attentions recently, and for improvement of the efficiency thereof, it is necessary to develop a stable material for positive hole-injecting layers.

The condensed polycyclic compounds described in the invention (see e.g., E. Clar, W. Kelly, D. G. Stewart, J. W. Wright, J. Chem. Soc., (1956), 2652; Tokita, Arai, Ohoka, Nishi, Nippon Kagakukaishi JP, 1989, (5), 876; J. Photopolym. Sci. Technol., 11, 41 (1998); Tokita, Arai, Toya, Nishi, Nippon Kagakukaishi JP, 1988, (5), 814; Tokita, Suga, Toya, Nishi, Nippon Kagakukaishi JP, 1988, (1), 97; Mol. Cryst. Liq. Cryst., 1994, Vol. 246, 119; R. Schmidt, W. Drews, H.-D. Brauer, Journal of Photochemistry, 18 (1982), 365; Daisuke Goma, Masao Ken, Sumio Tokita, Journal of Photopolymer Science and Technology, 14, 2(2001), 239] have been studied in detail as a photochromic material that changes its color by irradiation of a particular light or by application of heat, but there is almost no report on application thereof to organic electronic parts, and the kinds of the derivatives investigated are limited; and thus, there exist an urgent need for a new material.

In addition, for production of a compound having the basic skeleton represented by Formula (1) or (2) described below by conducting ring closure of a compound having the basic skeleton represented by Formula (8) or (9) described below, a method of melting and ring-closing a compound in anhydrous aluminum chloride and sodium chloride (for example, E. Clar, W. Kelly, D. G. Stewart, J. W. Wright, J. Chem. Soc., (1956), 2652); a method of melting and ring-closing a compound in anhydrous aluminum chloride, sodium chloride, and hydroquinone (e.g., JP-A No. 6-56777 and Tokita, Arai, Toya, Nishi, Nippon Kagakukaishi JP, 1988, (5), 814; R. Schmidt, W. Drews, H.-D. Brauer Journal of Photochemistry, 18 (1982), 365; and Daisuke Goma, Masao Ken, Sumio Tokita journal of Photopolymer Science and Technology, 14, 2(2001), 239), and other have been reported. However, all of these methods were not proper as a commercial method, as the ring closure reactions are inferior in workability because they are carried out in the absence of solvent and the methods give chloride salts of Formula (1) or (2) as byproducts.

DISCLOSURE OF THE INVENTION

The inventors have found that it was possible to overcome the problems above mentioned by using a particular condensed polycyclic compound as the material for light-emitting devices, in particular as the light-emitting material, and completed the invention.

Accordingly, the invention provides a light-emitting material (host and doping materials) for a light-emitting device higher in luminous efficiency that emits an orange to red light and a white light-emitting devices, and a light-emitting device emitting a high-brightness and high-color purity light; and the light-emitting device according to the invention operates at low voltage and has a high luminous efficiency as well as practical stability and lifetime. In addition, the new condensed polycyclic compound provided by the invention is useful as an organic electronic material and, in particular, as an organic EL material.

More specifically, the invention provides:

1. A light-emitting device emitting light by electric energy having one or more layers of organic thin films formed between an anode and a cathode, characterized in that the organic thin film contains a compound having the basic skeleton represented by the following General Formula (1) or (2):

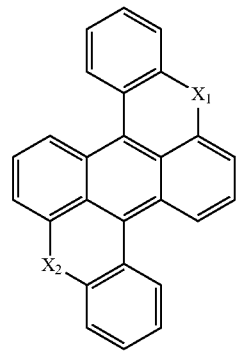

(1)

-continued (2)

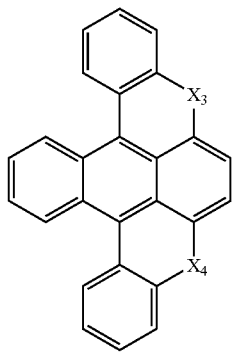

(wherein, $X_1$, $X_2$, $X_3$ and $X_4$ each independently represent an oxygen, sulfur, selenium, or tellurium atom, or $NR_{29}$; and $R_{29}$ represents a hydrogen atom, an aliphatic hydrocarbon residue which may be substituted, or an aromatic residue which may be substituted.);

2. The light-emitting device described in 1 above mentioned, wherein the compound having a basic skeleton represented by Formula (1) or (2) is a compound represented by the following General Formula (3) or (4):

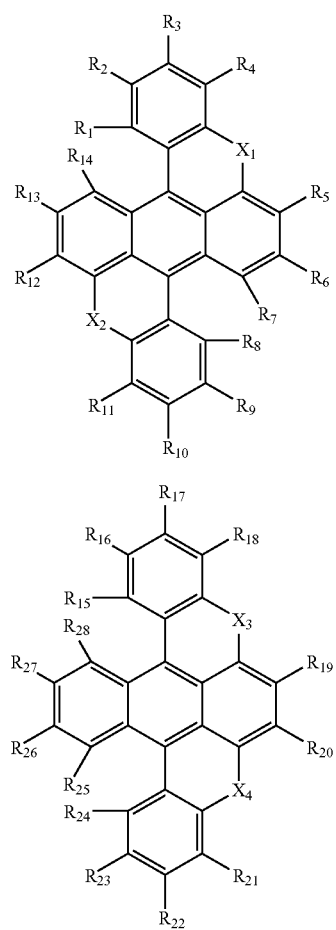

(wherein, $X_1$, $X_2$, $X_3$ and $X_4$ each are the same as those in Formulae (1) and (2); $R_1$ to $R_{28}$ each independently represent a hydrogen atom or a substituent group; and the neighboring groups among the substituent groups represented by $R_1$ to $R_{14}$ and $R_{29}$ in Formula (3) and $R_{15}$ to $R_{29}$ in Formula (4) may bind to each other forming a ring(s) which may be substituted.);

3. The light-emitting device described in 2 above mentioned, wherein $X_1$, $X_2$, $X_3$ and $X_4$ in Formula (3) or (4) each represent an oxygen or sulfur atom;

4. The light-emitting device described in 2 or 3 above mentioned, wherein the neighboring groups among $R_1$ to $R_4$, $R_8$ to $R_{11}$, $R_{15}$ to $R_{18}$, and $R_{21}$ to $R_{24}$ in Formula (3) or (4) bind to each other, forming a ring(s) which may be substituted;

5. The light-emitting device described in any one of 2 to 4 above mentioned, wherein $R_1$ and $R_2$ and/or $R_3$ and $R_4$ and/or $R_8$ and $R_9$ and/or $R_{10}$ and $R_{11}$, and/or $R_{15}$ and $R_{16}$ and/or $R_{17}$ and $R_{18}$ and/or $R_{21}$ and $R_{22}$ and/or $R_{23}$ and $R_{24}$ in Formula (3) or (4) bind to each other, forming an aromatic ring(s) which may be substituted;

6. The light-emitting device described in any one of 2 to 5 above mentioned, wherein the substituent groups represented by $R_1$ to $R_{29}$ in Formula (3) or (4) each are a substituted or unsubstituted aliphatic hydrocarbon residue or a substituted or unsubstituted aromatic residue;

7. The light-emitting device described in any one of 2 to 6 above mentioned, wherein the substituent groups represented by $R_1$ to $R_{29}$ in Formulae (3) and (4) each are a halogen atom, an aromatic residue having a halogen atom, or an aliphatic hydrocarbon residue having a halogen atom;

8. The light-emitting device described in 7 above mentioned, wherein the halogen atom is a bromine or fluorine atom;

9. The light-emitting device described in any one of 2 to 8 above mentioned, wherein $X_1$ and $X_2$ in the compound represented by Formula (3) each independently represent an oxygen or sulfur atom; $R_1$ represents H, F, $CH_3$, Ph, or $CF_3$; $R_2$ represents H, $CH_3$, $C_2H_5$, t-$C_4H_9$, Cy, Ph, MPh, Np, Th, Py, $OCH_3$, OPh, F, Cl, Br, I, CN, $N(CH_3)_2$, CHO, COOH, $COOCH_3$, COOPh, COPh, or $CF_3$; $R_3$ represents H, $CH_3$, $C_2H_5$, t-$C_4H_9$, $OCH_3$, OPh, $NO_2$, OH, F, $CF_3$, $C_2F_5$, or Ph; $R_4$ represents H, $CH_3$, $C_2H_5$, t-$C_4H_9$, Cy, Ph, MPh, Np, Th, Py, $OCH_3$, OPh, F, Cl, Br, I, CN, $N(CH_3)_2$, CHO, COOH, $COOCH_3$, COOPh, COPh, or $CF_3$; $R_8$ represents H, F, $CH_3$, Ph, or $CF_3$; $R_9$ represents H, $CH_3$, $C_2H_5$, t-$C_4H_9$, Cy, Ph, MPh, Np, Th, Py, $OCH_3$, OPh, F, Cl, Br, I, CN, $N(CH_3)_2$, CHO, COOH, $COOCH_3$, COOPh, COPh, or $CF_3$; $R_{10}$ represents H, $CH_3$, $C_2H_5$, t-$C_4H_9$, $OCH_3$, OPh, $NO_2$, OH, F, $CF_3$, $C_2F_5$, or Ph; $R_{11}$ represents H, $CH_3$, $C_2H_5$, t-$C_4H_9$, Cy, Ph, MPh, Np, Th, Py, $OCH_3$, OPh, F, Cl, Br, I, CN, $N(CH_3)_2$, CHO, COOH, $COOCH_3$, COOPh, COPh, or $CF_3$; and $R_5$ to $R_7$ and $R_{12}$ to $R_{14}$ each are H (wherein, Ph represents a phenyl group; MPh, a 4-methylphenyl group; Np, a naphthyl group; Th, a 2-thienyl group; Py, a 2-pyridyl group; and Cy, a cyclohexyl group.);

10. The light-emitting device described in any one of 2 to 9 above mentioned, wherein the organic thin film has a laminate structure at least containing a positive hole-transporting layer and a light-emitting layer;

11. The light-emitting device described in any one of 1 to 10 above mentioned, wherein an anode, a positive hole-transporting layer, a light-emitting layer, an electron-transporting layer, and a cathode are laminated in that order;

12. The light-emitting device described in any one of 1 to 11 above mentioned, wherein at least a positive hole-injecting layer, a positive hole-transporting layer, and an electron-transporting layer are formed between the anode and the cathode;

13. The light-emitting device described in any one of 1 to 12 above mentioned, wherein the compound having the basic skeleton represented by Formula (1) or (2) is contained as the host material of the light-emitting material in the light-emitting layer;

14. The light-emitting device described in any one of 1 to 13 above mentioned, wherein the compound having the basic skeleton represented by Formula (1) or (2) is contained as the dopant for the light-emitting layer;

15. The light-emitting device described in any one of 1 to 14 above mentioned, wherein a white light is emitted by combined use of a blue to green light-emitting material;

16. The light-emitting device described in any one of 1 to 15 above mentioned, wherein the positive hole-injecting layer described in 12 above mentioned contains a compound having the basic skeleton represented by the Formula (1) or (2);

17. The light-emitting device according to any one of 1 to 16, wherein the light-emitting device is a device for a display in a matrix mode and/or a segment mode;

18. A condensed polycyclic compound, represented by Formula (5):

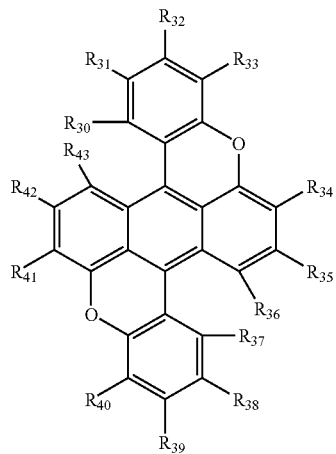

(5)

(wherein, $R_{30}$ to $R_{43}$ each independently represent a hydrogen atom, a halogen atom, an alkyl group which may be substituted with an aromatic residue, an aromatic oxy group, an alkyloxy group, or a halogen atom, or an aromatic residue which may be substituted with an aromatic residue, an aromatic oxy group, an alkyl group, an alkyloxy group, or a halogen atom; at least one of $R_{30}$ to $R_{43}$ is a halogen atom or an aromatic residue which may be substituted with an aromatic residue, an aromatic oxy group, an alkyl group, an alkyloxy group or a halogen atom; and the neighboring groups among $R_{30}$ to $R_{43}$ may bind to each other forming a ring(s) which may be substituted, however excluding the case where $R_{30}$ and $R_{31}$ and $R_{37}$ and $R_{38}$, or $R_{32}$ and $R_{33}$ and $R_{39}$ and $R_{40}$, bind to each other forming unsubstituted benzene rings and all of $R_{30}$ to $R_{43}$ that do not form a ring are a hydrogen atom.).

19. The condensed polycyclic compound according to 18, wherein two or more of $R_{30}$ to $R_{43}$ each are a halogen atom or an aromatic residue which may be substituted with an aromatic residue, an aromatic oxy group, an alkyl group, an alkyloxy group, or a halogen atom;

20. The condensed polycyclic compound according to 18 or 19, wherein the substituent groups $R_{34}$, $R_{35}$, $R_{36}$, $R_{41}$, $R_{42}$, and $R_{43}$ on the compound represented by Formula (5) each are a hydrogen atom; $R_{30}$ and $R_{37}$ each represent a hydrogen atom, a halogen atom, or a C1 to C4 alkyl group; $R_{31}$, $R_{33}$, $R_{38}$, and $R_{40}$ each represent a hydrogen atom, a halogen atom, an aromatic residue, a thienyl group, or a C1 to C4 alkyl group; and $R_{32}$ and $R_{39}$ each represent a hydrogen atom, a halogen atom, or a C1 to C4 alkyl group;

21. A condensed polycyclic compound represented by Formula (6):

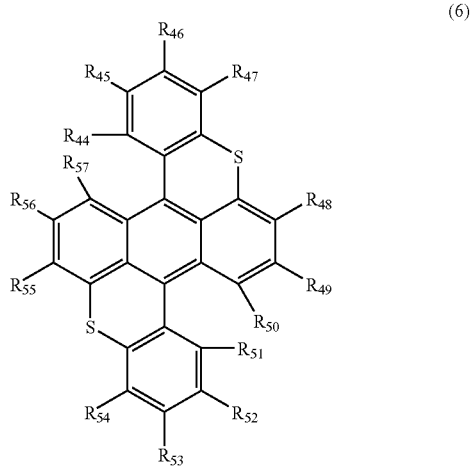

(6)

(wherein, $R_{44}$ to $R_{57}$ each independently represent a hydrogen atom, a halogen atom, an alkyl group which may be substituted with an aromatic residue, an aromatic oxy group, an alkyloxy group or a halogen atom, or an aromatic residue which may be substituted with an aromatic residue, an aromatic oxy group, an alkyl group, an alkyloxy group or a halogen atom; at least one of $R_{44}$ to $R_{57}$ is a halogen atom, an alkyl group which may be substituted with an aromatic residue, an aromatic oxy group, an alkyloxy group or a halogen atom, or an aromatic residue which may be substituted with an aromatic residue, an aromatic oxy group, an alkyl group, an alkyloxy group or a halogen atom; and the neighboring groups among $R_{44}$ to $R_{57}$ may bind to each other forming a ring(s) which may be substituted);

22. The condensed polycyclic compound according to 21, wherein two or more of $R_{44}$ to $R_{57}$ each are a halogen atom, an alkyl group which may be substituted with an aromatic residue, an aromatic oxy group, an alkyloxy group or a halogen atom, or an aromatic residue which may be substituted with an aromatic residue, an aromatic oxy group, an alkyl group, an alkyloxy group, or a halogen atom;

23. The condensed polycyclic compound according to 21 or 22, wherein the substituent groups $R_{48}$, $R_{49}$, $R_{50}$, $R_{55}$, $R_{56}$, and $R_{57}$ of the compound represented by Formula (6) each represent a hydrogen atom; $R_{44}$ and $R_{51}$ each represent a hydrogen atom, a halogen atom, or a C1 to C4 alkyl group; $R_{45}$, $R_{47}$, $R_{52}$, and $R_{54}$ each represent a hydrogen atom, a halogen atom, an aromatic residue, a thienyl group, or a C1 to C4 alkyl group; $R_{46}$ and $R_{53}$ each represent a hydrogen atom, a halogen atom, or a C1 to C4 alkyl group;

24. A condensed polycyclic compound represented by the following General Formula (7):

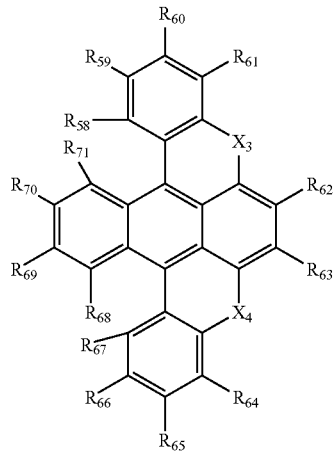

(wherein, $X_3$ and $X_4$ each independently represent an oxygen, sulfur, selenium, or tellurium atom, or $NR_{72}$; $R_{72}$ represents a hydrogen atom, or an aliphatic hydrocarbon or aromatic residue which may be substituted with an alkyl group, an alkyloxy group, an aromatic residue, an aromatic oxy group, or a halogen atom; $R_{58}$ to $R_{71}$ each represent a hydrogen atom, a halogen atom, an alkyl group which may be substituted with an aromatic residue, an aromatic oxy group, an alkyloxy group or a halogen atom, or an aromatic residue which may be substituted with an aromatic residue, an aromatic oxy group, an alkyl group, an alkyloxy group, or a halogen atom; at least one of $R_{58}$ to $R_{71}$ represents a halogen atom, an alkyl group which may be substituted with an aromatic residue, an aromatic oxy group, an alkyloxy group or a halogen atom, or an aromatic residue which may be substituted with an aromatic residue, an aromatic oxy group, an alkyl group, an alkyloxy group or a halogen atom; and the neighboring groups among the substituent groups $R_{58}$ to $R_{72}$ may bind to each other forming a ring(s) which may be substituted.);

25. A method of producing a condensed polycyclic compound having a basic skeleton represented by the following General Formulae (1) and (2):

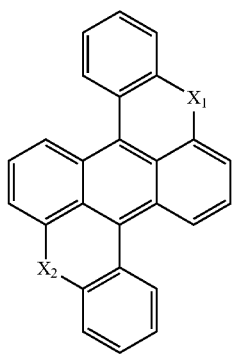

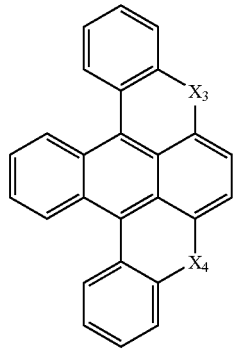

characterized by ring-closing a compound having the basic skeleton represented by the following General Formula (8) or (9):

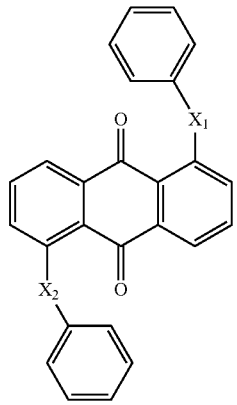

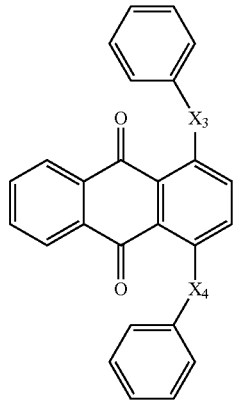

(wherein, $X_1$, $X_2$, $X_3$ and $X_4$ are the same as those described above.) in the presence of a sulfonic acid compound; and 26. The method of production described in 25 above mentioned, wherein the sulfonic acid compound is sulfuric acid, an alkylsulfonic acid which may be substituted, or an aromatic sulfonic acid which may be substituted.

BEST MODE FOR CARRYING OUT THE INVENTION

Figure 1:
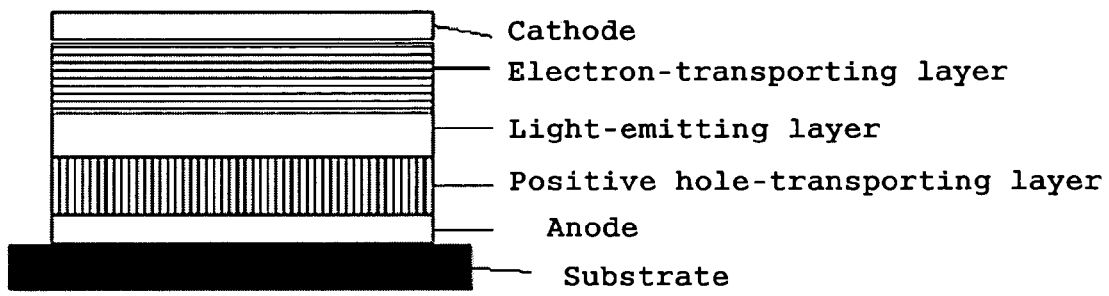
FIGS. 1 and 2 are schematic sectional views illustrating the layer structure of a light-emitting device according to the invention.

The light-emitting device, the compound, and the production method according to the invention will be described in detail respectively.

The invention relates to a light-emitting device which emitting light by electric energy having an organic thin film containing a positive hole-transporting layer, an electron-transporting layer, and others formed between an anode and a cathode, characterized in that the organic thin film contains a compound having at least the basic skeleton represented by the Formula (1) or (2).

Compounds having a basic skeleton represented by Formula (1) or (2) of the invention will be described below. In Formulae (1) and (2), $X_1$, $X_2$, $X_3$ and $X_4$ each independently represent an oxygen, sulfur, selenium, or tellurium atom, or $NR_{29}$. $R_{29}$ represents a hydrogen atom, an aliphatic hydrocarbon residue which may be substituted, or an aromatic residue which may be substituted. The compound having the basic skeleton represented by Formula (1) or (2) may have one or more substituent groups, and the substituent groups may bind to each other, forming a ring(s). Examples of the compounds having the basic skeleton represented by Formula (1) include the compounds represented by Formula (3) below, and examples of the compounds having the basic skeleton represented by Formula (2) include the compounds represented by Formula (4).

The compounds represented by Formulae (3) and (4) of the invention will be described in detail.

In Formulae (3) and (4), $X_1$, $X_2$, $X_3$ and $X_4$ each independently represent an oxygen, sulfur, selenium, or tellurium atom, or $NR_{29}$, and may be the same as or different from each other. Preferably, each group is an oxygen or sulfur atom or $NR_{29}$, and more preferably an oxygen or sulfur atom. $R_{29}$ represents a hydrogen atom, an aliphatic hydrocarbon residue which may be substituted, or an aromatic residue which may be substituted. The aliphatic hydrocarbon residue which may be substituted or aromatic residue which may be substituted of $R_{29}$ is the same as the aliphatic hydrocarbon residues which may be substituted or aromatic residue which may be substituted of $R_1$ to $R_{28}$ described below.

$R_1$ to $R_{28}$ each independently represent a hydrogen atom or a substituent group, and the neighboring substituent groups may bind to each other, forming a ring(s) which may be substituted. The substituent group represented by $R_1$ to $R_{28}$ is not particularly limited, and examples thereof include aliphatic hydrocarbon residues which may be substituted, aromatic residues which may be substituted, a cyano group, an isocyano group, a thiocyanato group, an isothiocyanato group, a nitro group, acyl groups, halogen atoms, a hydroxyl group, substituted or unsubstituted amino groups, alkoxyl groups, alkoxyalkyl groups, aromatic oxy groups which may be substituted, a carboxyl group, a carbamoyl group, an aldehydo group, alkoxycarbonyl groups, aromatic oxycarbonyl groups, and the like. Among them, aliphatic hydrocarbon residues which may be substituted, aromatic residues which may be substituted, a cyano group, a nitro group, acyl groups, halogen atoms, a hydroxyl group, substituted or unsubstituted amino groups, alkoxyl groups, aromatic oxy groups which may be substituted, and the like are preferable. Aliphatic hydrocarbon residues which may be substituted, aromatic residues which may be substituted, a nitro group, halogen atoms, substituted or unsubstituted amino groups, alkoxyl groups and the like are still more preferable; and among them, aliphatic hydrocarbon residues which may be substituted or aromatic residues which may be substituted and halogen atoms are particularly preferable. Most preferably are aromatic residues which may be substituted, and among the aromatic groups, phenyl groups which may be substituted are more preferable. Compounds having multiple aromatic residues which may be substituted, in particular multiple phenyl groups which may be substituted as the groups, as any of $R_1$ to $R_{28}$ groups are more preferable.

Examples of the aliphatic hydrocarbon residues which may be substituted include saturated or unsaturated, straight-chain, branched-chain, or cyclic aliphatic hydrocarbon residues which may be substituted, and the number of carbons thereof is preferably 1 to 20. Examples of the saturated or unsaturated, straight- or branched-chain aliphatic hydrocarbon residues include methyl, ethyl, propyl, isopropyl, n-butyl, iso-butyl, allyl, t-butyl, n-pentyl, n-hexyl, n-octyl, n-decyl, n-dodecyl, n-stearyl, and n-butenyl groups, and the like. Examples of the cyclic aliphatic hydrocarbons include cycloalkyl groups having 3 to 12 carbon atoms such as cyclohexyl, cyclopentyl, adamantyl, and norbornyl groups. These aliphatic hydrocarbon residues may be substituted additionally with any one of the substituent groups above mentioned (excluding alkyl groups). Preferable aliphatic hydrocarbon residues are alkyl groups having 1 to 6 carbon atoms which may be substituted. Preferable substituent groups on these aliphatic hydrocarbon residues include, for example, halogen atoms (more preferably chlorine, bromine, and fluorine atoms, and particularly preferably a fluorine atom), aromatic groups which may be substituted (more preferably phenyl groups which may be substituted), and the like.

Examples of the aromatic residues which may be substituted include substituted or unsubstituted five- to six-membered-ring aromatic residues which may contain 1 to 3 heteroatoms, aromatic residues having condensed rings of multiple, preferably 2 to 5, five- to six-membered rings, and the like. The heteroatoms include oxygen, nitrogen, sulfur, and other atoms; and a nitrogen atom is preferable. Typical examples of the aromatic residues include aromatic hydrocarbon residues such as phenyl, naphthyl, anthryl, phenanthryl, pyrenyl, and benzopyrenyl groups; aromatic heterocyclic ring residues such as pyridyl, pyrazyl, pyrimidyl, quinolyl, isoquinolyl, pyrrolyl, indolenyl, imidazolyl, carbazolyl, thienyl, and furyl groups; substituted aromatic heterocyclic ring residues such as benzoquinolyl, anthraquinolyl, pyranyl, and pyridonyl groups; and the like. Groups such as phenyl, naphthyl, pyridyl, and thienyl are preferable. In particular, phenyl and naphthyl groups are preferable. The term "aromatic" in the aromatic oxy group or the like is used in the same way as the "aromatic residue" above mentioned.

Examples of the acyl groups include alkylcarbonyl and aromatic oxycarbonyl groups having 1 to 10 carbon atoms and the like; alkylcarbonyl groups having 1 to 4 carbon atoms are preferable; and specific examples thereof include acetyl and propionyl groups, and the like.

The halogen atoms include atoms such as fluorine, chlorine, bromine, and iodine. Fluorine, chlorine, and bromine atoms are preferable, and fluorine and bromine atoms are more preferable. Examples of the substituted or unsubstituted amino groups include an amino group, mono- or di-alkylamino groups, mono- or di-aromatic amino groups, and the like; Specific examples thereof include mono- and di-methylamino groups, mono- and di-ethylamino groups, mono- and di-propylamino groups, mono- and di-phenylamino groups, mono- or di-C1 to C6 alkyl groups which may be substituted with a benzylamino group or the like, and the like; examples of the substituent groups on the alkyl groups include the substituent groups on the aliphatic hydrocarbon residues described above, and a phenyl group, a halogen atom or the like is preferable.

The alkoxyl group is, for example, a (C1 to C10) alkoxyl group; and preferable examples thereof include (C1 to C4) alkoxyl groups such as methoxy, ethoxy, propoxy, and butoxy groups, and the like.

The alkoxyalkyl group is, for example, a (C1 to C10) alkoxy (C1 to C10) alkyl group.

The aromatic oxy group is, for example, a (C1 to C20) aromatic oxy group which may contain 1 to 3 heteroatoms; and examples thereof include (C6 to C10) aromatic hydrocarbon oxy groups such as phenoxy and naphthyloxy groups; five- to ten-membered heterocyclic oxy groups containing 1 to 2 heteroatoms such as pyridyloxy, quinolyloxy, and thienyloxy; and the like. The alkoxycarbonyl group is, for example, a (C1 to C10) alkoxycarbonyl group.

Examples of the aromatic oxycarbonyl groups which may be substituted include phenoxycarbonyl groups which may be substituted with a halogen atom or the like, and the like.

The substituent group on the aliphatic hydrocarbon residue which may be substituted or the aromatic residue which may be substituted is not particularly limited, and, for example, is a group described for $R_1$ to $R_{28}$ above mentioned. Preferably, an aliphatic hydrocarbon residue which may be substituted, more preferably a C1 to C4 alkyl group which may be substituted; an aromatic residue which may be substituted, and more preferably phenyl group which may be substituted; or a halogen atom are included.

Most preferably among these substituent groups represented by $R_1$ to $R_{28}$ and $R_{29}$ are aliphatic hydrocarbon residues which may be substituted, aromatic residues which may be substituted, and halogen atoms. A preferable aliphatic hydrocarbon residue which may be substituted is an unsubstituted C1-C6 lower alkyl group or a halogen- or alkoxy-substituted lower alkyl group. Preferable examples of the aromatic residues which maybe substituted include phenyl, biphenyl, naphthyl, pyridino, thienyl, and furyl groups, as well as these groups having at least one group selected from the group consisting of aliphatic hydrocarbon residues, aromatic residues and a halogen atom as a substituent group. The aliphatic hydrocarbon residue is preferably a C1-C6 lower alkyl group; the aromatic residue is preferably a phenyl, biphenyl, naphthyl, pyridino, thienyl, or furyl group; and the halogen atom is preferably a fluorine, chlorine, or bromine atom.

The number of the substituent groups described above is 1 to 14, preferably 1 to 6, and more preferably 2 to 4. In Formula (3), $R_1$ to $R_4$ and $R_8$ to $R_{11}$ are preferably as substituent groups mentioned above. In Formula (4), $R_{15}$ to $R_{18}$ and $R_{21}$ to $R_{24}$ are preferably as substituent groups mentioned above. In particular, $R_2$, $R_4$, $R_9$, and $R_{11}$ are preferably as substituent groups mentioned above in Formula (3), and, $R_{16}$, $R_{18}$, $R_{21}$, and $R_{23}$ are preferably as substituent groups mentioned above in Formula (4).

In addition, the neighboring substituent groups of $R_1$ to $R_{14}$ and $R_{29}$ in Formula (3) above mentioned and $R_{15}$ to $R_{29}$ in Formula (4) may bind to each other, forming a ring(s) which may be substituted. In such a case, the newly formed ring(s) is added to the skeletal benzene ring to which these groups are bound, for example, as a condensed ring(s). The additional condensed ring(s) normally consists of two to four rings including the skeletal benzene ring and preferably two to three rings. Normally, the additional condensed ring(s) is preferably a five- to six-membered alicyclic or heterocyclic ring(s) which may contain 1 to 3 heteroatoms such as nitrogen, oxygen, and sulfur atoms. Preferable compounds are compounds having an additional condensed ring wherein the ring is a benzene or naphthalene ring, and more preferable compounds are those with an additional condensed benzene ring.

Preferably, the rings formed are those formed by mutual binding of any two of the neighboring groups of $R_1$ to $R_4$ and $R_8$ to $R_{11}$ in Formula (3) and rings formed by mutual binding of any two of the neighboring groups of $R_{15}$ to $R_{18}$ and $R_{21}$ to $R_{24}$ in Formula (4). More preferably, the rings are aromatic rings which may be substituted, that are formed by mutual binding of $R_1$ and $R_2$ and/or $R_3$ and $R_4$ and/or $R_8$ and $R_9$ and/or $R_{10}$ and $R_{11}$ in Formula (3) and aromatic rings which may be substituted, that are formed by mutual binding of $R_{15}$ and $R_{16}$ and/or $R_{17}$ and $R_{18}$ and/or $R_{21}$ and $R_{22}$ and/or $R_{23}$ and $R_{24}$ in Formula (4). Examples of the rings which may be substituted formed above mentioned include aromatic hydrocarbon rings such as benzene, naphthalene, and phenanthrene; aliphatic hydrocarbon rings such as cyclohexane, cyclobutane, and cyclopentane; heterocyclic ring such as pyridine, quinoline, pyran, azabicyclohexane, indole, and thiazole; and the like. Aromatic hydrocarbon rings such as benzene and naphthalene are preferable, and particularly, a benzene ring is preferable. In addition, the newly formed ring(s) may further bind to a neighboring substituent group, forming a ring(s). In such a case, the neighboring groups include not only the substituent groups on the carbons immediately next thereto, but also other substituent groups sterically accessible. In addition, the substituent group that may be present on the ring newly formed with a neighboring substituent group is not particularly limited, and examples thereof include the groups other than hydrogen in $R_1$ to $R_{29}$ described above; preferable examples include halogen atoms, a phenyl group, alkyl groups (preferably C1 to C4 alkyl groups), C1 to C4 alkoxycarbonyl groups, and the like.

A preferable compound represented by Formula (3) is a compound having at least one of $R_1$ to $R_{14}$ represented by an aromatic residue which may be substituted with an aromatic residue, an aromatic oxy group, an alkyl group, an alkyloxy group or a halogen atom, or a halogen atom; or a compound having a ring having a substituent group that is formed by mutual binding of any two of the neighboring groups of $R_1$ to $R_{14}$.

A preferable combination of substituent groups in Formula (3) is as follows:

$R_1$ and $R_8$ each independently represent a hydrogen atom, a (C1 to C6) alkyl group which may be substituted with a halogen atom, or a phenyl group which may be substituted with a (C1 to C4) alkyl group, preferably a hydrogen atom;

$R_2$, $R_4$, $R_9$ and $R_{11}$ each independently represent a hydrogen atom, a (C1 to C6) alkyl group which may be substituted with a halogen atom, a phenyl group which may be substituted with a (C1 to C4) alkyl group, a naphthyl group, a phenoxy group, a (C1 to C4) alkoxy group, a thienyl group, a pyridyl group, a cyclohexyl group, a halogen atom, a cyano group, a mono- or di-(C1 to C4) alkyl group, a carboxyl group, an aldehydo group, a (C1 to C4) alkoxycarbonyl group, a phenylcarbonyl group or a phenoxycarbonyl group, preferably a hydrogen atom, a (C1 to C4) alkyl group, a phenyl group or a halogen atom;

$R_3$ and $R_{10}$ each independently represent a hydrogen atom, a (C1 to C6) alkyl group which may be substituted with a halogen atom, a phenyl group which may be substituted with a (C1 to C4) alkyl group, a phenoxy group, a (C1 to C4) alkoxy group, a nitro group, a hydroxy group, or a halogen atom, preferably a hydrogen atom or a phenyl group;

$X_1$ and $X_2$ each independently represent an oxygen, sulfur, or selenium atom or $NR_{29}$; $R_{29}$ represents a hydrogen atom, a (C1 to C6) alkyl group which may have a halogen atom or a phenyl group as a substituent group, a phenyl group which may have a (C1 to C4) alkyl group or a phenyl group as a substituent group;

preferably $X_1$ and $X_2$ each independently represent an oxygen or sulfur atom;

and the groups $R_1$ to $R_{14}$ other than those above mentioned each are a hydrogen atom.

More preferable compounds are those in which one to four, preferably two to four, more preferably three to four of the groups $R_1$ to $R_{14}$ each represent a phenyl group which may be substituted or a (C1 to C6) alkyl group or halogen atom, and other groups represent a hydrogen atom.

When one or more rings are formed by the neighboring substituent groups described above, preferable compounds include compounds having a benzene ring as the additionally formed ring (benzene ring-condensed compounds), and more preferable compounds are those in which $R_1$ and $R_2$ and $R_8$ and $R_9$ form respectively benzene rings or $R_3$ and $R_4$ and $R_{10}$ and $R_{11}$ form respectively benzene rings. In such a case, naphthalene rings are formed together with these substituted skeletal benzene rings. The naphthalene ring may be substituted with a halogen atom or a group such as a phenyl, biphenyl, naphthyl, thienyl, or C1 to C4 alkyl group. When $R_1$ and $R_2$ and $R_8$ and $R_9$ form respectively benzene rings, the substituent groups mentioned above are preferably substituted as $R_4$ or/and $R_{11}$, while when $R_3$ and $R_4$ and $R_{10}$ and $R_{11}$ form respectively benzene rings, the substituent groups mentioned above are preferably substituted as $R_2$ or/and $R_9$. Examples of the substituent groups which may be present on the benzene ring additionally formed by mutual binding of two substituent groups include halogen atoms, C1 to C4 alkoxycarbonyl groups, C1 to C4 alkyl groups, a phenyl group, and the like. The other groups are the same as those when the neighboring substituent groups do not form a ring.

The terms described so far are applicable to other General Formulae, unless particularly specified otherwise.

The preferable combinations of substituent groups in Formula (4) are fundamentally the same as those in Formula (3), and $R_1$ to $R_{14}$ in Formula (3) above mentioned correspond respectively to $R_{15}$ to $R_{28}$ in Formula (4).

Hereinafter, the condensed polycyclic compound (5) according to the invention will be described in detail.

In Formula (5), $R_{30}$ to $R_{43}$ each independently represent a hydrogen atom, a halogen atom, an alkyl group which may have an aromatic, aromatic oxy, or alkyloxy group or a halogen atom as a substituent group, or an aromatic residue which may have an aromatic, aromatic oxy, alkyl, or alkyloxy group, or a halogen atom as a substituent group; and at least one of $R_{30}$ to $R_{43}$ represents an aromatic residue which may be substituted with an aromatic residue, an aromatic oxy group, an alkyl group, an alkyloxy group or a halogen atom, or a halogen atom. The neighboring groups among $R_{30}$ to $R_{43}$ may bind to each other, forming a ring(s) (excluding the case when the neighboring groups among $R_{30}$ to $R_{43}$ form one or more rings and all other groups not involved in ring formation represent a hydrogen atom).

The alkyl group is a straight-chain, branched-chain, or cyclic alkyl group, and the number of carbons thereof is preferably 1 to 20. Examples of the straight- or branched-chain alkyl groups include methyl, ethyl, propyl, isopropyl, n-butyl, iso-butyl, t-butyl, n-pentyl, n-hexyl, n-octyl, n-decyl, n-dodecyl, and n-stearyl groups, and the like. Examples of the cyclic alkyl groups include cycloalkyl groups having 3 to 12 carbon atoms; specific examples thereof include cyclohexyl, cyclopentyl, adamantyl, and norbornyl groups, and the like. More preferable alkyl groups are alkyl groups having 1 to 6 carbon atoms. These alkyl groups may be substituted additionally with an aromatic residue, an aromatic oxy group, an alkyloxy group, a halogen atom, or the like.

The aromatic residue which may be substituted is the same as that described for $R_1$ to $R_{29}$. Examples of the halogen atoms include atoms such as fluorine, chlorine, bromine, and iodine; and fluorine, chlorine, and bromine atoms are preferable.

Sterically hindered compounds are more effective in giving a more uniform organic thin film as will be described below. Therefore, the compound of Formula (5) preferably has substituted aromatic residues to some extent.

The number of the substituent groups described above is 1 to 14, preferably 1 to 6, and still more preferably 2 to 4 piece. $R_{30}$ to $R_{33}$ and $R_{37}$ to $R_{40}$ are preferably as substituent groups mentioned above, and $R_{31}$, $R_{33}$, $R_{38}$, and $R_{40}$ are more preferably as substituent groups mentioned above.

In Formula (5) above mentioned, the neighboring groups among $R_{30}$ to $R_{43}$ may bind to each other, forming a substituted ring. Preferably, rings are formed by mutual binding of any two of the neighboring groups of $R_{30}$ to $R_{33}$, $R_{37}$ to $R_{40}$ and more preferably; substituted aromatic rings are formed by mutual binding of $R_{30}$ and $R_{31}$ and/or $R_{32}$ and $R_{33}$ and/or $R_{37}$ and $R_{38}$ and/or $R_{39}$ and $R_{40}$. In such a case, the neighboring groups, not only the substituent groups on the carbons immediately next to each other, but also other substituent groups sterically accessible, may be bound to each other. Examples of the substituent groups on the rings if present include the alkyl groups which may be substituted and the aromatic residue which may be substituted, and halogen atoms, described above.

Examples of the rings which may be substituted described above (rings formed by binding of substituent group which may be substituted) include those described in Formulae (3) and (4); and aromatic rings such as benzene and naphthalene are preferable. Particularly, benzene ring, and the ring may have one or more substituents is preferable. Examples of the substituent groups include the aliphatic hydrocarbon residues which may be substituted and the aromatic residues which may be substituted, and halogen atoms, described above.

The compound is a new compound, and the compounds having a halogen atom or an aromatic residue which may be substituted, which have a higher melting point and a glass dislocation point (Tg point) and thus are improved in heat resistance, are used favorably as an organic electronic material, in particular as a material for organic EL devices.

Hereinafter, the condensed polycyclic compound (6) according to the invention will be described in detail.

In Formula (6), $R_{44}$ to $R_{57}$ each independently represent, a hydrogen atom, a halogen atom, an alkyl group which may be substituted with an aromatic group, an aromatic oxy group, an alkyloxy group, or a halogen atom, an aromatic residue which may be substituted with an aromatic residue, an aromatic oxy group, an alkyl group, an alkyloxy group or a halogen atom; and at least one of $R_{44}$ to $R_{57}$ represents an aromatic residue which may be substituted with an aromatic residue, an aromatic oxy group, an alkyl group, an alkyloxy group or a halogen atom, an alkyl group which may be substituted with an aromatic group, an aromatic oxy group, an alkyloxy group or a halogen atom, or a halogen atom. In addition, the neighboring groups among $R_{44}$ to $R_{57}$ may bind to each other, forming a ring(s) which may be substituted.

The alkyl and aromatic residues are the same as the alkyl and aromatic residues described as the substituent groups of $R_{30}$ to $R_{43}$. The aromatic residues which may be substituted are the same as those described for $R_1$ to $R_{29}$. Examples of the halogen atoms include atoms such as fluorine, chlorine, bromine, and iodine; and fluorine, chlorine, and bromine atoms are preferable.

Sterically hindered compounds are more effective in giving a more uniform film organic thin film when formed as will be described below. Therefore, the compound preferably has an aromatic residues, more preferably multiple aromatic residues, as substituent groups. The number of the substituent groups in Formula (6) above mentioned is 1 to 14, preferably 1 to 6, and more preferably 2 to 4. Preferably, $R_{44}$ to $R_{47}$ and $R_{51}$ to $R_{54}$ represent as substituent groups mentioned above; and in particular $R_{45}$, $R_{47}$, $R_{52}$, and $R_{54}$ represent as substituent groups mentioned above.

In the condensed polycyclic compound of Formula (6) above mentioned, the neighboring groups among $R_{44}$ to $R_{57}$ may bind to each other, forming a ring(s) which may be substituted. The rings are formed by mutual binding of any two of the neighboring groups of $R_{44}$ to $R_{47}$ and $R_{51}$ to $R_{54}$ are preferable; and more preferably, aromatic rings which may be substituted are formed by mutual binding of $R_{44}$ and $R_{45}$ and/or $R_{46}$ and $R_{47}$ and/or $R_{51}$ and $R_{52}$ and/or $R_{53}$ and $R_{54}$. In such a case, the neighboring groups, not only the substituent groups on the carbons immediately next thereto, but also other substituent groups sterically accessible, may be bound to each other. The substituent group on the ring which may be substituted is not particularly limited, and examples thereof include the alkyl groups which may be substituted, the aromatic residues which may be substituted and the halogen atoms described above.

Similarly to Formulae (3) and (4), preferable examples of the rings which may be substituted include aromatic ring such as benzene and naphthalene; and particularly, a benzene ring is preferable. These rings may have additionally one or more substituents. The substituent groups include the aliphatic hydrocarbon residues which may be substituted, the aromatic residues which may be substituted and halogen atoms described above.

The compound is a new compound, and the compounds containing a halogen atom, an aliphatic residue which may be substituted or an aromatic residue which may be substituted have a higher melting point and a glass dislocation point (Tg point) and thus are superior in heat resistance. Thus, they may be used favorably as an organic electronic material, in particular as a material for organic EL devices.

The condensed polycyclic compound (7) according to the invention will be described in detail below.

In principle, the description above mentioned for $X_3$, $X_4$, and $R_1$ to $R_{28}$ in Formulae (3) and (4) apply to $X_3$, $X_4$, and $R_{58}$ to $R_{71}$ in Formula (7). Thus, $R_{15}$ to $R_{28}$ above mentioned correspond respectively to $R_{58}$ to $R_{71}$. Preferable examples thereof will be described below for clarity.

$X_3$ and $X_4$ in Formula (7) each independently represent an oxygen, sulfur, selenium, or tellurium atom, or $NR_{72}$. $R_{72}$ represents a hydrogen atom or an aliphatic hydrocarbon or aromatic residue which may be substituted with an alkyl group, an alkyloxy group, an aromatic group, an aromatic oxy group or a halogen atom. $R_{58}$ to $R_{71}$ each represent a hydrogen atom, a halogen atom, an alkyl group which may be substituted with an aromatic residue, an aromatic oxy group, or an alkyloxy group or a halogen atom, or an aromatic residue which may be substituted with an aromatic residue, an aromatic oxy group, an alkyl group, an alkyloxy group or a halogen atom; and at least one of $R_{58}$ to $R_{71}$ represents a halogen atom; an alkyl group which may contain an aromatic residue, an aromatic oxy group, an alkyloxy group or a halogen atom as its substituent group; or an aromatic residue which may have an aromatic residue, an aromatic oxy group, an alkyl group, an alkyloxy group or a halogen atom as its substituent group. In addition, the neighboring groups of the substituent groups of $R_{58}$ to $R_{72}$ may bind to each other, forming a ring(s) which may be substituted. In such a case, compounds in which at least one of the substituent groups, (i.e., substituent groups forming no ring among $R_{58}$ to $R_{71}$ or the substituent groups that may be present on the newly formed rings), represents a halogen atom, an alkyl group which may be substituted with an aromatic residue, an aromatic oxy group, an alkyloxy group or a halogen atom, or an aromatic residue which may be substituted with an aromatic residue, an aromatic oxy group, an alkyl group, an alkyloxy group or a halogen atom are preferable new compounds.

The alkyl groups and the aromatic residues are the same as the alkyl groups and the aromatic residues described for the substituent groups of $R_{30}$ to $R_{43}$. The aliphatic hydrocarbon residues which may be substituted and the aromatic residues which may be substituted are the same as those described for $R_1$ to $R_{28}$. Examples of the halogen atoms include atoms such as fluorine, chlorine, bromine, and iodine; and a fluorine atom is preferable.

In addition, the neighboring groups of the substituent groups represented by $R_{58}$ to $R_{72}$ in Formula (7) above mentioned may bind to each other, forming a ring(s) which may be substituted. Preferably, the rings are formed by mutual binding of any two of the neighboring groups of $R_{58}$ to $R_{61}$ and $R_{64}$ to $R_{67}$; and more preferably, the aromatic rings which may be substituted are formed by mutual binding of $R_{58}$ and $R_{59}$ and/or $R_{60}$ and $R_{61}$ and/or $R_{64}$ and $R_{65}$ and/or $R_{66}$ and $R_{67}$. In such a case, the neighboring groups, not only the substituent groups on the carbons immediately next thereto but also other substituent groups sterically accessible, may be bound to each other. The substituent group on the ring which may be substituted is not particularly limited, and examples thereof include the alkyl groups which may be substituted, the aromatic residues which may be substituted, and the halogen atoms described above, and the like.

The rings which may be substituted are the same as those described in Formula (5).

The preferable combinations of substituent groups in Formula (5) to (7) are fundamentally the same as those in Formula (3), and thus, the description on corresponding substituent groups also applies to the substituent groups in Formula (5) to (7).

Hereinafter, methods of producing the compounds above mentioned will be described.

The compounds represented by Formulae (1), (2), (3) and (4) above mentioned can be produced, for example, according to the methods described in J. Chem. Soc., (1956), 2652; Nippon Kagakukaishi JP, 1989, (5), 876; J. Photopolym. Sci. Technol., 11, 41 (1998); Nippon Kagakukaishi JP, 1988, (1), 97; and Mol. Cryst. Liq. Cryst., 1994, Vol. 246, 119 or the modifications thereof. Alternatively, they can also be produced by the production method according to the invention below.

For example, the intermediate represented by the following General Formula (12) is obtained in a reaction of 1 part by weight of a dihalogenated anthraquinone derivative (10) such as 1,5-dichloroanthraquinone (Formula (3)) and 2 parts by weight of a derivative (11) such as phenol or thiophenol. (In Formulae (10), (11) and (12), $R_1$ to $R_{14}$ are the same as those in Formula (3).).

The reaction for obtaining the intermediate (12) is conducted as follows: A derivative such as phenol or thiophenol (11) is first converted to the potassium salt of the derivative in a reaction with potassium hydroxide in toluene, for improvement in its reactivity. The potassium salt obtained is then allowed to react with a halogenated anthraquinone derivative (10), for example in the presence of copper powder and for example in a polar solvent such as dimethylformamide (DMF) or N-methylpyrrolidone (NMP), to give an intermediate (12). The reaction temperature is 80 to 200° C., and the reaction period approximately 1 to 8 hours.

Ring closure reaction of the resulted intermediate (12) in a molten salt of aluminum chloride and sodium chloride gives a compound represented by Formula (3). The reaction temperature is 110° C. to 150° C., and the reaction period approximately 0.5 to 6 hours.

(a compound represented by Formula (4) can be prepared in a similar manner by using 1,4-dichloroanthraquinone or the like as the dihalogenated anthraquinone derivative.)

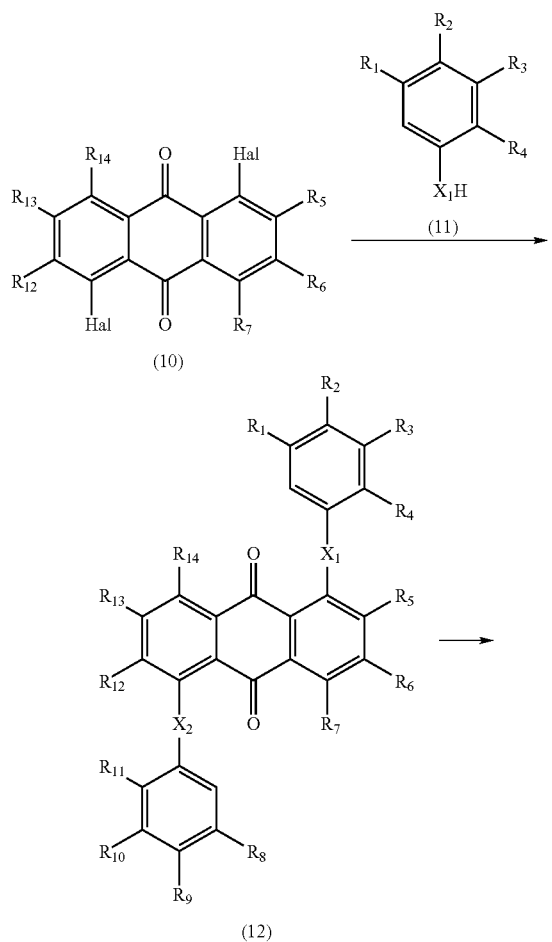

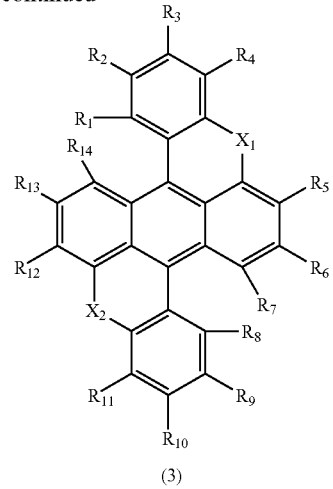

(as above mentioned in Formulae (10), (11) and (12), $R_1$ to $R_{14}$ are the same as those in Formula (3).)

High-purity compounds represented by Formulae (1) and (2) are produced in higher workability by the production method according to the invention.

Hereinafter, the production method according to the invention will be described.

The production method according to the invention is a method of producing a compound having the basic skeleton represented by Formula (1) or (2) by ring closure of a compound having the basic skeleton represented by Formula (8) or (9) above mentioned in the presence of a sulfonic acid compound, and more specifically, is a method suitable for producing the compound represented by Formula (3) or (4).

The sulfonic acid compound which can be used in the production method according to the invention may be a compound that is solid at room temperature (25° C.), but a compound liquid at room temperature is preferable in handling. Specific examples thereof include sulfuric acid; alkylsulfonic acids (preferably, C1 to C4 alkyl-sulfonic acid which may be substituted with halogen atoms) such as methanesulfonic acid, ethanesulfonic acid, and trifluoromethanesulfonic acid; aromatic sulfonic acids (preferably, benzenesulfonic acids which may be substituted with a C1 to C4 alkyl group) such as benzenesulfonic acid and toluenesulfonic acid. Sulfuric acid, methanesulfonic acid, benzenesulfonic acid, and toluenesulfonic acid are preferable. Particularly, sulfuric acid and methanesulfonic acid are preferable. These sulfonic acid compounds may be used alone or as a mixture of two or more. The content of the sulfonic acid is normally 0.1 to 100 parts by weight, preferably 2 to 30 parts by weight, with respect to 1 part by weight of the compound of Formula (1) or (2).

In the production method according to the invention, a auxiliary agent may be used or other reaction solvents may be mixed additionally. Examples of the auxiliary agents for use include those that accelerate the ring closure reaction such as phosphorus pentoxide, hydrogen fluoride, polyphosphoric acid, and molecular sieve. When used, the auxiliary agent is used in an amount of normally 0.001 to 1 part by weight, more preferably 0.05 to 0.2 part by weight, with respect to 1 part by weight of the sulfonic acid compound. Examples of the reaction solvents for use include water; organic acids such as acetic acid and formic acid: inorganic acids such as phosphoric acid; protic solvents such as methanol and ethylcellusolve;

polar aprotic solvents such as acetic anhydride, dimethylimidazoline (DMI), and dimethylformamide (DMF); hydrocarbons such as hexane, decane, cyclohexane, and decaline; aromatic solvents such as benzene, toluene, xylene, and mesitylene. Water, acetic acid, phosphoric acid, toluene, xylene, and acetic anhydride are preferable; and acetic acid, phosphoric acid, and acetic anhydride are more preferable. When used, the reaction solvent is used in an amount of normally 0.1 to 100 parts by weight, more preferably 0.5 to 10 parts by weight, with respect to 1 part by weight of the sulfonic acid compound.

In the production method according to the invention, the reaction temperature is usually −20 to 250° C., preferably 50 to 200° C., more preferably 90 to 180° C., and still more preferably 110 to 160° C.; and the reaction period is normally, approximately 0.5 to 6 hours. The reaction may be performed under atmospheric pressure or under reduced pressure. After reaction, the reaction mixture is diluted as needed with a solvent such as water or alcohol, and the desirable product is separated by filtration. Then, the product is washed as needed with a solvent or the like, to give a desirable compound. It is possible to raise the purity of the product as needed, for example, by silica gel chromatography, recrystallization, or the like.

In addition to the method above mentioned, an intermediate thiophenol compound (15) may be prepared according to the following method.

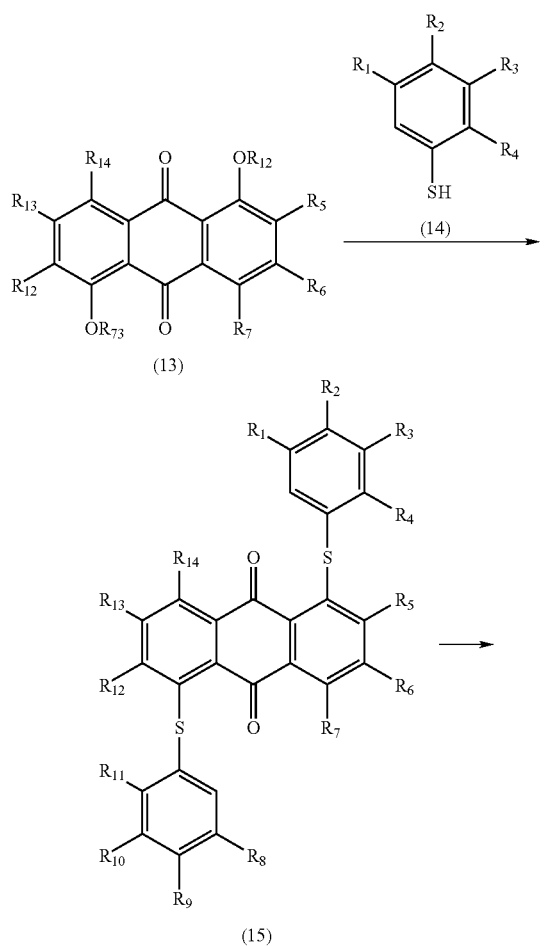

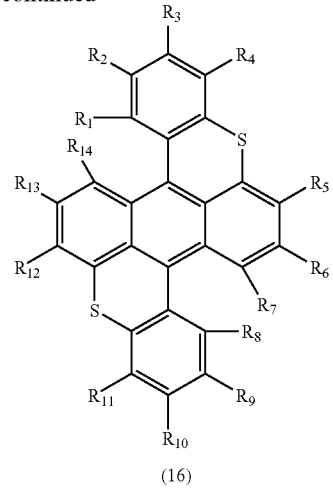

(in Formulae (13), (15), and (16), $R_1$ to $R_{14}$ are the same as those in Formula (3); and $R_{72}$ and $R_{73}$ each independently represent an alkyl group which may be substituted or an aromatic residue which may be substituted.)

In the method, an intermediate represented by Formula (15) is produced by allowing an anthraquinone compound represented by Formula (13) to react with a thiophenol derivative (14) in the presence of a base.

Examples of the bases for use in the method of production above mentioned include inorganic bases such as caustic soda, caustic potash, slaked lime, thallium hydroxide, potassium carbonate, and sodium carbonate; organic bases such as triethylamine, pyridine, sodium ethoxide, diazabicycloundecene (DBU), piperazine, and piperidine. Inorganic salts such as caustic soda, caustic potash, slaked lime, and thalliumhydroxide are preferable; and particularly, caustic soda and caustic potash are preferable. These bases may be used alone or as a mixture of two or more. The amount of the base used is normally 0.1 to 100 parts by weight, preferably 0.3 to 4 parts by weight, with respect to 1 part by weight of the compound (13).

A solvent may be used in the method of production above mentioned. Typical examples of the solvents include polar aprotic solvents such as DMI, DMF, and NMP; hydrocarbons such as hexane, decane, cyclohexane, and decaline; aromatic solvents such as benzene, toluene, xylene, and mesitylene; and the like. DMF, DMI, and toluene are preferable. These solvents may be used alone or as a mixture of two or more. The amount of the solvent used is normally 1 to 100 parts by weight, preferably 5 to 20 parts by weight, with respect to 1 part by weight of the compound (13).

In the method of production above mentioned, the reaction temperature is usually −20 to 250° C., preferably 80 to 130° C., and the reaction period is usually, approximately 0.5 to 6 hours. The reaction is favorably performed under an inert atmosphere, for example, of nitrogen or argon. After completion of reaction, the reaction mixture may be diluted as needed with a solvent such as water or alcohol, and the desired product is separated by filtration. Then, the product is washed as needed with a solvent or the like, to give an intermediate represented by Formula (15). It is possible to raise the purity of the intermediate as needed, for example, by silica gel chromatography or recrystallization.

In addition, compounds having substituent groups represented by Formulae (3) and (4) may be prepared by substitution reaction of a basic skeleton previously prepared. Such compounds can be produced, for example, by preparing a compound having a nitro group by nitrating a compound having the basic skeleton represented by Formula (1), reducing the compound into an amino group-containing compound, and preparing a substituted amino group-containing compound in substitution reaction according to the method described in J. Photopolym. Sci. Technol., 11, 41 (1998); or alternatively, by preparing a basic skeleton, halogenating or sulfonating the basic skeleton, and then subjecting it to substitution reaction.

Suitable specific examples of the compounds according to the invention are shown below.

First, typical favorable examples of the compounds represented by Formula (3) include the followings: First of all, examples of the compounds represented by Formula (17), wherein each of $R_5$ to $R_7$ and $R_{12}$ to $R_{14}$ is a hydrogen atom and $X_1$ and $X_2$ are oxygen atoms, are shown in Table 1. In the Table, a phenyl group is designated as Ph; 4-methylphenyl group, 4MPh; naphthyl group, Np; 2-thienyl group, Th; 2-pyridyl group, Py; and cyclohexyl group, Cy.

TABLE 1

(17)

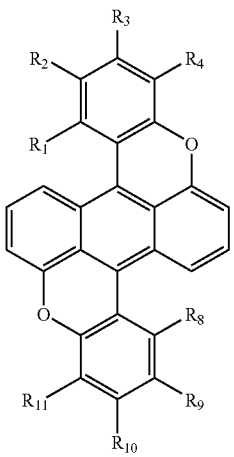

| Compound No. | $R_1$ | $R_2$ | $R_3$ | $R_4$ | $R_8$ | $R_9$ | $R_{10}$ | $R_{11}$ |
|---|---|---|---|---|---|---|---|---|
| 1 | H | H | H | H | H | H | H | H |
| 2 | H | $CH_3$ | H | H | H | $CH_3$ | H | H |
| 3 | H | $C_2H_5$ | H | H | H | $C_2H_5$ | H | H |
| 4 | H | $CH_3$ | H | $CH_3$ | H | $CH_3$ | H | $CH_3$ |
| 5 | H | H | $C_2H_5$ | H | H | H | $C_2H_5$ | H |
| 6 | $CH_3$ | H | $CH_3$ | H | $CH_3$ | H | $CH_3$ | H |
| 7 | H | $t$-$C_4H_9$ | H | H | H | $t$-$C_4H_9$ | H | H |
| 8 | H | $CH_3$ | H | H | H | H | H | H |
| 9 | H | Ph | H | H | H | Ph | H | H |
| 10 | H | H | H | Ph | H | H | H | Ph |
| 11 | H | H | Ph | H | H | H | Ph | H |
| 12 | H | Np | H | H | H | Np | H | H |
| 13 | H | H | H | Np | H | H | H | Np |
| 14 | H | H | $t$-$C_4H_9$ | H | H | H | $t$-$C_4H_9$ | H |
| 15 | H | OPh | H | H | H | OPh | H | H |
| 16 | H | H | OPh | H | H | H | OPh | H |
| 17 | H | $OCH_3$ | H | H | H | $OCH_3$ | H | H |
| 18 | H | H | $OCH_3$ | H | H | H | $OCH_3$ | H |
| 19 | H | Th | H | H | H | Th | H | H |
| 20 | H | Py | H | H | H | Py | H | H |
| 21 | H | $CH_3$ | H | H | H | Cy | H | H |
| 22 | H | $CH_3$ | H | H | H | Ph | H | H |
| 23 | Ph | H | H | H | H | H | Ph | H |
| 24 | H | Py | H | H | H | H | H | H |
| 25 | H | Cl | H | H | H | Cl | H | H |
| 26 | H | I | H | H | H | I | H | H |
| 27 | H | CN | H | H | H | CN | H | H |
| 28 | H | H | $NO_2$ | H | H | H | $NO_2$ | H |
| 29 | H | H | OH | H | H | H | OH | H |
| 30 | H | $N(CH_3)_2$ | H | H | H | $N(CH_3)_2$ | H | H |
| 31 | H | COOH | H | H | H | H | H | H |
| 32 | H | CHO | H | H | H | H | H | H |
| 33 | H | $COOCH_3$ | H | H | H | $COOCH_3$ | H | H |
| 34 | H | 4MPh | H | H | H | 4MPh | H | H |
| 35 | $CH_3$ | $CH_3$ | $CH_3$ | H | $CH_3$ | $CH_3$ | $CH_3$ | H |
| 36 | H | COPh | H | H | H | COPh | H | H |

TABLE 1-continued (17)

[Structure of formula (17) with substituents $R_1$ through $R_{11}$]

| Compound No. | $R_1$ | $R_2$ | $R_3$ | $R_4$ | $R_8$ | $R_9$ | $R_{10}$ | $R_{11}$ |
|---|---|---|---|---|---|---|---|---|
| 37 | H | COOPh | H | H | H | COOPh | H | H |
| 38 | F | F | F | H | F | F | F | H |
| 39 | H | Ph | H | Ph | H | Ph | H | Ph |
| 40 | H | F | H | H | H | F | H | H |
| 41 | H | H | H | F | H | H | H | F |
| 42 | H | F | H | F | H | F | H | F |
| 43 | H | Br | H | H | H | Br | H | H |
| 44 | H | Br | H | Br | H | Br | H | Br |
| 45 | H | H | H | Br | H | H | H | Br |
| 46 | H | I | H | F | H | I | H | F |
| 47 | H | $CF_3$ | H | H | H | $CF_3$ | H | H |
| 48 | H | $CF_3$ | H | $CF_3$ | H | $CF_3$ | H | $CF_3$ |
| 49 | H | H | $C_2F_5$ | H | H | H | $C_2F_5$ | H |
| 50 | $CF_3$ | H | $CF_3$ | H | $CF_3$ | H | $CF_3$ | H |

Examples of other compounds represented by Formula (17) ($X_1$ and $X_2$ are oxygen atoms) are listed below.

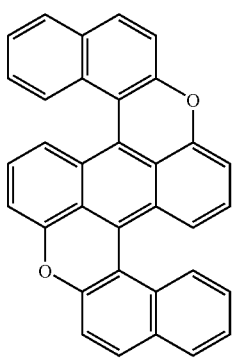

No. 51

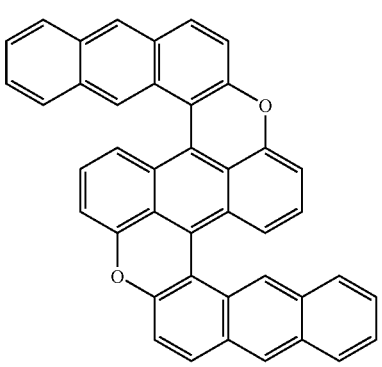

No. 52

No. 53
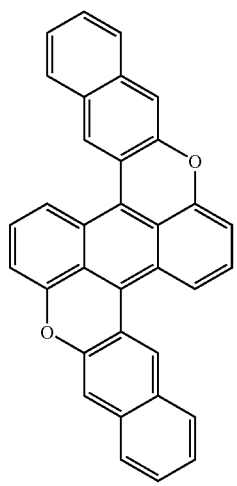
No. 54
No. 55
No. 56
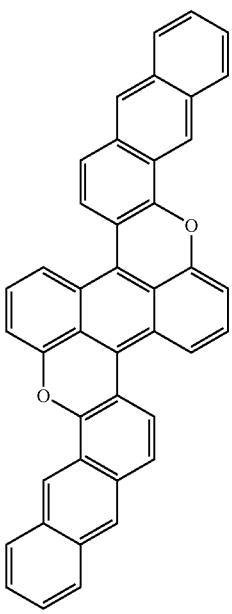
No. 57
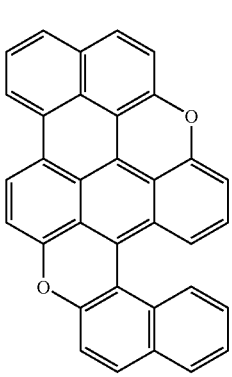
No. 58
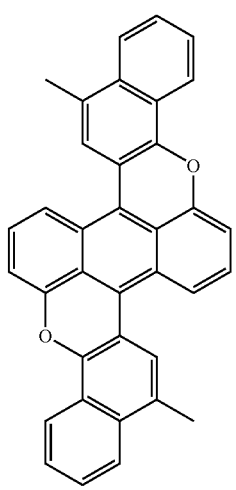

-continued
No. 59
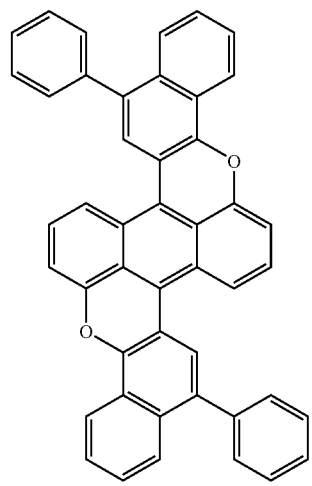
No. 60
No. 61
No. 62
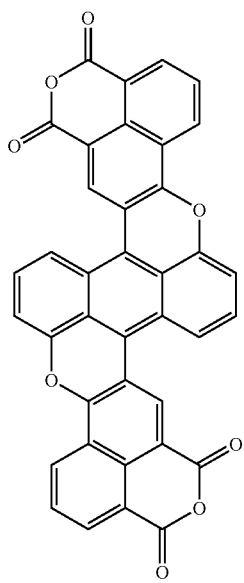
No. 63
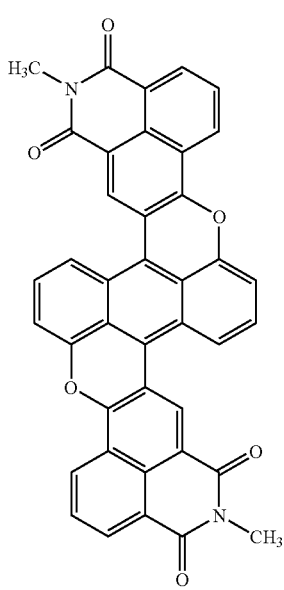
No. 64
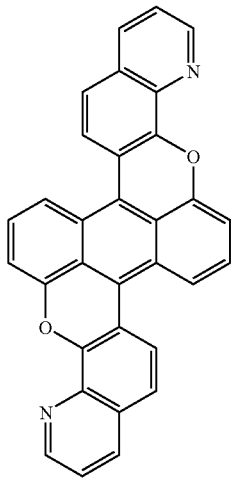

-continued
No. 65
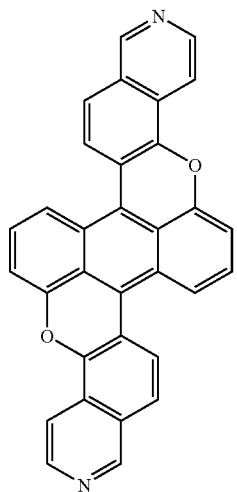
No. 66
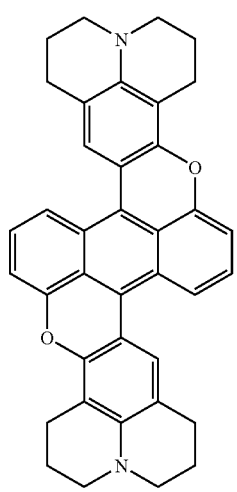
No. 67
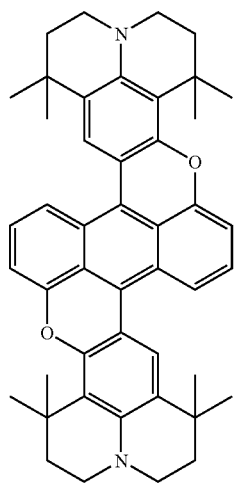
-continued
No. 68
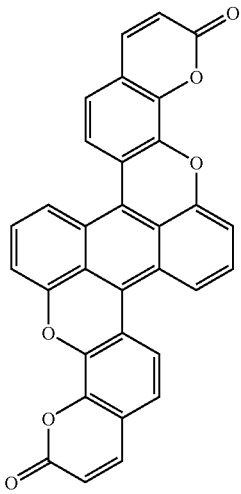
No. 69
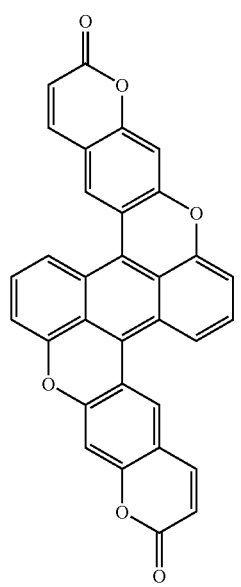
No. 70
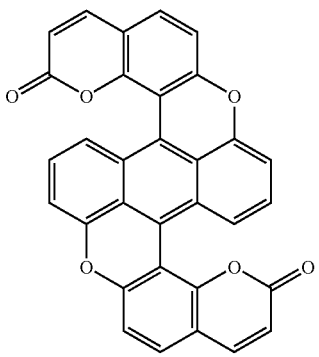

-continued
No. 71
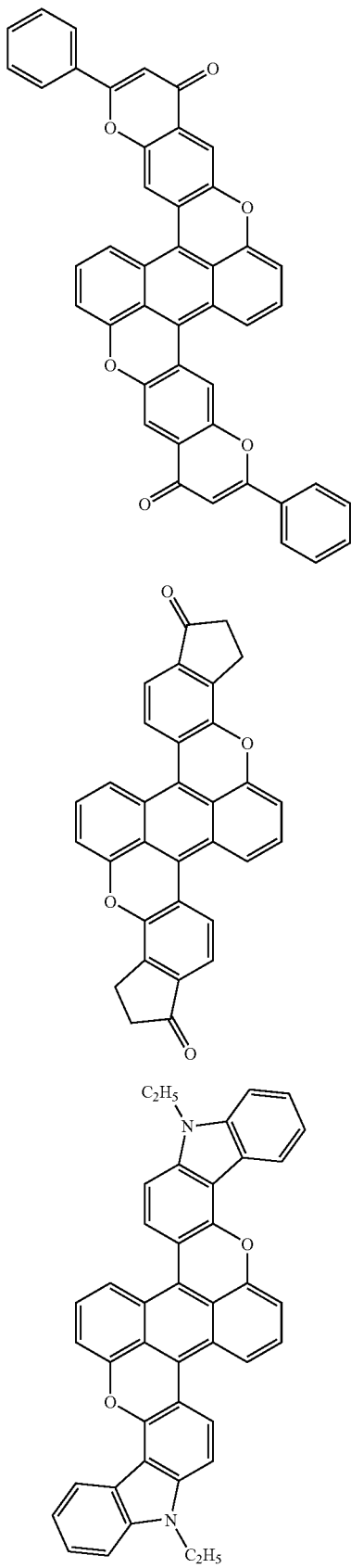
No. 72
No. 73
-continued
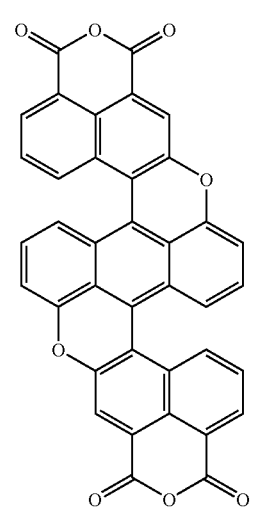
No. 74
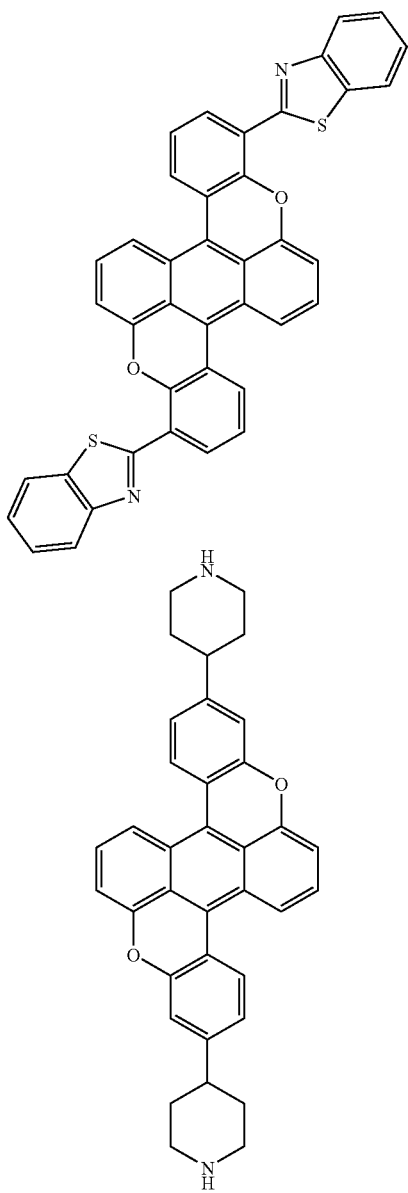
No. 75
No. 76

No. 77
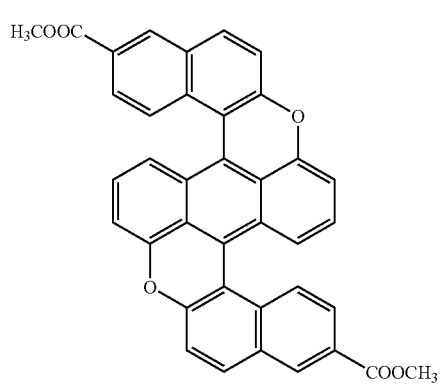
No. 78
No. 79
No. 80
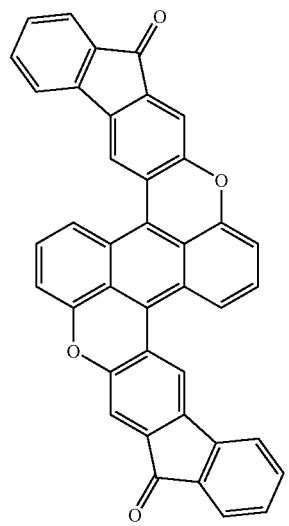
No. 81
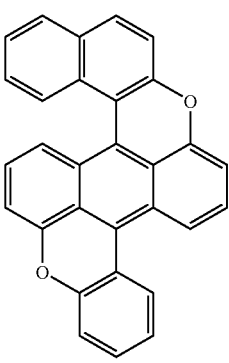
No. 82
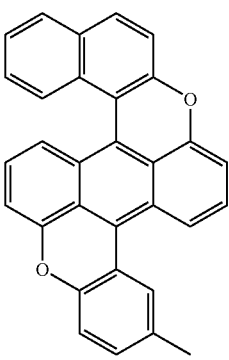

-continued
No. 83
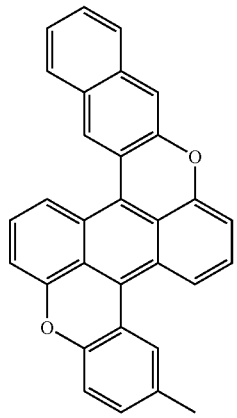
No. 84
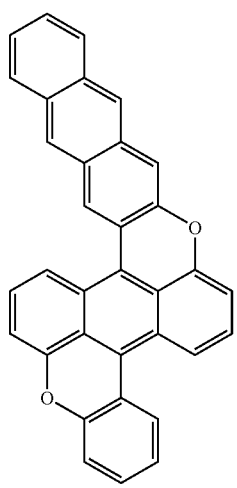
No. 85
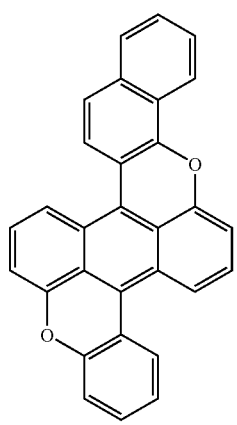
-continued
No. 86
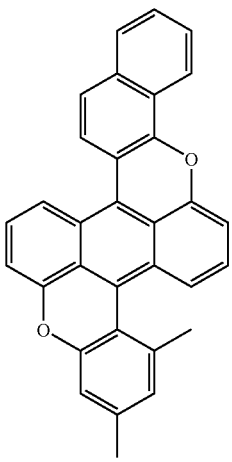
No. 87
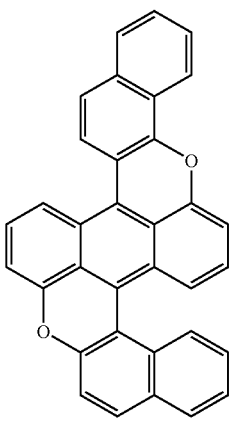
No. 88
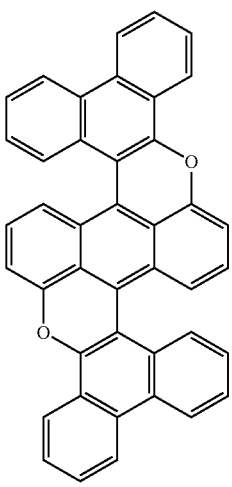

No. 89
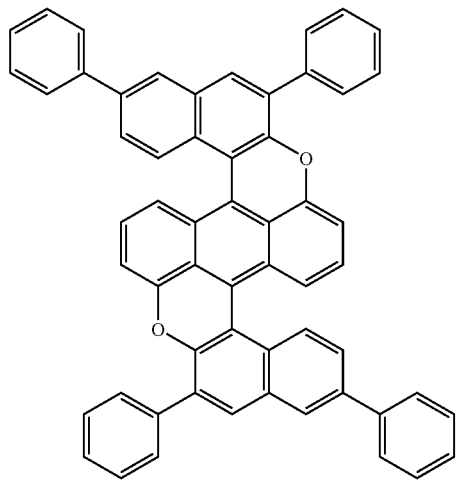
No. 90
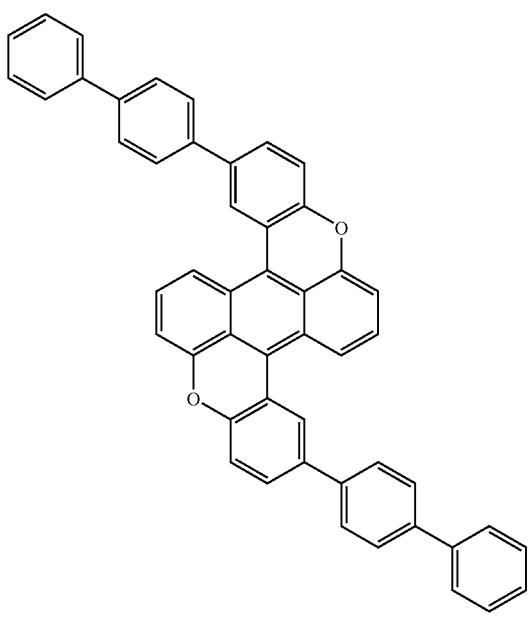
No. 91
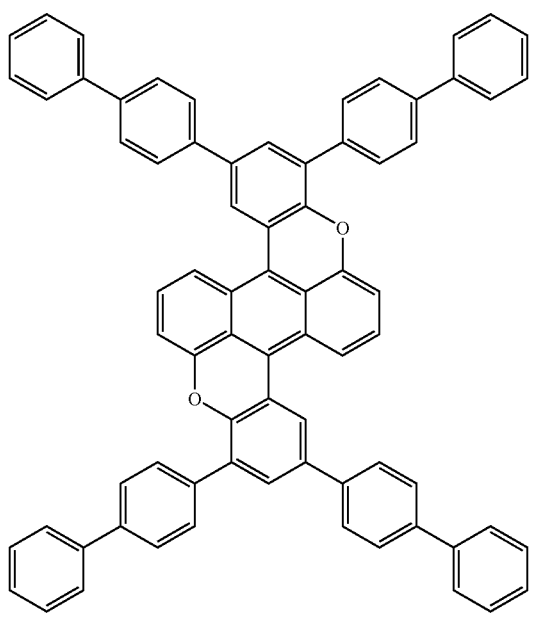
No. 92
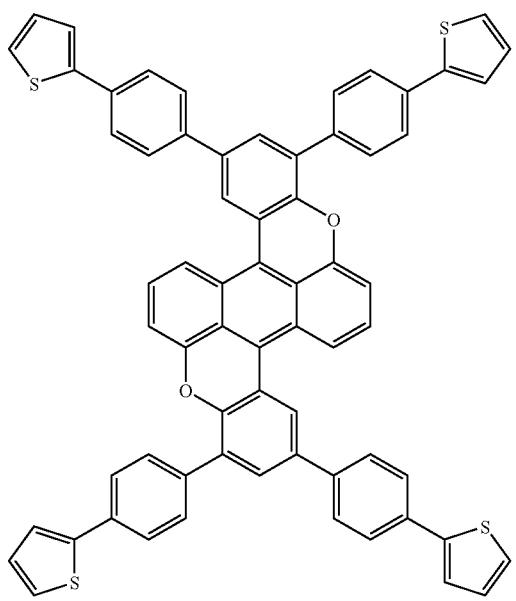

-continued
No. 93
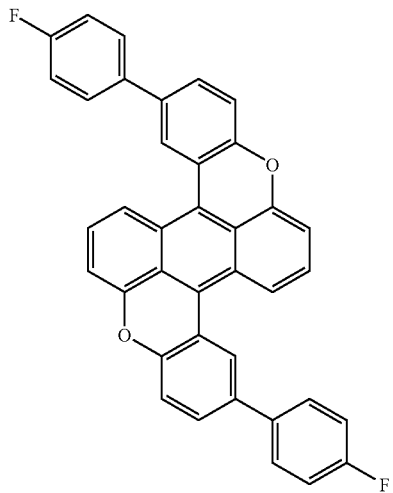
No. 94
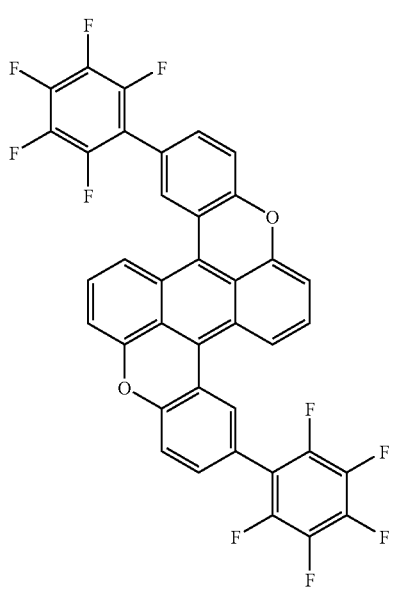
No. 95
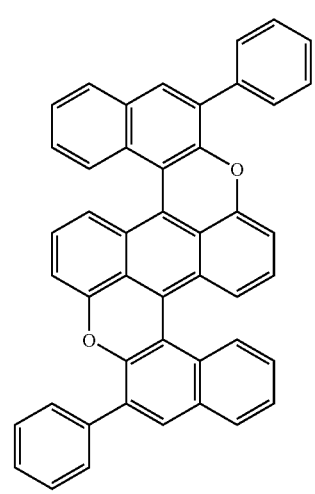
-continued
No. 96
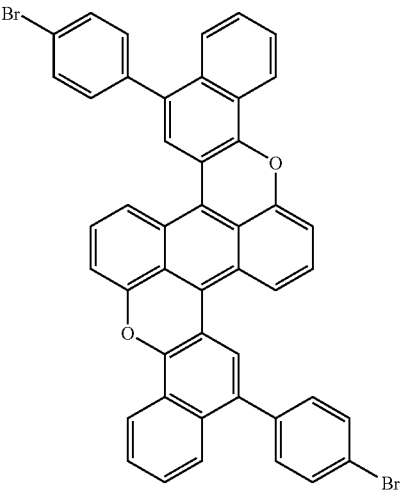
No. 97
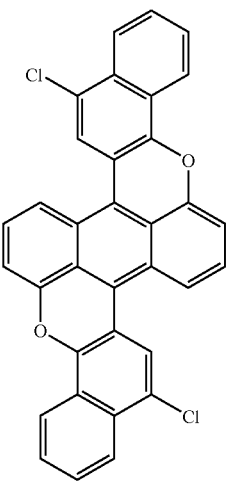
No. 98

No. 99
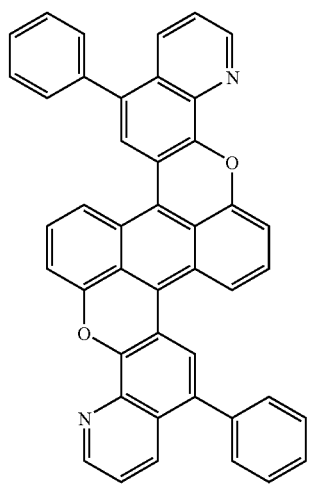
No. 100
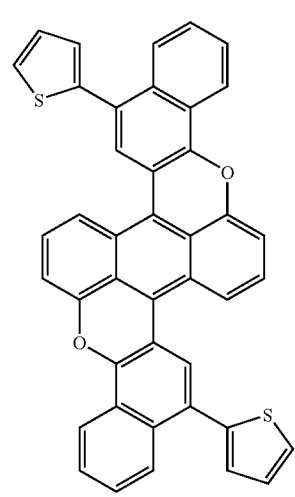
No. 101
No. 102
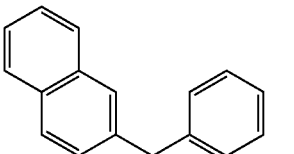
No. 103
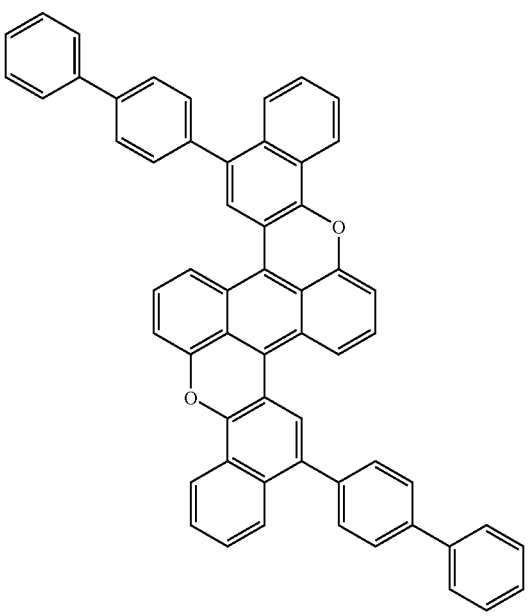

-continued
No. 104
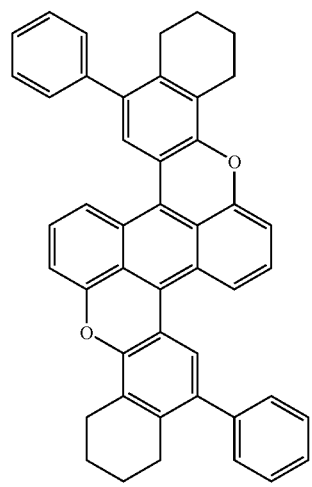
No. 105
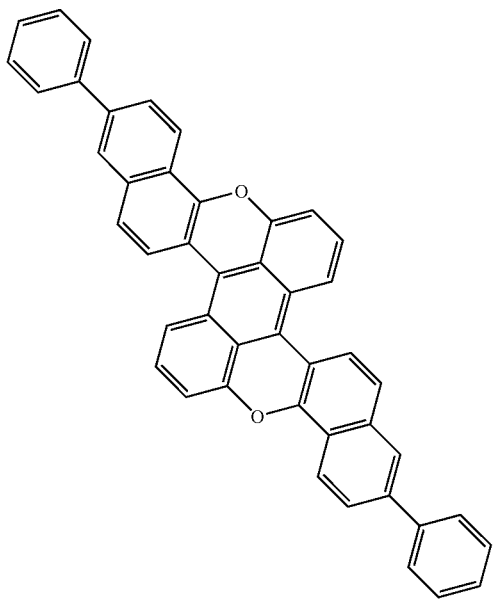
No. 106
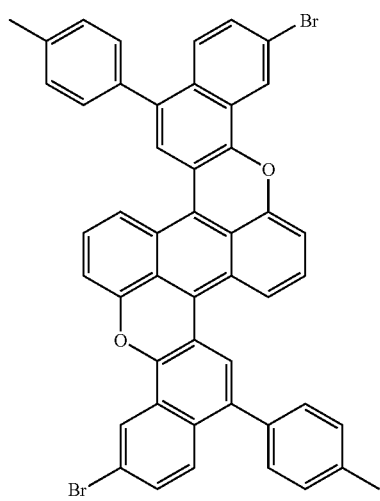
-continued
No. 107
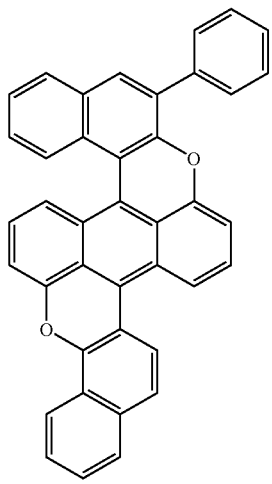
No. 108
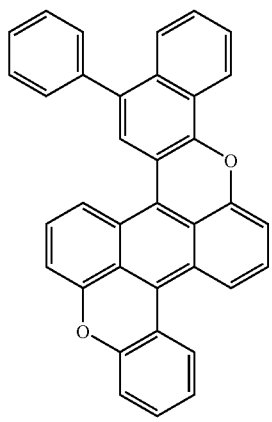
No. 109
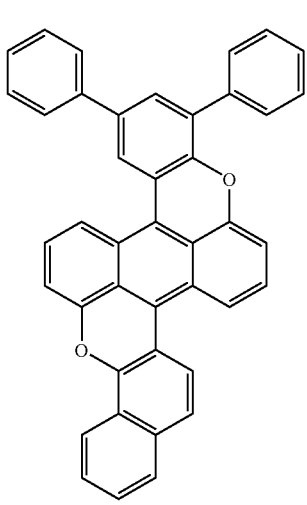

-continued
No. 110
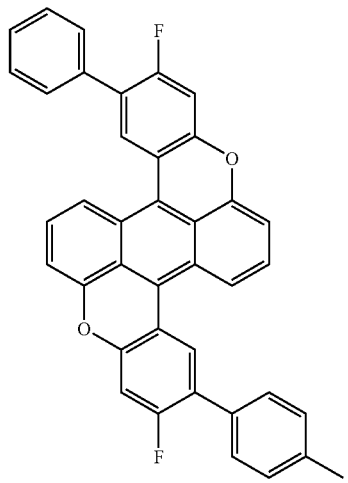
No. 111
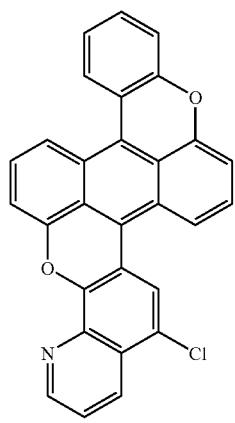
No. 112
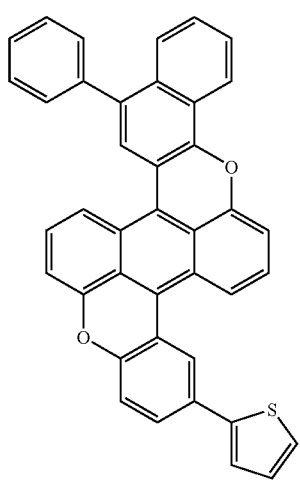
-continued
No. 113
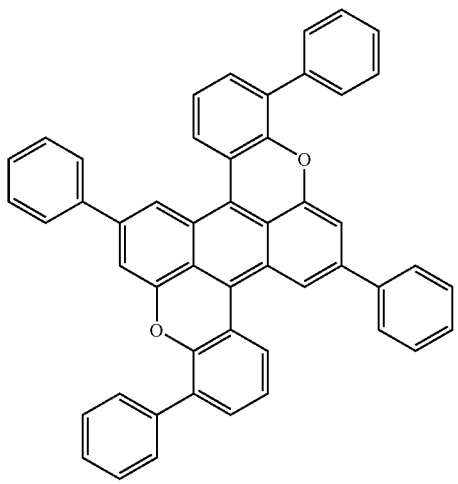
No. 114
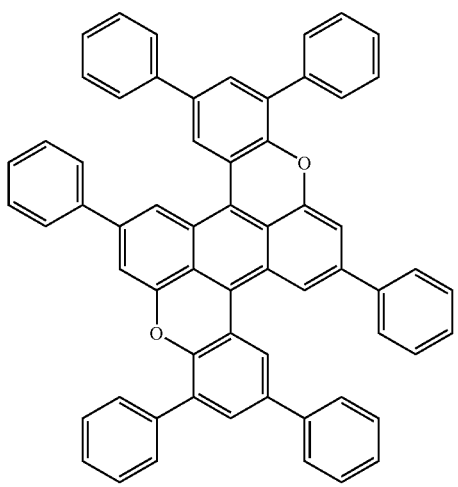
No. 115
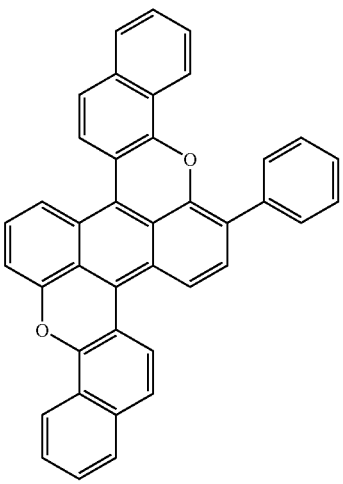

-continued
No. 116
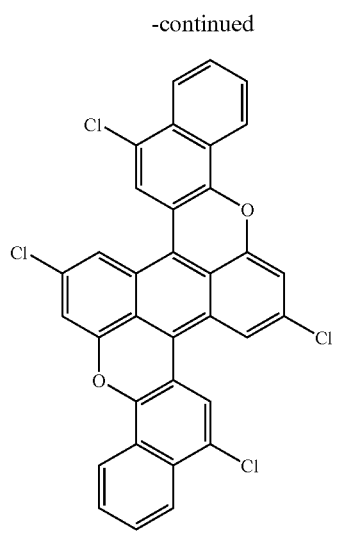
No. 117
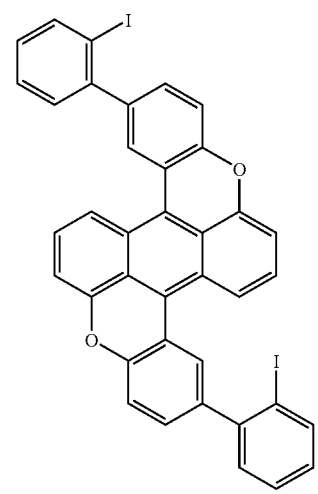
No. 118
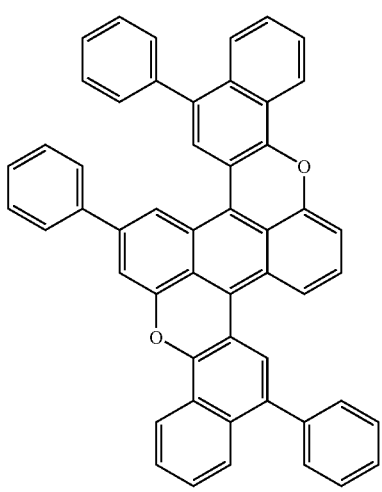
-continued
No. 119
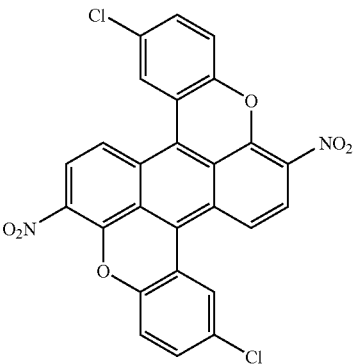
No. 120
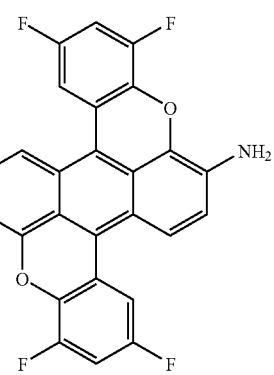
No. 121
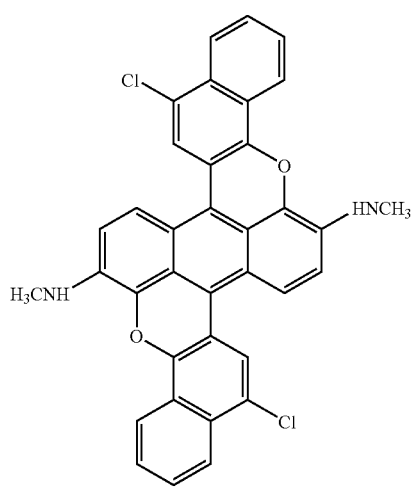

No. 122
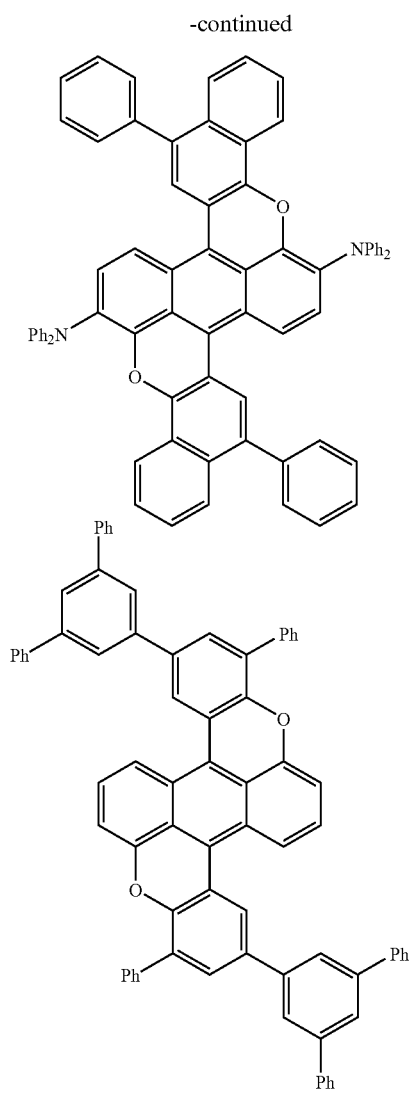
No. 123
No. 124
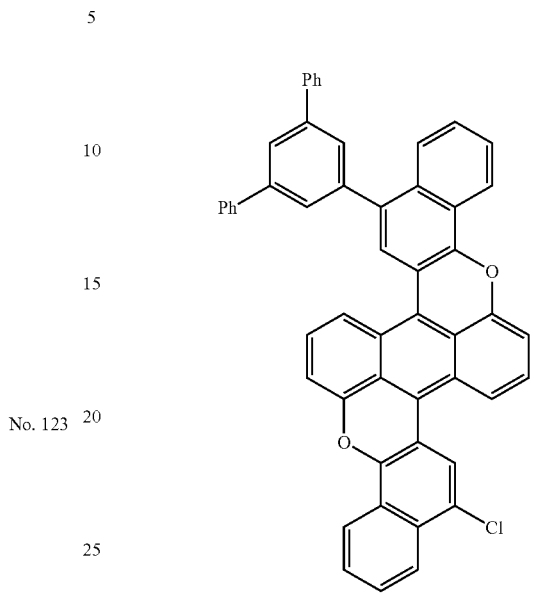
Hereinafter, examples of the compounds represented by Formula (18), i.e., the compounds represented by Formula (3) wherein each of $R_5$ to $R_7$ and $R_{12}$ to $R_{14}$ is a hydrogen atom and $X_1$ and $X_2$ are sulfur atoms are listed in Table 2. The abbreviations in Table 2 are the same as those in Table 1.
TABLE 2
(18)
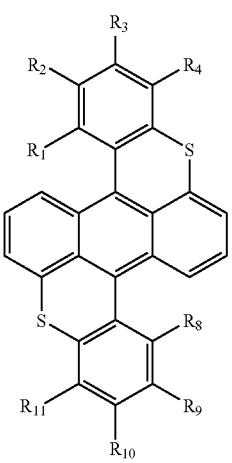
| Compound NO. | $R_1$ | $R_2$ | $R_3$ | $R_4$ | $R_8$ | $R_9$ | $R_{10}$ | $R_{11}$ |
|---|---|---|---|---|---|---|---|---|
| 125 | H | H | H | H | H | H | H | H |
| 126 | H | CH$_3$ | H | H | H | CH$_3$ | H | H |

TABLE 2-continued (18)

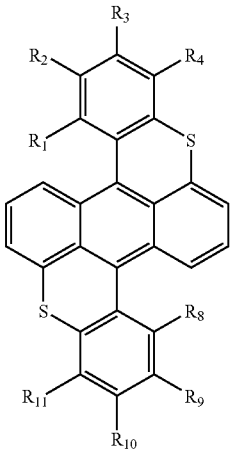

| Compound NO. | $R_1$ | $R_2$ | $R_3$ | $R_4$ | $R_8$ | $R_9$ | $R_{10}$ | $R_{11}$ |
|---|---|---|---|---|---|---|---|---|
| 127 | H | $C_2H_5$ | H | H | H | $C_2H_5$ | H | H |
| 128 | H | $CH_3$ | H | $CH_3$ | H | $CH_3$ | H | $CH_3$ |
| 129 | H | H | H | $CH_3$ | H | H | H | $CH_3$ |
| 130 | $CH3$ | H | $CH_3$ | H | $CH_3$ | H | $CH_3$ | H |
| 131 | H | $t-C_4H_9$ | H | H | H | $t-C_4H_9$ | H | H |
| 132 | H | $CH_3$ | H | H | H | H | H | H |
| 133 | H | Ph | H | H | H | Ph | H | H |
| 134 | H | H | H | Ph | H | H | H | Ph |
| 135 | H | H | Ph | H | H | H | Ph | H |
| 136 | H | Np | H | H | H | Np | H | H |
| 137 | H | H | H | Np | H | H | H | Np |
| 138 | H | H | $t-C_4H_9$ | H | H | H | $t-C_4H_9$ | H |
| 139 | H | OPh | H | H | H | OPh | H | H |
| 140 | H | H | OPh | H | H | H | OPh | H |
| 141 | H | $OCH_3$ | H | H | H | $OCH_3$ | H | H |
| 142 | H | H | $OCH_3$ | H | H | H | $OCH_3$ | H |
| 143 | H | Th | H | H | H | Th | H | H |
| 144 | H | Py | H | H | H | Py | H | H |
| 145 | H | $CH_3$ | H | H | H | Cy | H | H |
| 146 | H | $CH_3$ | H | H | H | Ph | H | H |
| 147 | Ph | H | H | H | H | H | Ph | H |
| 148 | H | Py | H | H | H | H | H | H |
| 149 | H | Cl | H | H | H | Cl | H | H |
| 150 | H | I | H | H | H | I | H | H |
| 151 | H | CN | H | H | H | CN | H | H |
| 152 | H | H | $NO_2$ | H | H | H | $NO_2$ | H |
| 153 | H | H | OH | H | H | H | OH | H |
| 154 | H | $N(CH_3)_2$ | H | H | H | $N(CH_3)_2$ | H | H |
| 155 | H | COOH | H | H | H | H | H | H |
| 156 | H | CHO | H | H | H | H | H | H |
| 157 | H | $COOCH_3$ | H | H | H | $COOCH_3$ | H | H |
| 158 | H | 4MPh | H | H | H | 4MPh | H | H |
| 159 | $CH_3$ | $CH_3$ | $CH_3$ | H | $CH_3$ | $CH_3$ | $CH_3$ | H |
| 160 | H | COPh | H | H | H | COPh | H | H |
| 161 | H | COOPh | H | H | H | COOPh | H | H |
| 162 | F | F | F | H | F | F | F | H |
| 163 | H | Ph | H | Ph | H | Ph | H | Ph |
| 164 | H | F | H | H | H | F | H | H |
| 165 | H | F | H | F | H | F | H | F |
| 166 | F | H | F | H | F | H | F | H |
| 167 | H | Br | H | H | H | Br | H | H |
| 168 | H | H | H | Br | H | H | H | Br |
| 169 | H | Br | H | Br | H | Br | H | Br |
| 170 | H | Br | H | F | H | Br | H | F |
| 171 | H | $CF_3$ | H | H | H | $CF_3$ | H | H |
| 172 | H | $CF_3$ | H | $CF_3$ | H | $CF_3$ | H | $CF_3$ |
| 173 | H | H | $C_2F_5$ | H | H | H | $C_2F_5$ | H |
| 174 | $CF_3$ | H | $CF_3$ | H | $CF_3$ | H | $CF_3$ | H |

Examples of other compounds represented by Formula (18) ($X_1$ and $X_2$ are sulfur atoms) are listed below.
No. 175
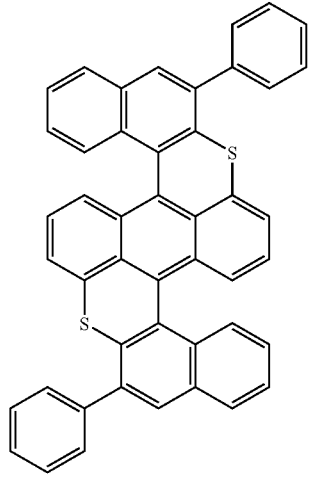
No. 176
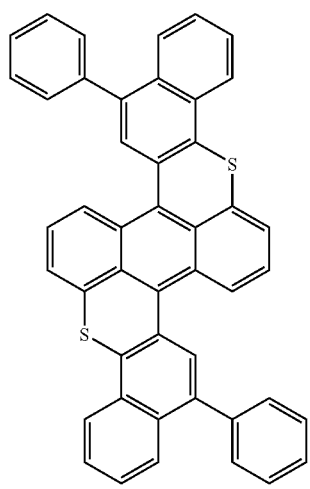
No. 177
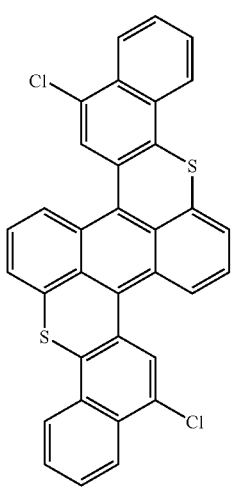
No. 178
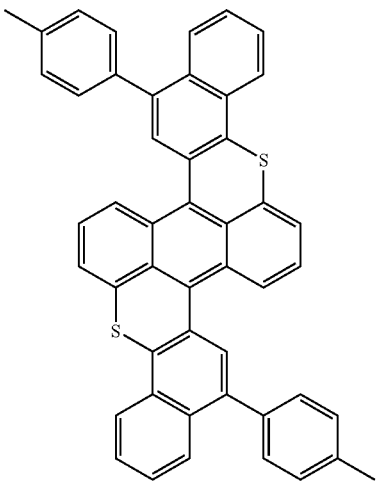
No. 179
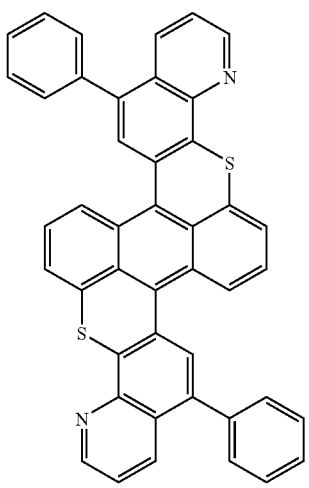
No. 180
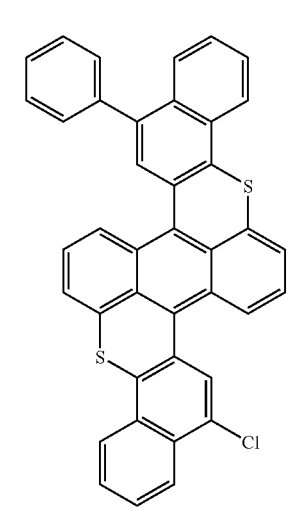

-continued
No. 181
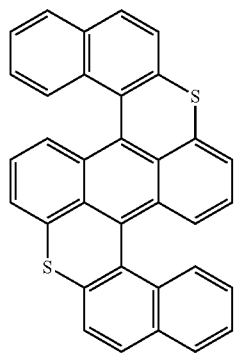
No. 182
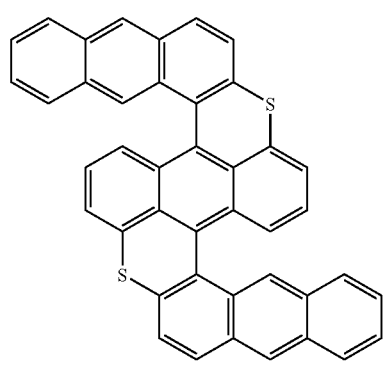
No. 183
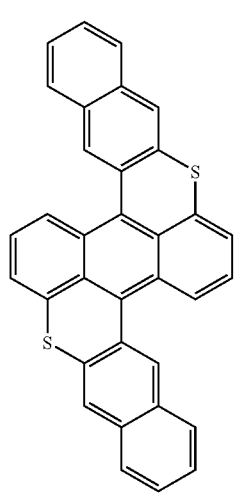
-continued
No. 184
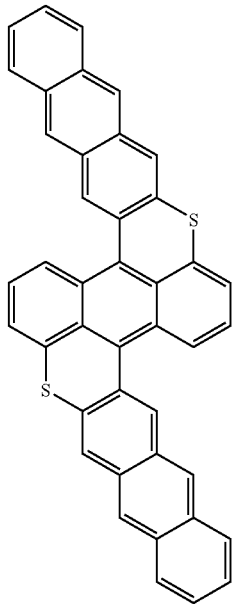
No. 185
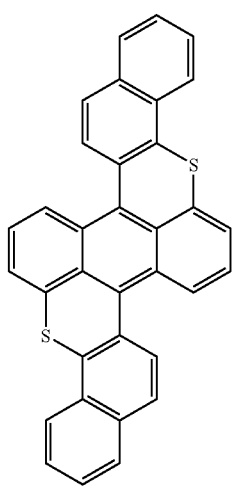

-continued
No. 186
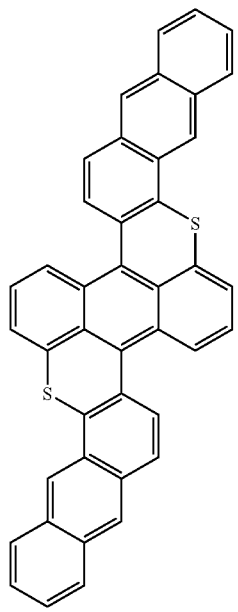
No. 187
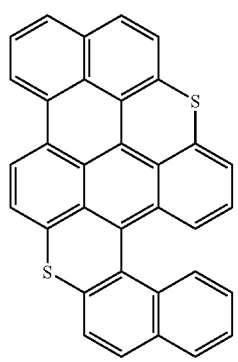
No. 188
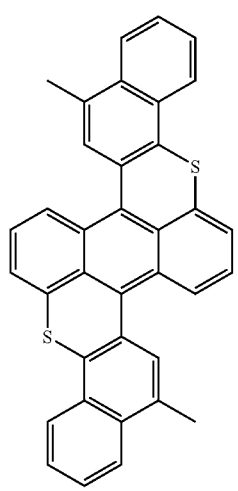
-continued
No. 189
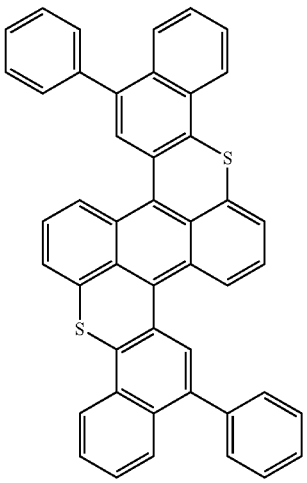
No. 190
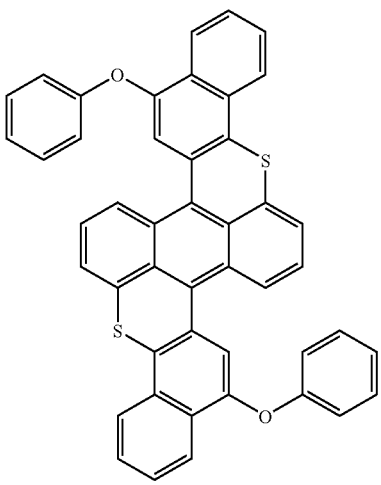
No. 191
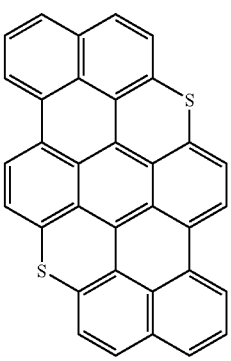

No. 192
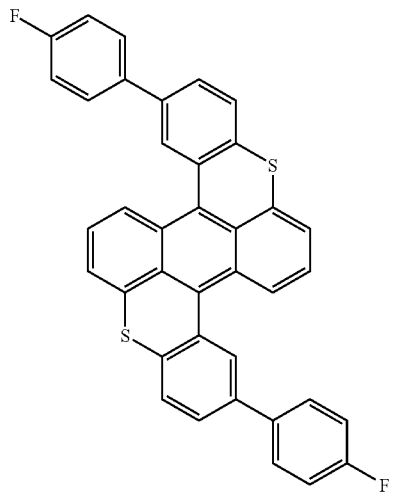
No. 193
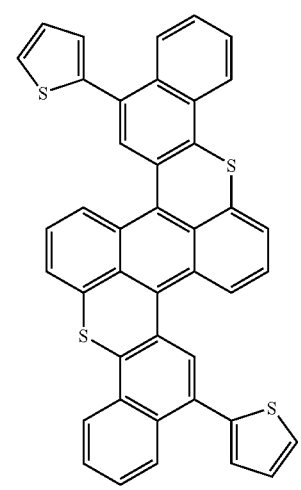
No. 194
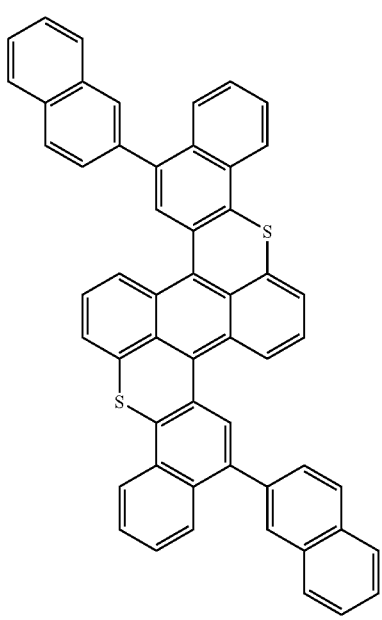
No. 195
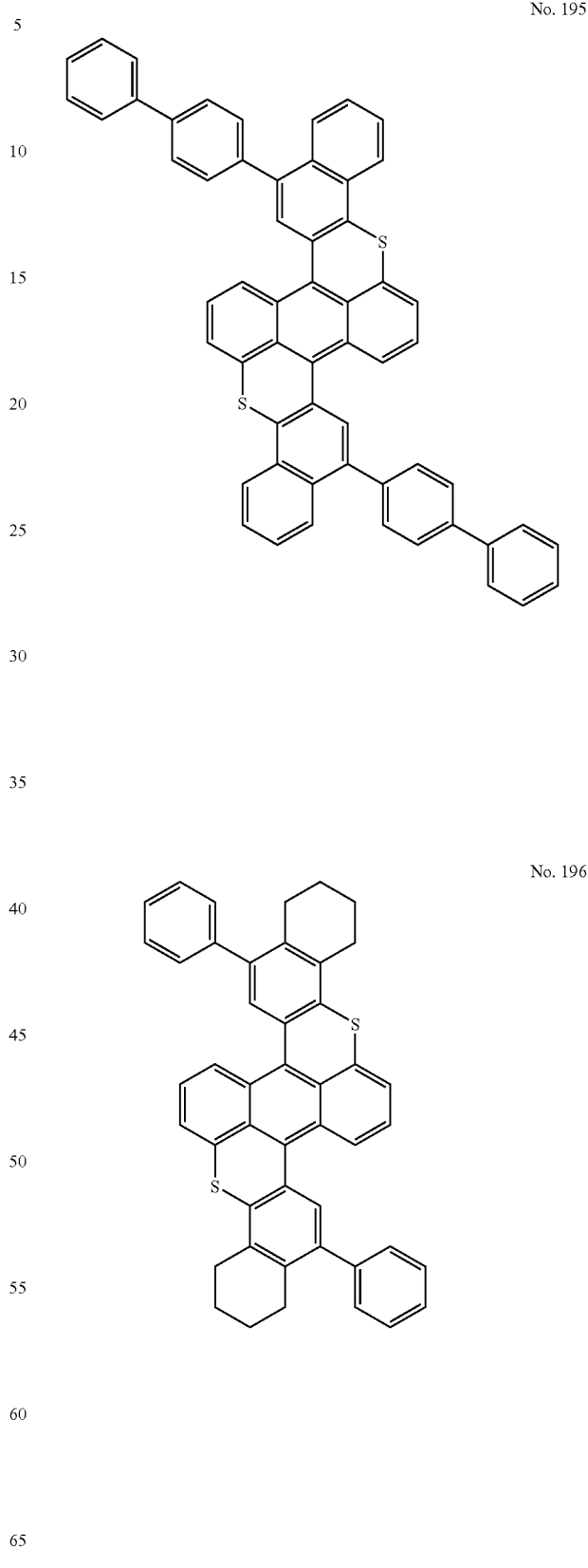
No. 196

-continued
No. 197
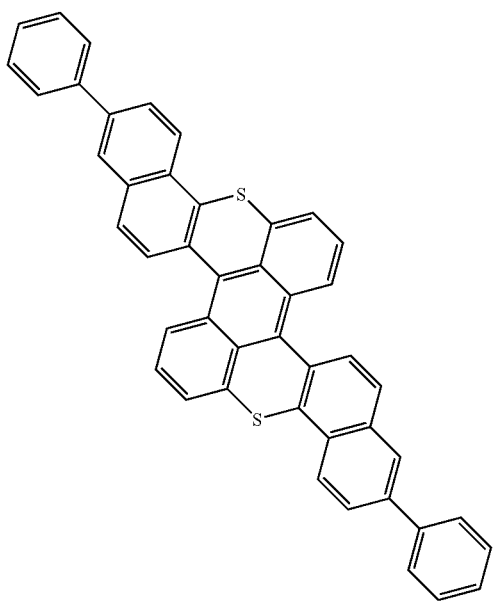
No. 198
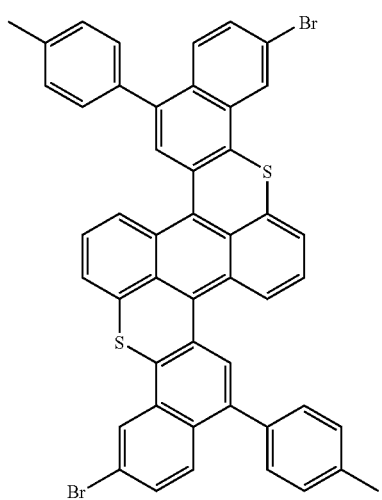
No. 199
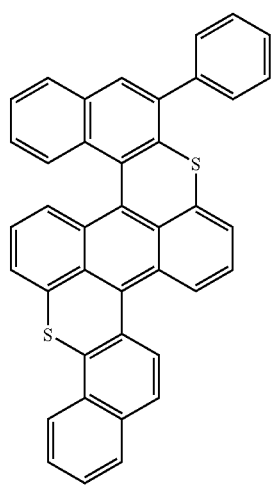
-continued
No. 200
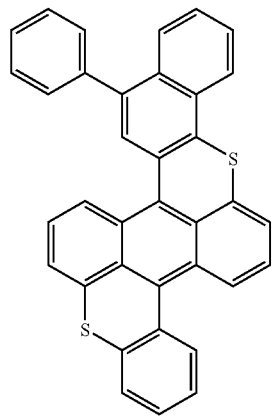
No. 201
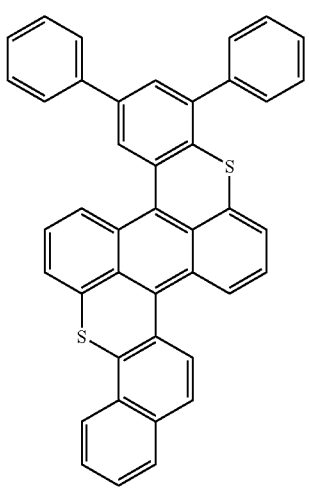
No. 202
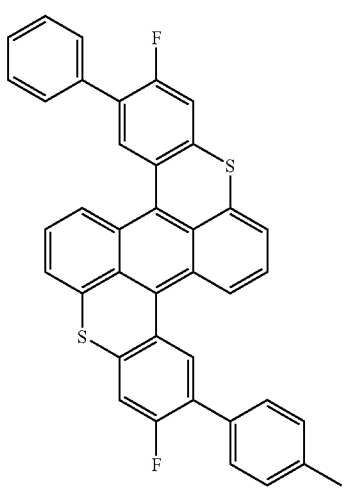

-continued
No. 203
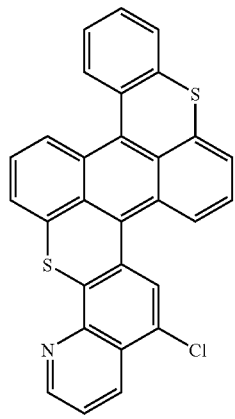
No. 206
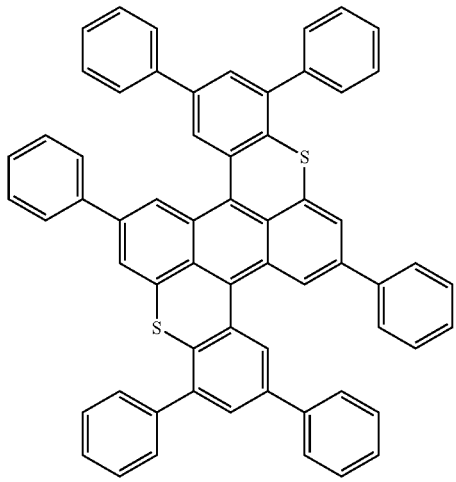
No. 204
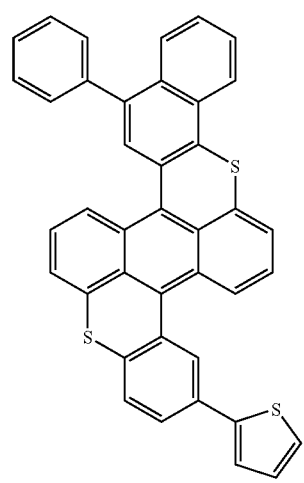
No. 207
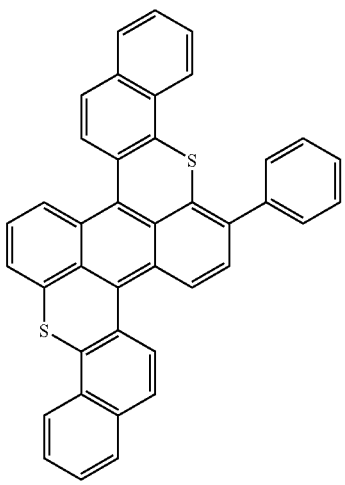
No. 205
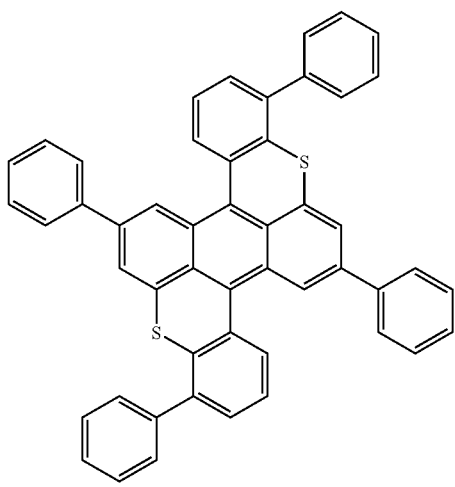
No. 208
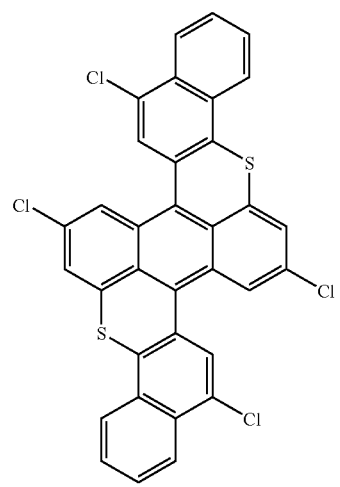

-continued
No. 209
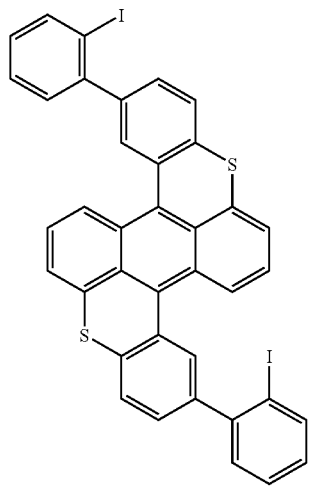
No. 210
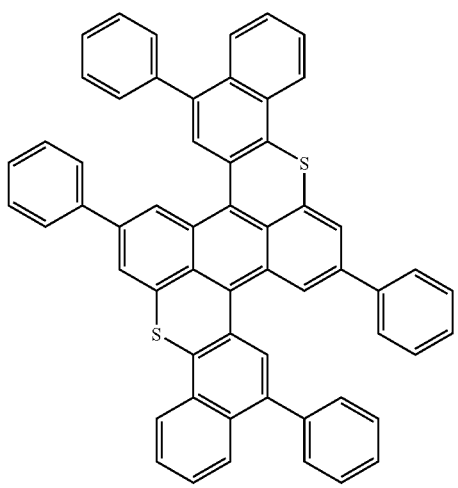
No. 211
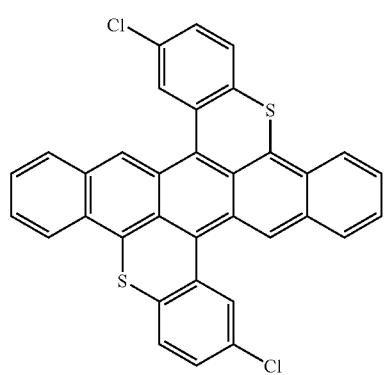
-continued
No. 212
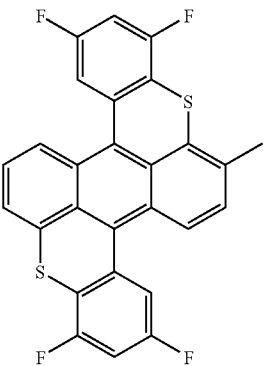
No. 213
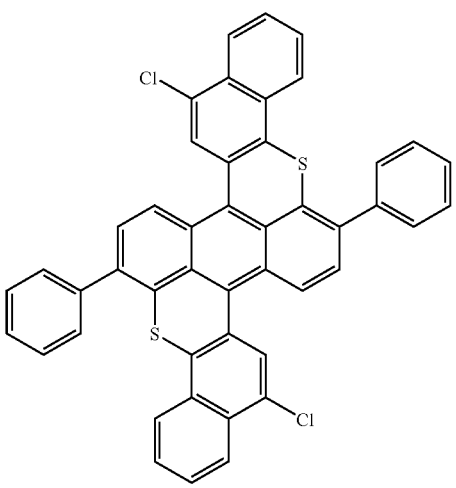
No. 214
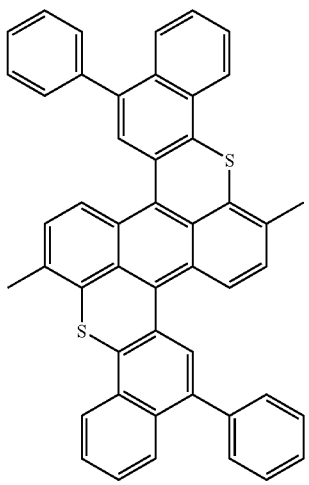

-continued
No. 215
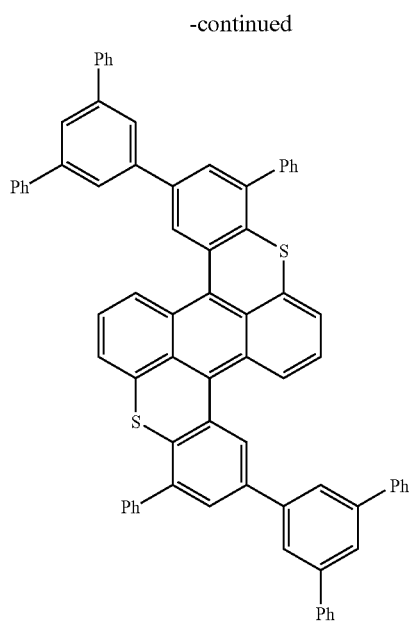
No. 216
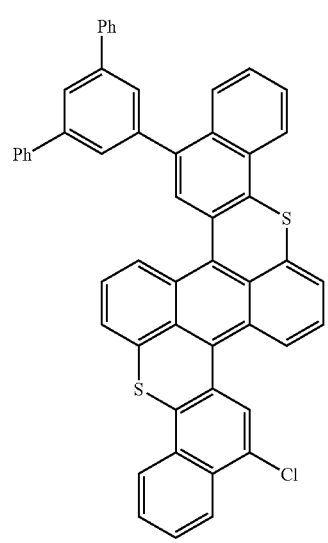
No. 217
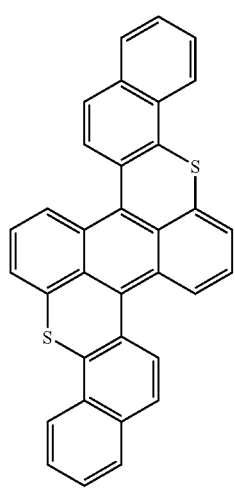
-continued
No. 218
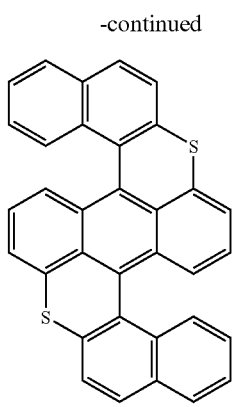
No. 219
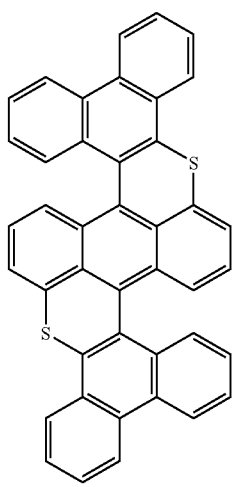
No. 220
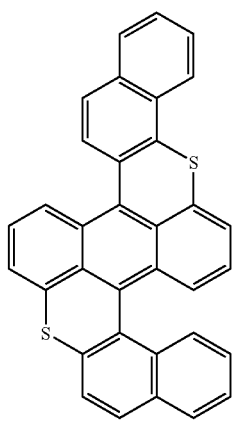

-continued

No. 221
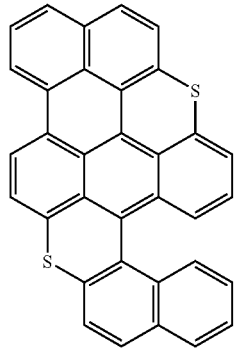

No. 222
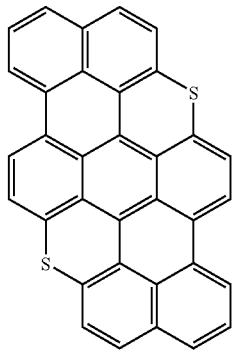

Hereinafter, examples of the compounds represented by Formula (19), i.e., the compounds represented by Formula (3) wherein each of $R_5$ to $R_7$ and $R_{12}$ to $R_{14}$ is a hydrogen atom and $X_1$ and $X_2$ are selenium atoms, are listed in Table 3. The abbreviations in Table 3 are the same as those in Table 1.

TABLE 3

(19)

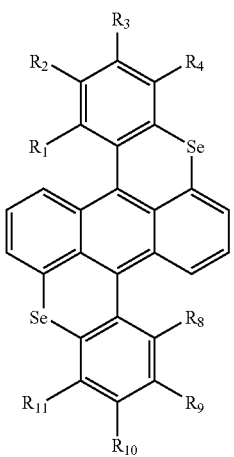

| Compound No. | $R_1$ | $R_2$ | $R_3$ | $R_4$ | $R_8$ | $R_9$ | $R_{10}$ | $R_{11}$ |
|---|---|---|---|---|---|---|---|---|
| 223 | H | H | H | H | H | H | H | H |
| 224 | H | CH$_3$ | H | H | H | CH$_3$ | H | H |
| 225 | H | C$_2$H$_5$ | H | H | H | C$_2$H$_5$ | H | H |
| 226 | H | CH$_3$ | H | CH$_3$ | H | CH$_3$ | H | CH$_3$ |
| 227 | H | H | C$_2$H$_5$ | H | H | H | C$_2$H$_5$ | H |
| 228 | CH3 | H | CH$_3$ | H | CH$_3$ | H | CH$_3$ | H |
| 229 | H | t-C$_4$H$_9$ | OH | H | H | t-C$_4$H$_9$ | H | H |
| 230 | H | CH$_3$ | H | H | H | H | H | H |
| 231 | H | Ph | H | H | H | Ph | H | H |
| 232 | H | H | H | Ph | H | H | H | Ph |
| 233 | H | H | Ph | H | H | H | Ph | H |
| 234 | H | Np | H | H | H | Np | H | H |
| 235 | H | H | H | Np | H | H | H | Np |
| 236 | H | H | t-C$_4$H$_9$ | H | H | H | t-C$_4$H$_9$ | H |

TABLE 3-continued

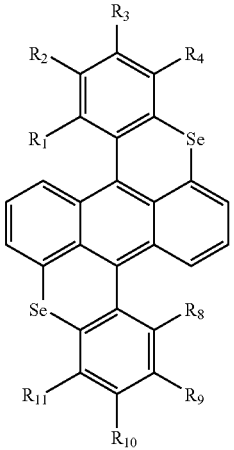

(19)

| Compound No. | $R_1$ | $R_2$ | $R_3$ | $R_4$ | $R_8$ | $R_9$ | $R_{10}$ | $R_{11}$ |
|---|---|---|---|---|---|---|---|---|
| 237 | H | OPh | H | H | H | OPh | H | H |
| 238 | H | H | OPh | H | H | H | OPh | H |
| 239 | H | $OCH_3$ | H | H | H | $OCH_3$ | H | H |
| 240 | H | H | $OCH_3$ | H | H | H | $OCH_3$ | H |
| 241 | H | Th | H | H | H | Th | H | H |
| 242 | H | Py | H | H | H | Py | H | H |
| 243 | H | $CH_3$ | H | H | H | Cy | H | H |
| 244 | H | $CH_3$ | H | H | H | Ph | H | H |
| 245 | Ph | H | H | H | H | H | Ph | H |
| 246 | H | Py | H | H | H | H | H | H |
| 247 | H | Cl | H | H | H | Cl | H | H |
| 248 | H | I | H | H | H | I | H | H |
| 249 | H | CN | H | H | H | CN | H | H |
| 250 | H | H | $NO_2$ | H | H | H | $NO_2$ | H |
| 251 | H | H | OH | H | H | H | OH | H |
| 252 | H | $N(CH_3)_2$ | H | H | H | $N(CH_3)_2$ | H | H |
| 253 | H | COOH | H | H | H | H | H | H |
| 254 | H | CHO | H | H | H | H | H | H |
| 255 | H | $COOCH_3$ | H | H | H | $COOCH_3$ | H | H |
| 256 | H | 4MPh | H | H | H | 4MPh | H | H |
| 257 | $CH_3$ | $CH_3$ | $CH_3$ | H | $CH_3$ | $CH_3$ | $CH_3$ | H |
| 258 | H | COPh | H | H | H | COPh | H | H |
| 259 | H | COOPh | H | H | H | COOPh | H | H |
| 260 | F | F | F | H | F | F | F | H |
| 261 | H | Ph | H | Ph | H | Ph | H | Ph |
| 262 | H | F | H | H | H | F | H | H |
| 263 | H | F | H | F | H | F | H | F |
| 264 | F | H | F | H | F | H | F | H |
| 265 | H | Br | H | H | H | Br | H | H |
| 266 | H | $CF_3$ | H | H | H | $CF_3$ | H | H |
| 267 | H | $CF_3$ | H | $CF_3$ | H | $CF_3$ | H | $CF_3$ |
| 268 | H | H | $C_2F_5$ | H | H | H | $C_2F_5$ | H |
| 269 | $CF_3$ | H | $CF_3$ | H | $CF_3$ | H | $CF_3$ | H |

Hereinafter, examples of compounds represented by the following Formula (20), i.e., the compounds represented by Formula (3) wherein each of $R_5$ to $R_7$ and $R_{12}$ to $R_{14}$ is a hydrogen atom and $X_1$ and $X_2$ each is $NR_{29}$, are listed in Table 4. Two $NR_{29}$ groups in Formula (3) are indicated respectively by $NR_{30}$ and $NR_{31}$ in Formula (20). In the Table, 4MePh indicates a 4-methylphenyl group; 4PhPh, 4-phenylphenyl; 2PhPh, 2-phenylphenyl; and t-Bu, t-butyl.

TABLE 4

(20)

[Structure with substituents R1, R2, R3, R4, R8, R9, R10, R11, R30, R31]

| Compound No. | R1 | R2 | R3 | R4 | R8 | R9 | R10 | R11 | R30 | R31 |
|---|---|---|---|---|---|---|---|---|---|---|
| 270 | H | H | H | H | H | H | H | H | H | H |
| 271 | H | CH3 | H | H | H | CH3 | H | H | CH3 | CH3 |
| 272 | H | CH3 | H | H | H | CH3 | H | H | H | H |
| 273 | H | H | H | H | H | H | H | H | CH3 | CH3 |
| 274 | H | H | H | H | H | H | H | H | CH2Br | CH2Br |
| 275 | H | CH3 | H | H | H | CH3 | H | H | CH2Ph | CH2Ph |
| 276 | H | H | H | H | H | H | H | H | Ph | Ph |
| 277 | H | CH3 | H | H | H | CH3 | H | H | 4MePh | 4MePh |
| 278 | H | Ph | H | H | H | Ph | H | H | CH3 | CH3 |
| 279 | H | Ph | H | H | H | Ph | H | H | 4PhPh | 4PhPh |
| 280 | H | H | H | Ph | H | H | H | Ph | 2PhPh | 2PhPh |
| 281 | H | H | H | H | H | H | H | H | Ph | H |
| 282 | H | H | H | H | H | H | H | H | Ph | CH3 |
| 283 | H | H | H | H | H | H | H | H | t-Bu | t-Bu |
| 284 | H | Ph | H | H | H | H | H | H | Ph | H |
| 285 | H | Ph | H | Ph | H | Ph | H | Ph | Ph | Ph |
| 286 | H | F | H | H | H | F | H | H | Ph | Ph |
| 287 | H | F | H | F | H | F | H | F | H | H |
| 288 | F | H | F | H | F | H | F | H | Ph | Ph |
| 289 | H | Br | H | H | H | Br | H | H | Ph | Ph |
| 290 | H | CF3 | H | H | H | CF3 | H | H | Ph | Ph |
| 291 | H | CF3 | H | CF3 | H | CF3 | H | CF3 | Ph | Ph |
| 292 | H | H | C2F5 | H | H | H | C2F5 | H | Ph | Ph |
| 293 | CF3 | H | CF3 | H | CF3 | H | CF3 | H | Ph | Ph |

Examples of the other compounds represented by Formula (3) are listed below.

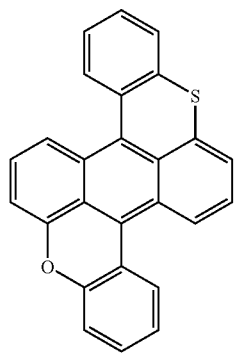

No. 294

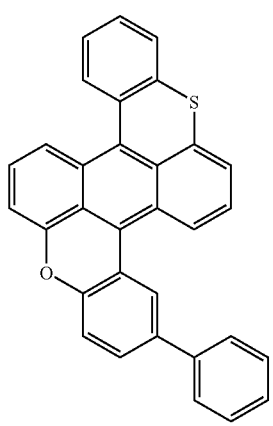

No. 295

-continued

No. 296

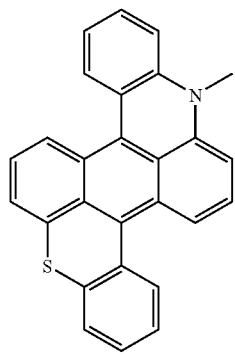

No. 297

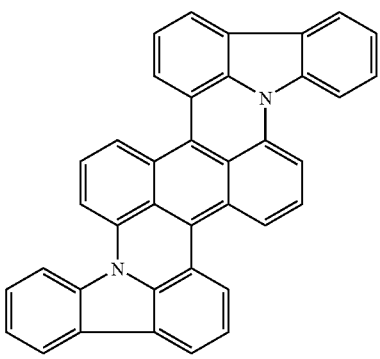

No. 298

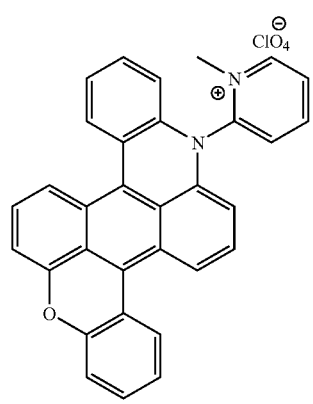

No. 299

-continued

No. 300

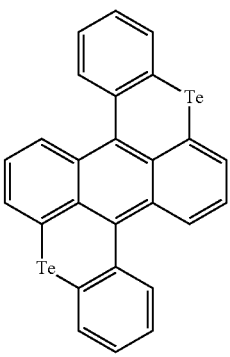

No. 301

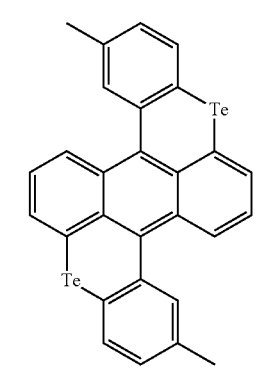

No. 302

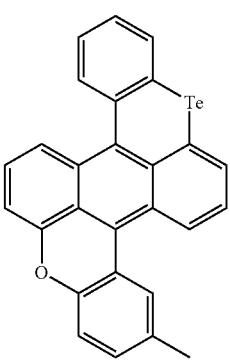

Hereinafter, favorable examples of the compounds represented by Formula (4) include the compound represented by the following Formula: First, examples of the compounds represented by Formula (21), wherein each of $R_{19}$ to $R_{20}$ and $R_{25}$ to $R_{28}$ is a hydrogen atom and $X_3$ and $X_4$ are oxygen atoms, are listed in Table 5. In the Table, a phenyl group is designated as Ph; 4-methylphenyl, MPh; naphthyl, Np; 2-thienyl, Th; 2-pyridyl, Py; and cyclohexyl group, Cy.

TABLE 5

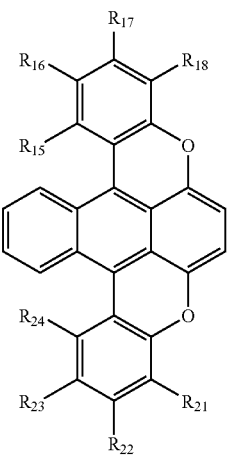

(21)

| Compound No. | R15 | R16 | R17 | R18 | R24 | R23 | R22 | R21 |
|---|---|---|---|---|---|---|---|---|
| 303 | H | H | H | H | H | H | H | H |
| 304 | H | CH3 | H | H | H | CH3 | H | H |
| 305 | H | C2H5 | H | H | H | C2H5 | H | H |
| 306 | H | CH3 | H | CH3 | H | CH3 | H | CH3 |
| 307 | H | H | C2H5 | H | H | H | C2H5 | H |
| 308 | CH3 | H | CH3 | H | CH3 | H | CH3 | H |
| 309 | H | t-C4H9 | H | H | H | t-C4H9 | H | H |
| 310 | H | CH3 | H | H | H | H | H | H |
| 311 | H | Ph | H | H | H | Ph | H | H |
| 312 | H | H | H | Ph | H | H | H | Ph |
| 313 | H | H | Ph | H | H | H | Ph | H |
| 314 | H | Np | H | H | H | Np | H | H |
| 315 | H | H | H | Np | H | H | H | Np |
| 316 | H | H | t-C4H9 | H | H | H | t-C4H9 | H |
| 317 | H | OPh | H | H | H | OPh | H | H |
| 318 | H | H | OPh | H | H | H | OPh | H |
| 319 | H | OCH3 | H | H | H | OCH3 | H | H |
| 320 | H | H | OCH3 | H | H | H | OCH3 | H |
| 321 | H | Th | H | H | H | Th | H | H |
| 322 | H | Py | H | H | H | Py | H | H |
| 323 | H | CH3 | H | H | H | Cy | H | H |
| 324 | H | CH3 | H | H | H | Ph | H | H |
| 325 | Ph | H | H | H | H | H | Ph | H |
| 326 | H | Py | H | H | H | H | H | H |
| 327 | H | Cl | H | H | H | Cl | H | H |
| 328 | H | I | H | H | H | I | H | H |
| 329 | H | CN | H | H | H | CN | H | H |
| 330 | H | H | NO2 | H | H | H | NO2 | H |
| 331 | H | H | OH | H | H | H | OH | H |
| 332 | H | N(CH3)2 | H | H | H | N(CH3)2 | H | H |
| 333 | H | COOH | H | H | H | H | H | H |
| 334 | H | CHO | H | H | H | H | H | H |
| 335 | H | COOCH3 | H | H | H | COOCH3 | H | H |
| 336 | H | MPh | H | H | H | MPh | H | H |
| 337 | CH3 | CH3 | CH3 | H | CH3 | CH3 | CH3 | H |
| 338 | H | COPh | H | H | H | COPh | H | H |
| 339 | H | COOPh | H | H | H | COOPh | H | H |
| 340 | F | F | F | F | F | F | F | H |
| 341 | H | Ph | H | Ph | H | Ph | H | Ph |
| 342 | H | F | H | H | H | F | H | H |
| 343 | H | F | H | F | H | F | H | F |
| 344 | F | H | F | H | F | H | F | H |
| 345 | H | Br | H | H | H | Br | H | H |
| 346 | H | CF3 | H | H | H | CF3 | H | H |
| 347 | H | CF3 | H | CF3 | H | CF3 | H | CF3 |
| 348 | H | H | C2F5 | H | H | H | C2F5 | H |
| 349 | CF3 | H | CF3 | H | CF3 | H | CF3 | H |
| 350 | H | Br | H | Br | H | Br | H | Br |
| 351 | H | H | H | Br | H | H | H | Br |

Examples of other compounds represented by Formula (21) ($X_3$ and $X_4$ are oxygen atoms) are listed below.
No. 352
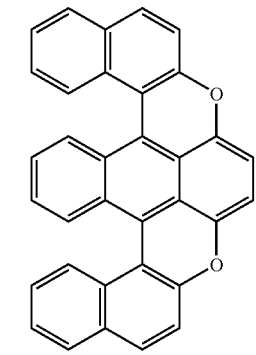
No. 353
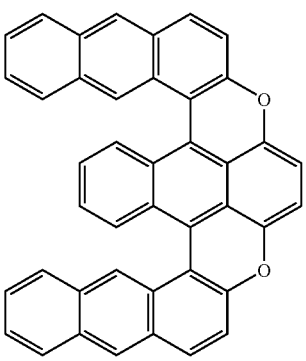
No. 354
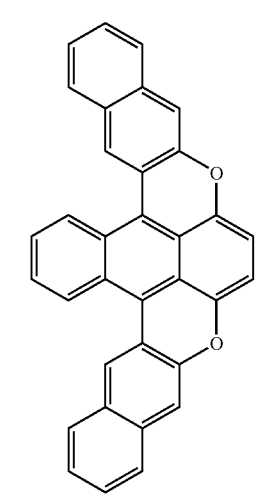
No. 355
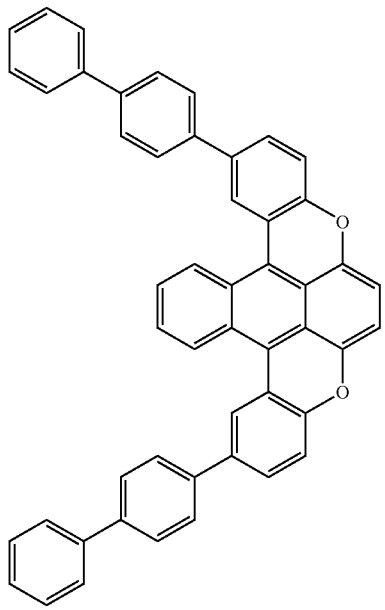
No. 356
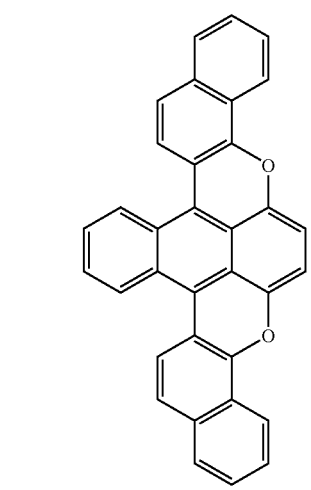

-continued
No. 357
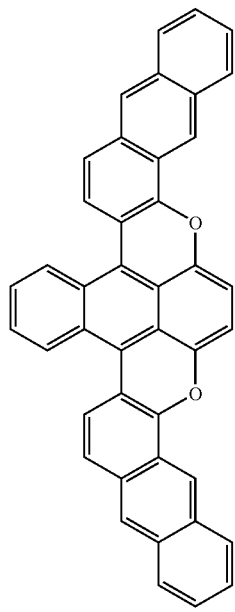
No. 358
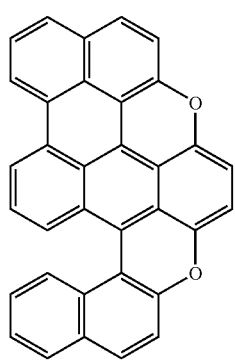
No. 359
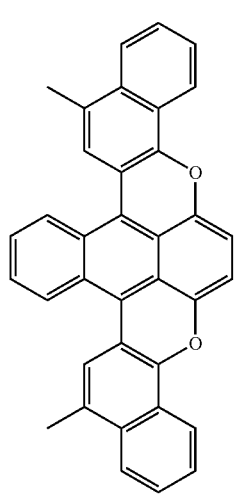
-continued
No. 360
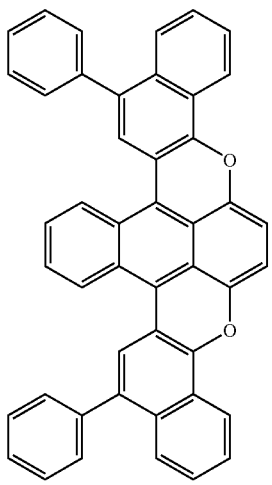
No. 361
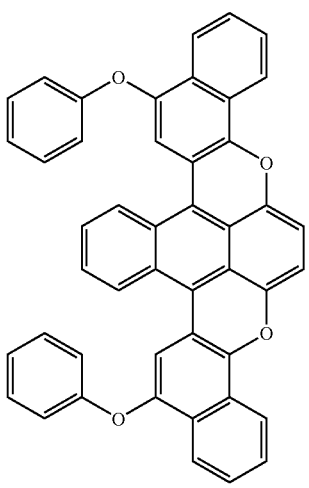
No. 362
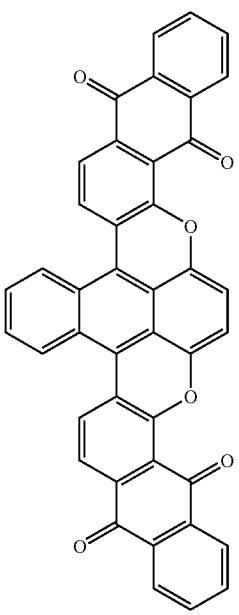

No. 363
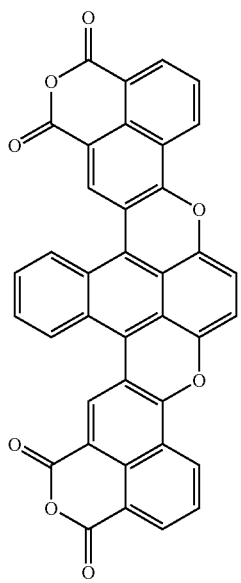
No. 364
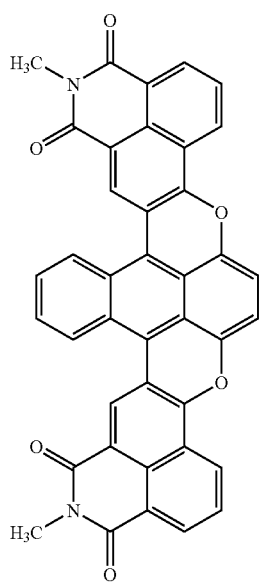
No. 365
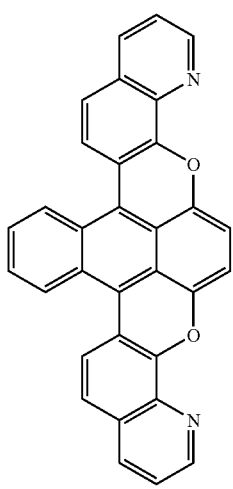
No. 366
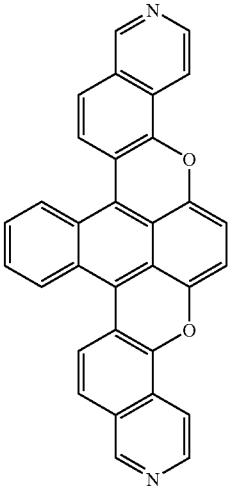
No. 367
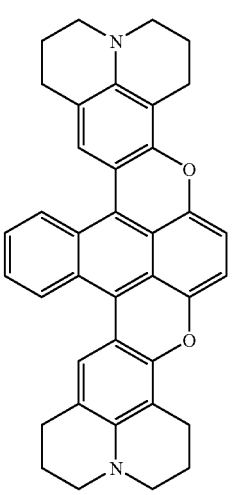
No. 368
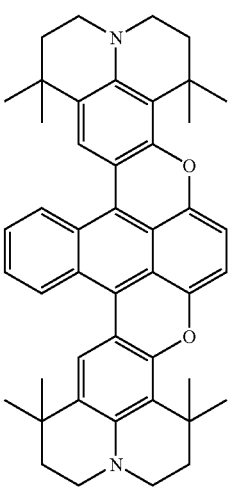

No. 369
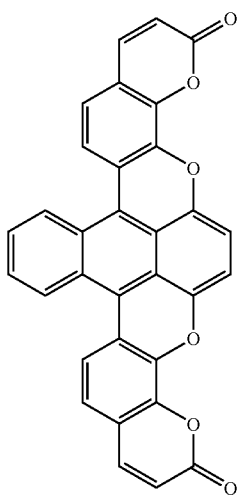
No. 370
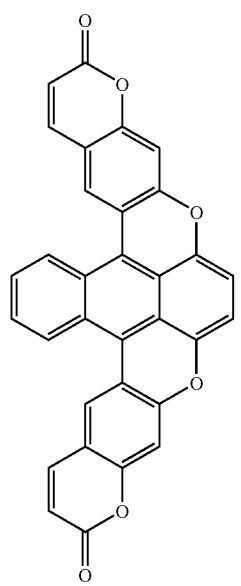
No. 371
No. 372
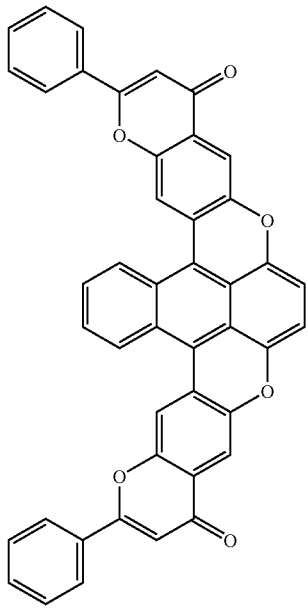
No. 373
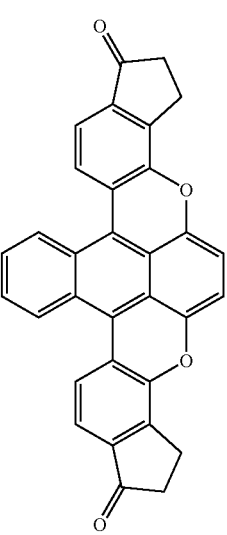

-continued
No. 374
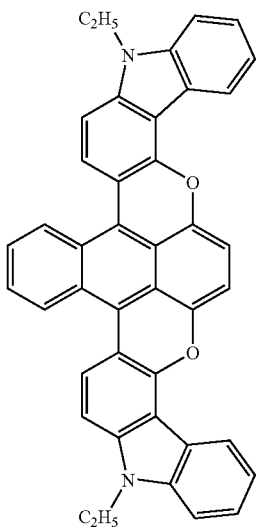
No. 375
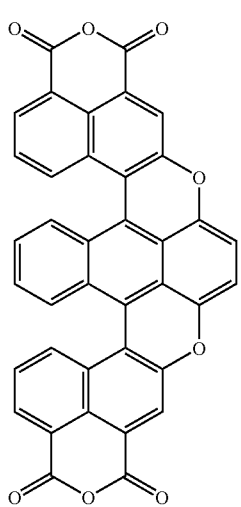
No. 376
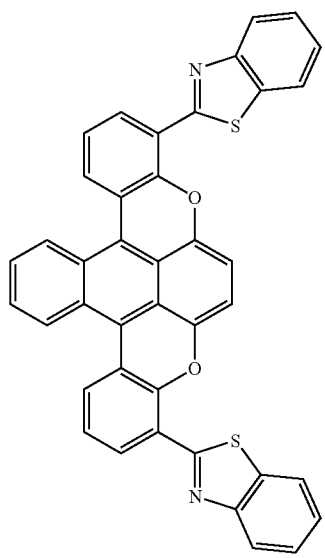
-continued
No. 377
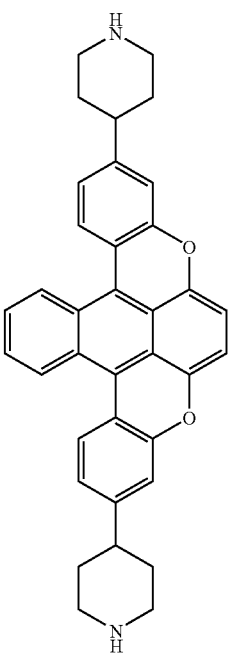
No. 378
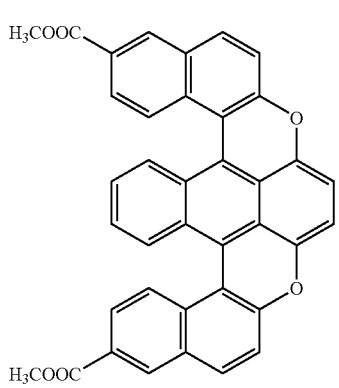
No. 379
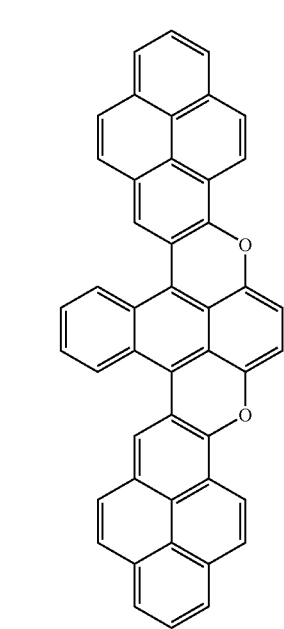

No. 380
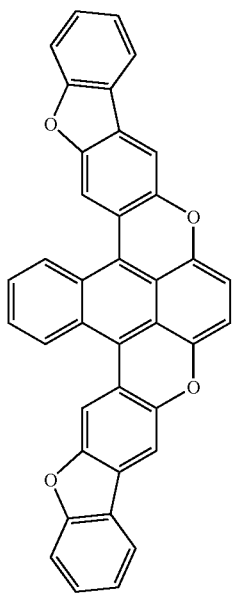
No. 381
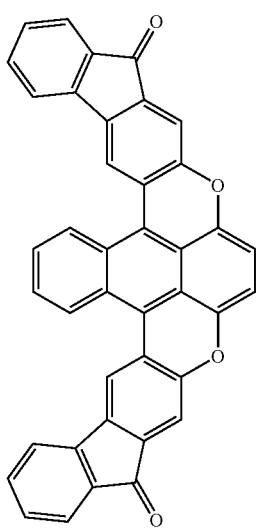
No. 382
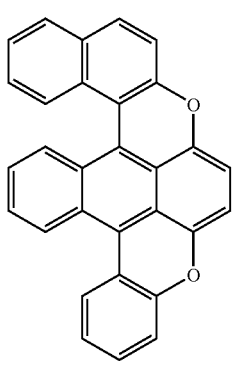
No. 383
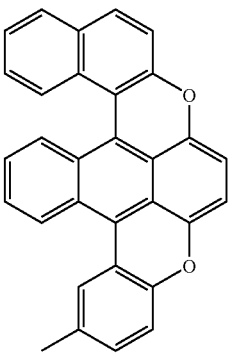
No. 384
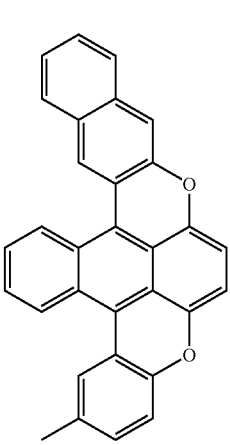
No. 385
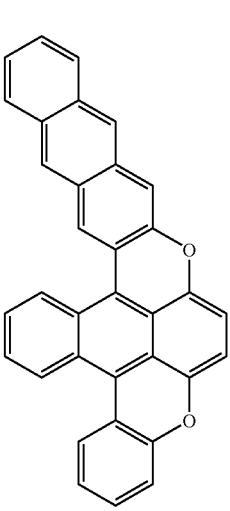

No. 386
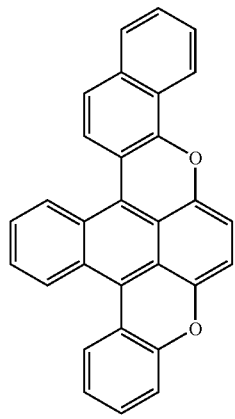
No. 389
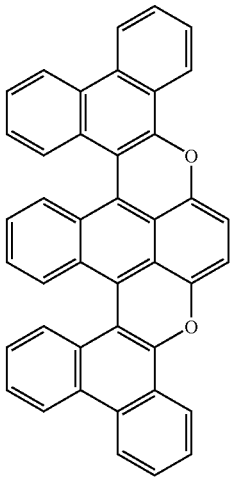
No. 387
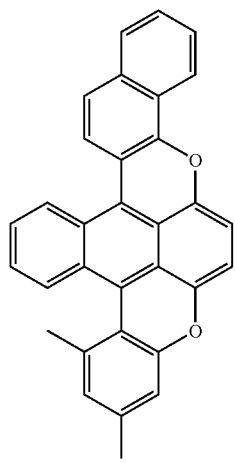
No. 390
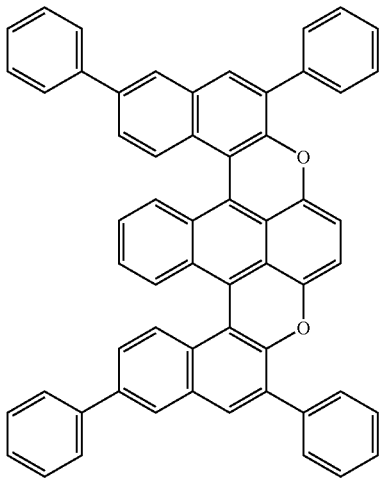
No. 388
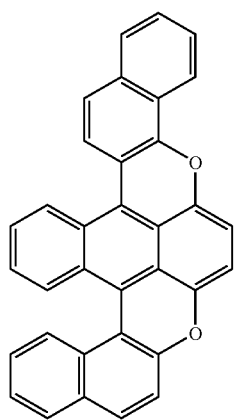
No. 391
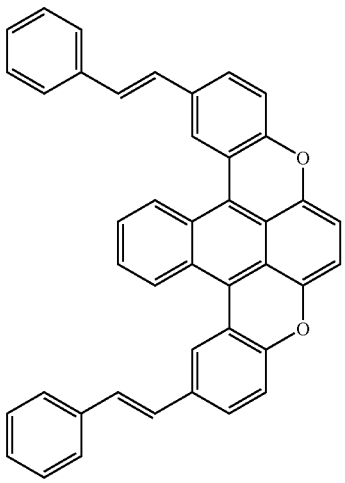

No. 392
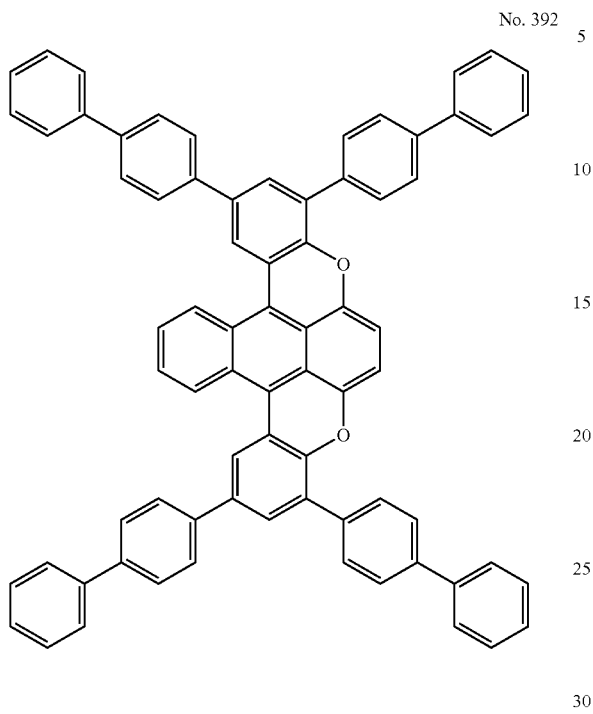
No. 394
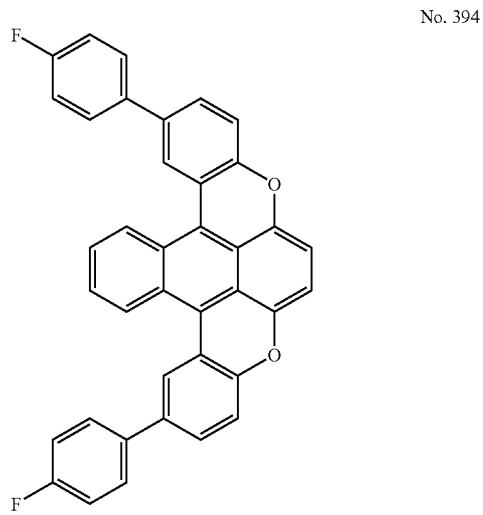
No. 393
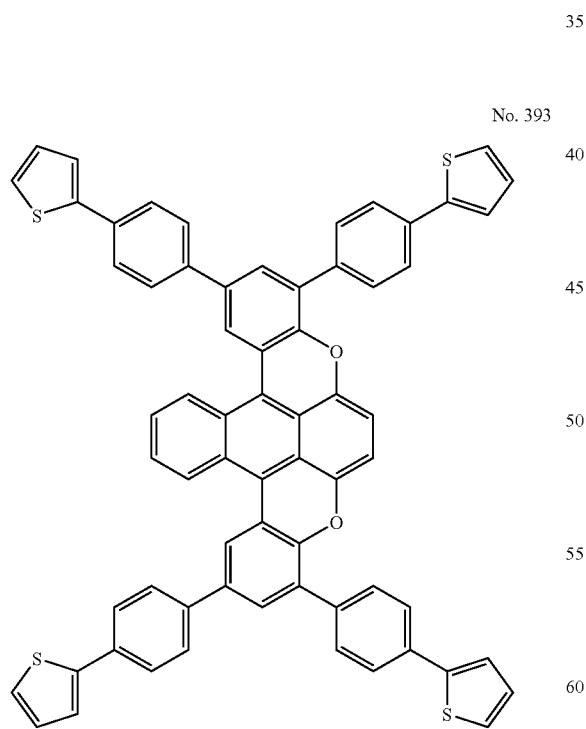
No. 395
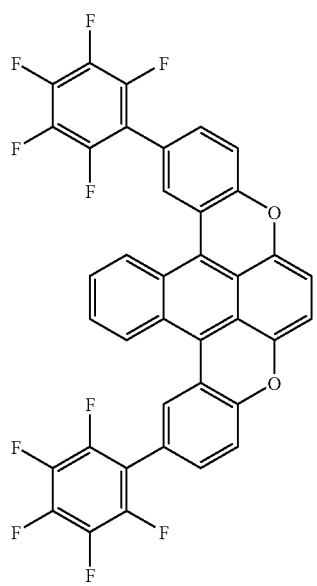
Hereinafter, examples of the compounds represented by Formula (22), i.e., the compounds represented by Formula (4) wherein each of $R_{19}$ to $R_{20}$ and $R_{25}$ to $R_{29}$ is a hydrogen atom and $X_3$ and $X_4$ are sulfur atoms, are listed in Table 6. The abbreviations in Table 6 are the same as those in Table 5.

TABLE 6

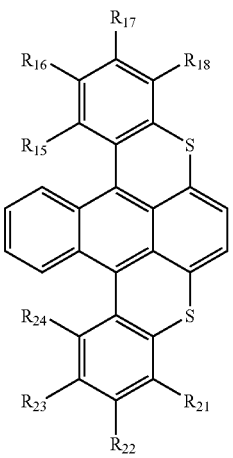

(22)

| Compound NO. | R15 | R16 | R17 | R18 | R24 | R23 | R22 | R21 |
|---|---|---|---|---|---|---|---|---|
| 396 | H | H | H | H | H | H | H | H |
| 397 | H | CH3 | H | H | H | CH3 | H | H |
| 398 | H | C2H5 | H | H | H | C2H5 | H | H |
| 399 | H | CH3 | H | CH3 | H | CH3 | H | CH3 |
| 400 | H | H | C2H5 | H | H | H | C2H5 | H |
| 401 | CH3 | H | CH3 | H | CH3 | H | CH3 | H |
| 402 | H | t-C4H9 | H | H | H | t-C4H9 | H | H |
| 403 | H | CH3 | H | H | H | H | H | H |
| 404 | H | Ph | H | H | H | Ph | H | H |
| 405 | H | H | H | Ph | H | H | H | Ph |
| 406 | H | H | Ph | H | H | H | Ph | H |
| 407 | H | Np | H | H | H | Np | H | H |
| 408 | H | H | H | Np | H | H | H | Np |
| 409 | H | H | t-C4H9 | H | H | H | t-C4H9 | H |
| 410 | H | OPh | H | H | H | OPh | H | H |
| 411 | H | H | OPh | H | H | H | OPh | H |
| 412 | H | OCH3 | H | H | H | OCH3 | H | H |
| 413 | H | H | OCH3 | H | H | H | OCH3 | H |
| 414 | H | Th | H | H | H | Th | H | H |
| 415 | H | Py | H | H | H | Py | H | H |
| 416 | H | CH3 | H | H | H | Cy | H | H |
| 417 | H | CH3 | H | H | H | Ph | H | H |
| 418 | Ph | H | H | H | H | H | Ph | H |
| 419 | H | Py | H | H | H | H | H | H |
| 420 | H | Cl | H | H | H | Cl | H | H |
| 421 | H | I | H | H | H | I | H | H |
| 422 | H | CN | H | H | H | CN | H | H |
| 423 | H | H | NO2 | H | H | H | NO2 | H |
| 424 | H | H | OH | H | H | H | OH | H |
| 425 | H | N(CH3)2 | H | H | H | N(CH3)2 | H | H |
| 426 | H | COOH | H | H | H | H | H | H |
| 427 | H | CHO | H | H | H | H | H | H |
| 428 | H | COOCH3 | H | H | H | COOCH3 | H | H |
| 429 | H | MPh | H | H | H | MPh | H | H |
| 430 | CH3 | CH3 | CH3 | H | CH3 | CH3 | CH3 | H |
| 431 | H | COPh | H | H | H | COPh | H | H |
| 432 | H | COOPh | H | H | H | COOPh | H | H |
| 433 | F | F | F | H | F | F | F | H |
| 434 | H | Ph | H | Ph | H | Ph | H | Ph |
| 435 | H | F | H | H | H | F | H | H |
| 436 | H | F | H | F | H | F | H | F |
| 437 | F | H | F | H | F | H | F | H |
| 438 | H | Br | H | H | H | Br | H | H |
| 439 | H | CF3 | H | H | H | CF3 | H | H |
| 440 | H | CF3 | H | CF3 | H | CF3 | H | CF3 |
| 441 | H | H | C2F5 | H | H | H | C2F5 | H |
| 442 | CF3 | H | CF3 | H | CF3 | H | CF3 | H |
| 443 | H | Br | H | Br | H | Br | H | Br |
| 444 | H | H | H | Br | H | H | H | Br |

Examples of other compounds represented by Formula (22) ($X_3$ and $X_4$ are sulfur atoms) are listed below.
No. 445
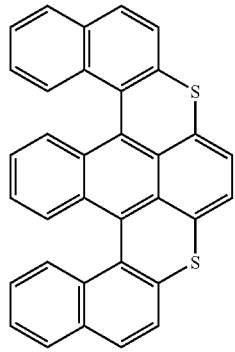
No. 446
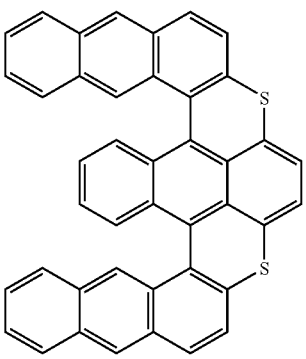
No. 447
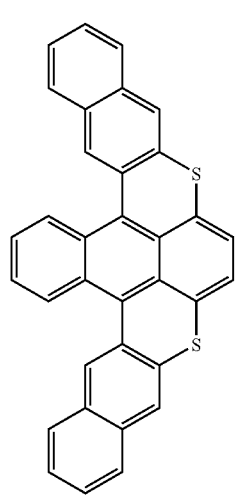
No. 448
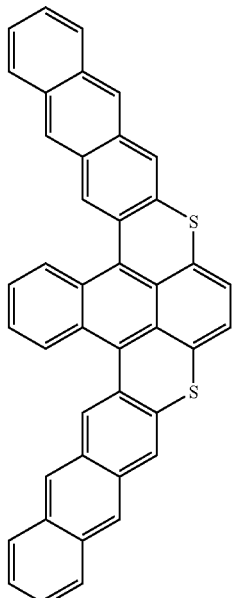
No. 449
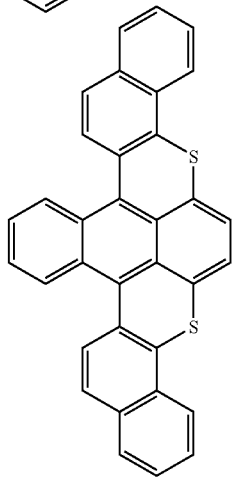
No. 450
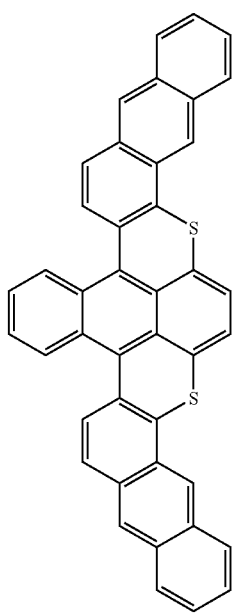

-continued
No. 451
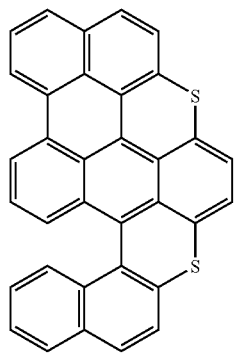
No. 452
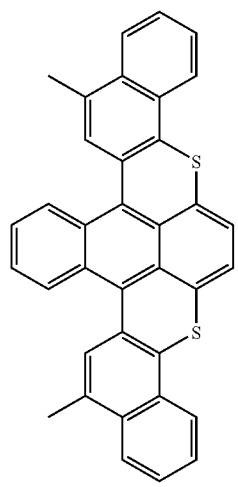
No. 453
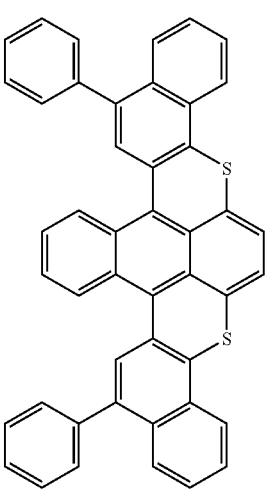
-continued
No. 454
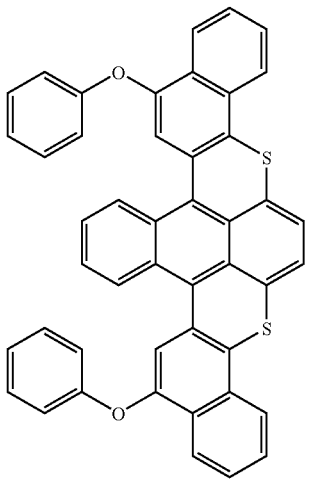
No. 455
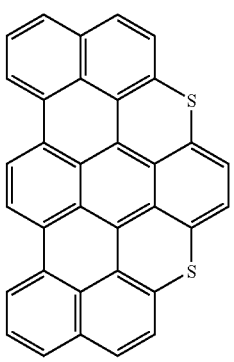
No. 456
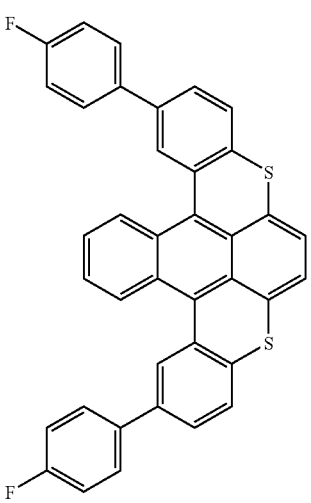
Hereinafter, examples of the compounds represented by Formula (23), i.e., the compounds represented by Formula (4) wherein each of $R_{19}$ to $R_{20}$ and $R_{25}$ to $R_{28}$ is a hydrogen atom and X is a selenium atom, are listed in Table 7. The abbreviations in Table 7 are the same as those in Table 5.

TABLE 7

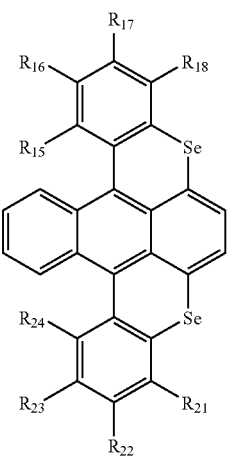

(23)

| Compound NO. | $R_{15}$ | $R_{16}$ | $R_{17}$ | $R_{18}$ | $R_{24}$ | $R_{23}$ | $R_{22}$ | $R_{21}$ |
|---|---|---|---|---|---|---|---|---|
| 457 | H | H | H | H | H | H | H | H |
| 458 | H | $CH_3$ | H | H | H | $CH_3$ | H | H |
| 459 | H | $C_2H_5$ | H | H | H | $C_2H_5$ | H | H |
| 460 | H | $CH_3$ | H | $CH_3$ | H | $CH_3$ | H | $CH_3$ |
| 461 | H | H | $C_2H_5$ | H | H | H | $C_2H_5$ | H |
| 462 | $CH_3$ | H | $CH_3$ | H | $CH_3$ | H | $CH_3$ | H |
| 463 | H | t-$C_4H_9$ | H | H | H | t-$C_4H_9$ | H | H |
| 464 | H | $CH_3$ | H | H | H | H | H | H |
| 465 | H | Ph | H | H | H | Ph | H | H |
| 466 | H | H | H | Ph | H | H | H | Ph |
| 467 | H | H | Ph | H | H | H | Ph | H |
| 468 | H | Np | H | H | H | Np | H | H |
| 469 | H | H | H | Np | H | H | H | Np |
| 470 | H | H | t-$C_4H_9$ | H | H | H | t-$C_4H_9$ | H |
| 471 | H | OPh | H | H | H | OPh | H | H |
| 472 | H | H | OPh | H | H | H | OPh | H |
| 473 | H | $OCH_3$ | H | H | H | $OCH_3$ | H | H |
| 474 | H | H | $OCH_3$ | H | H | H | $OCH_3$ | H |
| 475 | H | Th | H | H | H | Th | H | H |
| 476 | H | Py | H | H | H | Py | H | H |
| 477 | H | $CH_3$ | H | H | H | Cy | H | H |
| 478 | H | $CH_3$ | H | H | H | Ph | H | H |
| 479 | Ph | H | H | H | H | H | Ph | H |
| 480 | H | Py | H | H | H | H | H | H |
| 481 | H | Cl | H | H | H | Cl | H | H |
| 482 | H | I | H | H | H | I | H | H |
| 483 | H | CN | H | H | H | CN | H | H |
| 484 | H | H | $NO_2$ | H | H | H | $NO_2$ | H |
| 485 | H | H | OH | H | H | H | OH | H |
| 486 | H | $N(CH_3)_2$ | H | H | H | $N(CH_3)_2$ | H | H |
| 487 | H | COOH | H | H | H | H | H | H |
| 488 | H | CHO | H | H | H | H | H | H |
| 489 | H | $COOCH_3$ | H | H | H | $COOCH_3$ | H | H |
| 490 | H | MPh | H | H | H | MPh | H | H |
| 491 | $CH_3$ | $CH_3$ | $CH_3$ | H | $CH_3$ | $CH_3$ | $CH_3$ | H |
| 492 | H | COPh | H | H | H | COPh | H | H |
| 493 | H | COOPh | H | H | H | COOPh | H | H |
| 494 | F | F | F | H | F | F | F | H |
| 495 | H | Ph | H | Ph | H | Ph | H | Ph |
| 496 | H | F | H | H | H | F | H | H |
| 497 | H | F | H | F | H | F | H | F |
| 498 | F | H | F | H | F | H | F | H |
| 499 | H | Br | H | H | H | Br | H | H |
| 500 | H | $CF_3$ | H | H | H | $CF_3$ | H | H |
| 501 | H | $CF_3$ | H | $CF_3$ | H | $CF_3$ | H | $CF_3$ |
| 502 | H | H | $C_2F_5$ | H | H | H | $C_2F_5$ | H |
| 503 | $CF_3$ | H | $CF_3$ | H | $CF_3$ | H | $CF_3$ | H |
| 504 | H | Br | H | Br | H | Br | H | Br |

Examples of the compounds represented by Formula (4), wherein each of $R_{19}$ to $R_{20}$ and $R_{25}$ to $R_{28}$ is a hydrogen atom and X is $NR_{29}$, are listed below. The compounds represented by Formula (4). which are shown as the compounds represented by the following Formula (24), with its two $NR_{29}$ groups being indicated respectively as $NR_{32}$ and $NR_{33}$, are summarized in Table 8. In the Table, 4MePh represents a 4-methylphenyl group; 4PhPh, 4-phenylphenyl; 2PhPh, 2-phenylphenyl; and t-Bu, t-butyl.

TABLE 8

(24)

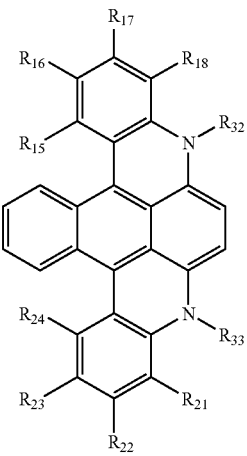

| Compound NO. | $R_{15}$ | $R_{16}$ | $R_{17}$ | $R_{18}$ | $R_{24}$ | $R_{23}$ | $R_{22}$ | $R_{21}$ | $R_{32}$ | $R_{33}$ |
|---|---|---|---|---|---|---|---|---|---|---|
| 505 | H | H | H | H | H | H | H | H | H | H |
| 506 | H | $CH_3$ | H | H | H | $CH_3$ | H | H | $CH_3$ | $CH_3$ |
| 507 | H | $CH_3$ | H | H | H | $CH_3$ | H | H | H | H |
| 508 | H | H | H | H | H | H | H | H | $CH_3$ | $CH_3$ |
| 509 | H | H | H | H | H | H | H | H | $CH_2Br$ | $CH_2Br$ |
| 510 | H | $CH_3$ | H | H | H | $CH_3$ | H | H | $CH_2Ph$ | $CH_2Ph$ |
| 511 | H | H | H | H | H | H | H | H | Ph | Ph |
| 512 | H | $CH_3$ | H | H | H | $CH_3$ | H | H | 4MePh | 4MePh |
| 513 | H | Ph | H | H | H | Ph | H | H | $CH_3$ | $CH_3$ |
| 514 | H | Ph | H | H | H | Ph | H | H | 4PhPh | 4PhPh |
| 515 | H | H | H | Ph | H | H | H | Ph | 2PhPh | 2PhPh |
| 516 | H | H | H | H | H | H | H | H | Ph | H |
| 517 | H | H | H | H | H | H | H | H | Ph | $CH_3$ |
| 518 | H | H | H | H | H | H | H | H | t-Bu | t-Bu |
| 519 | H | Ph | H | H | H | H | H | H | Ph | H |
| 520 | H | F | H | H | H | F | H | H | Ph | Ph |
| 521 | H | F | H | F | H | F | H | F | H | H |
| 522 | F | H | F | H | F | H | F | H | Ph | Ph |
| 523 | H | Br | H | H | H | Br | H | H | Ph | Ph |
| 524 | H | $CF_3$ | H | H | H | $CF_3$ | H | H | Ph | Ph |
| 525 | H | $CF_3$ | H | $CF_3$ | H | $CF_3$ | H | $CF_3$ | Ph | Ph |
| 526 | H | H | $C_2F_5$ | H | H | H | $C_2F_5$ | H | Ph | Ph |
| 527 | $CF_3$ | H | $CF_3$ | H | $CF_3$ | H | $CF_3$ | H | Ph | Ph |

Examples of other compounds represented by Formula (4) are listed below.

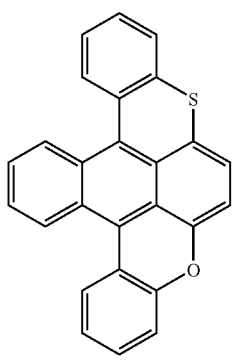

No. 528

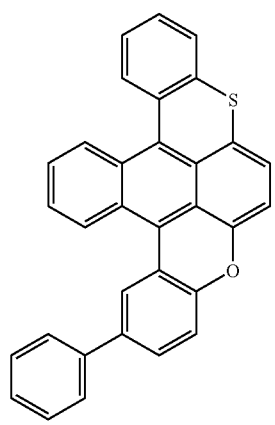

No. 529

-continued

No. 530 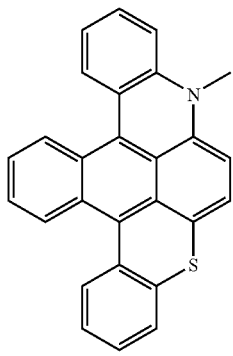

No. 531 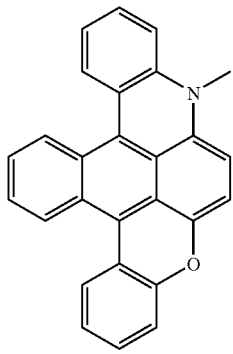

No. 532 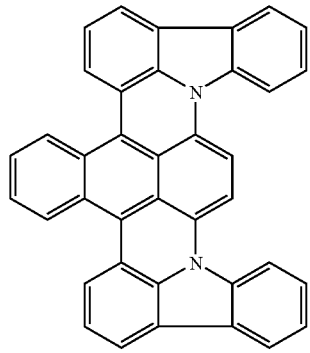

No. 533 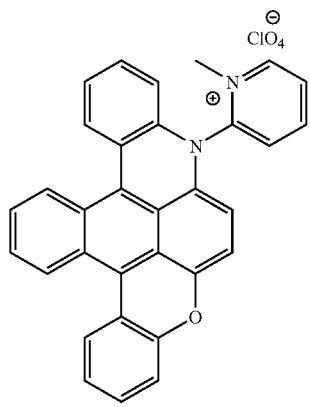

No. 534 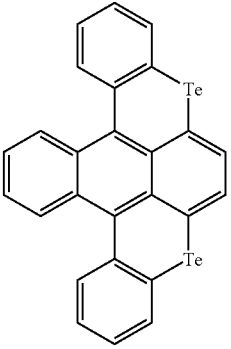

No. 535 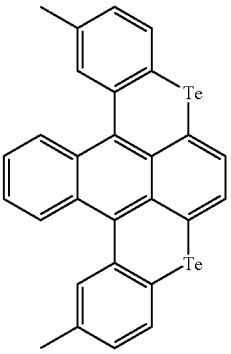

No. 536 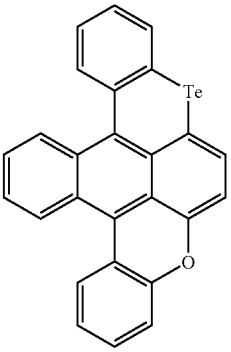

Hereinafter, the light-emitting device according to the invention will be described.

The light-emitting device according to the invention can be obtained by adding a compound having the basic skeleton represented by Formula (1) or (2) and as needed a light-emitting material (light-emitting compound) other than the compound to one or more layers of organic thin film formed between an anode and a cathode. The device thus obtained emits light by application of electric energy. The method of adding a compound having the basic skeleton represented by Formula (1) or (2) (hereinafter, sometimes referred to as a "basic skeleton compound") into the organic thin film layers of light-emitting device is not particularly limited, and an organic thin film containing the basic skeleton compound may be formed, for example, by depositing the basic skeleton compound and as needed other organic compounds on the electrode or on another organic thin film, for example, by vacuum deposition. The basic skeleton compound for use in the invention is a light-emitting compound that emits light by application of electric energy, and may be used as the host or dopant for the light-emitting material, or alternatively, as the material for a positive hole-injecting layer described below.

When used as a dopant, the basic skeleton compound is preferably contained in at least one layer of positive hole-transporting layer, electron-transporting layer, and light-emitting layer. The basic skeleton compound is preferably a compound represented by Formula (3) or (4).

In a preferably structure, the light-emitting device according to the invention contains between an anode and a cathode, at least, a positive hole-transporting layer and a light-emitting layer, or a positive hole-injecting layer and a light-emitting positive hole-transporting layer, and an electron-transporting layer in that order from the anode to the cathode, all of which contain the basic skeleton compound. Normally, the anode is formed directly on the base material for supporting the device.

The light-emitting device according to the invention (organic electroluminescent device) is easy to cause to deteriorate by gas such as oxygen or water. Therefore, it is preferable to block these substances sufficiently if needed by forming a gas barrier layer or the like. For example, it is preferable to protect the device as needed with a metal (such as platinum, gold, silver, copper, iron, tin, aluminum, or indium, or an alloy containing these metals), an inorganic material (such as silica, titania, silicon nitride, silicon oxide, silicon nitride oxide, or germanium oxide) or an organic polymer (such as polyvinyl alcohol, polyvinyl chloride, hydrocarbon polymer, or fluorinated polymer); and as needed to seal the device by using a glass or metal tube or the like together with a dehydrating agent (such as barium oxide, phosphorus pentoxide, or calcium oxide) and a getter, or by using a sealant laminated film, for example, of a ceramic layer and a polymer layer, or the like.

Hereinafter, the light-emitting device according to the invention will be described in more detail.

Any known material may be used as the anode for the light-emitting device according to the invention, and examples thereof include conductivity metal oxides such as tin oxide, indium oxide, indium tin oxide (ITO), and indium zinc oxide (IZO); metals such as gold, silver, and chromium; inorganic conductivity materials such as copper iodide and copper sulfide; conductivity polymers such as polythiophene, polypyrrole, and polyaniline; and the like. Generally, a transparent electrode is often used for more efficient transmission of light, but an opaque material may also be used for top emission systems in which light is emitted not from the substrate side but upward from the substrate.

Any one of known substrates may be used as the substrate supporting the light-emitting device, and examples thereof include soda lime glass, nonalkali glass, and the like. The substrate has a thickness sufficient for maintaining a certain mechanical strength, which can be 0.5 mm or more. With respect to quality of the glass, preferably, a smaller amount of ion migrates into the organic layer from the glass, and thus, a nonalkali glass is preferable. Commercially available soda lime glasses that are barrier-coated with $SiO_2$ or the like may also be used. In addition, substrates other than glass, for example, plastic substrates of polyester, polyacrylate, polycarbonate, polysulfone, and the like may also be used. A TFT semiconductor substrate, such as silicon substrate, having a device-driving circuit may also be used as the substrate for top emission systems.

The electrode is not particularly limited if it can be supplied with electricity in an amount sufficient for emitting light, but preferably has low resistance from the viewpoint of electric consumption of the device. A transparent ITO electrode, for example, having a resistance of 300Ω/☐ or less is effective and usable as the electrode for the device. Substrates having a resistance of approximately 10Ω/☐ are now available, and thus use of substrates having a lower resistance is preferable. The thickness of the ITO film may be selected arbitrarily according to the resistance. The thickness is normally in the range of 10 to 300 nm. The method of forming a transparent electrode for example of ITO or IZO is not particularly limited, and examples thereof include electron beam method, sputtering method, vacuum deposition method, chemical reaction method, and the like.

The cathode material is not particularly limited if it is a material that allows efficient injection of electron into the organic matter layer. Typical examples thereof include platinum, gold, silver, copper, iron, tin, zinc, aluminum, indium, chromium, lithium, sodium, potassium, calcium, magnesium, and the like. For increasing the electron-injecting efficiency of the cathode and improving the properties of the device, it is preferable to use an alloy of a low-work function metal such as lithium, sodium, potassium, calcium, or magnesium and a stable metal such as aluminum or silver, or alternatively a laminated structure consisting of a low-work function metal above mentioned and a stable metal above mentioned as the cathode. Among many alloys, alloys of magnesium and silver and of aluminum and lithium are favorably used. An inorganic salt such as lithium fluoride may also be used as the electrode in laminated structure, and electrodes having a laminated structure of lithium fluoride and aluminum have been used widely. Alternatively, an ITO, IZO, or other film, which can be formed at relatively lower temperature, may be used for emitting light not from the substrate side but upward from the substrate.

Typical examples of the configurations of the organic thin film layers in the light-emitting device according to the invention include configurations of a) positive hole-transporting layer/electron-transporting light-emitting layer,
b) positive hole-transporting layer/light-emitting layer/electron-transporting layer,
c) positive hole-transporting and light-emitting layer/electron-transporting layer,
d) positive hole-transporting layer/light-emitting layer/positive hole-blocking layer/electron-transporting layer,
e) positive hole-transporting and light-emitting layer/positive hole-blocking layer/electron-transporting layer; as well as
f) the configurations a) to e) above mentioned having an additional electron-injecting layer after the electron-transporting light-emitting layer or the electron-transporting layer;
g) the configurations a) to f) above mentioned having an additional positive hole-injecting layer before the positive hole-transporting layer or the positive hole-transporting light-emitting layer; and
h) a single-layer configuration having the functions of all layer in the configurations above mentioned [which is prepared by blending the materials for the layers in the configurations a) to f)].

In the case of a light-emitting material, the material for use may be used in combination with a bipolar light-emitting material, which is often found in polymeric materials, or alternatively, the materials constituting respective layers may be used in increased or decreased amounts according to respective layers.

The light-emitting device according to the invention contains the basic skeleton compound at least in any one of the layers above mentioned.

In the invention, when an "organic thin film contains a compound having the basic skeleton represented by Formula (1) or (2)", the thin film contains the compound together with other materials, or is composed only of the compound. Similarly in the invention, when an organic thin film "contains the basic skeleton compound" or "the basic skeleton compound is contained in an organic thin film", the organic thin film should be understood in this context unless specified otherwise. Accordingly in the invention, the organic thin film above mentioned means an organic thin film composed only of the compound or that which contains the compound and another organic compound, for example, an organic compound conventionally used as the thin film for light-emitting device exemplified below.

In the invention, the basic skeleton compound is used, for example, as a light-emitting material or a material for the positive hole-injecting layer in the light-emitting device according to the invention. When it is used as a light-emitting material, it may be a host or a dopant. When used as a dopant, the basic skeleton compound may be used in any layer, but normally in at least one of the following layers: light-emitting layer, positive hole-transporting layer, and electron-transporting layer.

The positive hole-transporting layer is prepared according to a normal method, by forming single or multiple layers of one or more positive hole-transporting materials on an anode or by forming a single or multiple layers of a mixture of two or more materials previously prepared as needed on an anode. The positive hole-transporting material is not particularly limited, if it is a compound that can form a thin film and transport positive holes injected from anode. Usually used is a material known in the art, and examples thereof include triphenylamines such as N,N'-diphenyl-N,N'-di(3-methylphenyl)-4,4'-diphenyl-1,1'-diamine, and N,N'-dinaphthyl-N,N'-diphenyl-4,4'-diphenyl-1,1'-diamine; heterocyclic compounds such as bis(N-allylcarbazole)'s or bis(N-alkylcarbazole)'s, pyrazoline derivatives, stilbene compounds, hydrazone compounds, oxadiazole derivatives and porphyrin derivatives; the polymers (polycarbonate, styrene derivatives, polyvinylcarbazole, polysilane, and the like) having the positive hole-transporting materials described above such as triphenylamines, carbazoles or oxadiazole derivatives as the side chain. Then, the positive hole-injecting layer will be described. The positive hole-injecting layer is a layer formed for improving the adhesion of the layers of the anode and the positive hole-transporting material and hole injection efficiency during injection of positive holes from the anode. In addition, the positive hole-transporting material described above or the like may be mixed and used in the range that the resulting positive hole-injecting layer functions. Examples of the materials for the layer include materials commonly used including phthalocyanine derivatives, thiophene derivatives, hydrazine derivatives, aromatic amine derivatives (e.g., starburst amines such as 4,4',4''-tris(N-3-methylphenyl-N-phenylamino)-triphenylamine (m-MTDATA)), polymers such as polyphenylene vinylene and polythienylene vinylene, polythiophene derivatives such as poly(ethylenedioxythiophene) (PEDOT), and the like. Alternatively, the basic skeleton compound according to the invention may also be used favorably as the positive hole-injecting layer. Favorable examples of the compounds having the basic skeleton represented by Formula (1) or (2) are the compounds represented by Formulae (3) and (4). Use of such a compound as the positive hole-injecting layer leads to decrease in the threshold voltage during light emission and improvement in power efficiency. Thus, it reduces electric consumption of the device and provides a light-emitting device improved in stability.

The electron-transporting material for use as the electron-transporting layer should transport electrons injected from cathode between electrodes to which an electric field is applied, and an electron-transporting material superior in electron-receiving efficiency and in the efficiency of transporting injected electrons is preferable. For that reason, it should be a material higher in electron affinity, larger in electron mobility, and superior in stability that generates a smaller amount of impurities (which become traps) during production or use. In the invention, any one of known materials that satisfy the requirements above mentioned may be used, and examples thereof include metal complexes of quinolinol derivatives represented by tris(8-quinolinolato) aluminum complex, tropolone metal complexes, perylene derivatives, perynone derivatives, naphthalimide derivatives, naphthalic acid derivatives, oxadiazole derivatives, triazole derivatives, bisstyryl derivatives, pyrazine derivatives, phenanthroline derivatives, benzoxazole derivatives, quinoxaline derivatives, anthracene derivatives, carbazole derivatives, and the like. However, the electron-transporting materials are not limited to these examples. These electron-transporting materials may be used alone, or as a laminated layer or mixture with another electron-transporting material.

The electron-injecting layer is a layer formed for improving the adhesion of the layers of cathode and electron-transporting material and the electron-injecting efficiency during injection of electrons from the cathode. Any one of known materials may be used as the material for use as the electron-injecting layer, and examples thereof commonly used include an inorganic salt such as lithium fluoride or lithium oxide described above for the cathode material, organic layers doped with an alkali metal, or organic metal complexes containing an alkali metal such as lithium.

The positive hole-blocking layer is a layer for preventing the deterioration in luminous efficiency due to flow out of the positive holes from the cathode to the regions other than the light-emitting layer, and any compounds that have the function above mentioned may be used without restriction as the positive hole-blocking material. The positive hole-blocking layer is formed by laminating or mixing and then laminating one or multiple positive hole-blocking materials. Favorable examples of the positive hole-blocking materials include phenanthroline derivatives such as vasophenanthroline and vasocuproine, silole derivatives, metal complexes of quinolinol derivative, oxadiazole derivatives, oxazole derivatives, and the like.

The light-emitting layer, which may also be called a strong light-emitting positive hole-transporting layer (positive hole-transporting light-emitting layer) or a strong light-emitting electron-transporting layer (electron-transporting light-emitting layer), is usually formed with a light-emitting material. It may be made only of a host material or a mixture of a host material and a dopant material. The host material or the dopant material may be a single component or a mixture of multiple components. The dopant material may be entirely or partially contained in the host material. The dopant material may be laminated or dispersed.

The basic skeleton compound for use in the invention emits light by application of electric energy, and thus, may be used effectively as a light-emitting material in the light-emitting layer. That is, it may be used as a light-emitting material in forming a light-emitting layer, or alternatively, contained in the light-emitting positive hole-transporting layer or the light-emitting electron-transporting layer. In addition, use of the basic skeleton compound according to the invention as the dopant for the positive hole-transporting layer or the electron-transporting layer gives a superior light-emitting device. The basic skeleton compound is preferably a compound represented by Formula (3) or (4) above mentioned.

For more definite display of red color, the peak wavelength in the emission spectrum thereof is in the range of preferably 580 nm or more and 690 nm or less, and more preferably 600 nm or more and 670 nm or less; and the half value width thereof is preferably 100 nm or less. The emission spectrum has preferably a single peak, but occasionally has multiple maximum points or shoulders at sides of the peak due to overlap with other peaks. In the invention, the peak wavelength is defined as the wavelength of the primary peak at the center of the emission wavelength range.

The basic skeleton compound having the peak wavelength in the range of approximately 550 nm to 660 nm in its emission spectrum may be used as an orange to red light-emitting material. The compound is particularly favorable as the dopant material, but may be used as a single light-emitting material. When used as a dopant, multiple basic skeleton compounds above mentioned may be used as a mixture for emission of a red light further improved in color purity.

Any one of commonly known dopant materials may be used for the light-emitting device according to the invention. When used as a dopant, the basic skeleton compound may be used in combination with a common dopant material (e.g., as an assist dopant). When the basic skeleton compound is used for applications other than the dopant for light-emitting device (e.g., positive hole-injecting layer, light-emitting layer, or the like), a common dopant material may be used alone as the dopant.

Examples of the common dopants include perylene derivatives such as bis(diisopropylphenyl)perylenetetracarboxylic imide, perynone derivatives, rare-earth metal complexes such as Eu complexes having an acetylacetone derivative, a benzoylacetone derivative, a phenanthroline derivative or the like as the ligand, 4-(dicyanomethylene)-2-methyl-6-(p-dimethylaminostyryl)-4H-pyran (DCM) and the analogues thereof, metalphthalocyanine derivatives such as magnesium phthalocyanine and aluminum chlorophthalocyanine, rhodamine compounds, deazaflavine derivatives, coumarin derivatives, oxazine compounds, squarylium compounds, violanthrone compounds, nailered, pyrromethene derivatives such as 5-cyanopyrromethene-$BF_4$ complex, and the like. In addition, dopants containing a phosphorescence material of metal complex, for example of iridium or platinum, may also be used favorably. However, the examples are not limited thereto. When two kinds of dopants are used as a mixture, it is possible to obtain a red light improved in color purity, by using an assist dopant, for example of rubrene that efficiently transfers the energy from the host colorant. In any case, it is preferable to dope a compound higher in quantum yield (capable of converting electric energy into light such as phosphorescence or fluorescence at higher efficiency) for obtaining high brightness.

An excessively higher amount of the dopant used may lead to a concentration quenching phenomenon, and thus, the amount thereof is usually 20 wt % or less, preferably 10 wt % or less, and still more preferably 5 wt % or less, with respect to the host material. For doping a dopant material into a host material of the light-emitting layer, the dopant material may be co-deposited with the host material, or deposited simultaneously after it is mixed previously with the host material. The dopant material may also be used as it holds a host material from both sides in the sandwich shape. In such a case, one or more dopant layers may be formed on the host material. Examples of the host materials for use include the electron-transporting materials described above, the compounds exemplified as the positive hole-transporting materials (light-emitting compounds), and the like. Preferable examples thereof include metal complexes of quinolinol derivatives represented by tris(8-quinolinolato)aluminum complex, tropolone metal complexes, perylene derivatives, perynone derivatives, naphthalimide derivatives, naphthalic acid derivatives, bisstyryl derivatives, pyrazine derivatives, phenanthroline derivatives, benzoxazole derivatives, quinoxaline derivatives, triphenylamines, bis(N-allylcarbazole)'s or bis(N-alkylcarbazole)'s, pyrazoline derivatives, stilbene compounds, anthracene derivatives, hydrazone compounds, oxadiazole derivatives, heterocyclic compounds represented by carbazole derivatives, and the like. These host materials may be used alone or as a laminate or mixture with another material.

The materials for use as the positive hole-transporting layer, light-emitting layer, electron-transporting layer, positive hole-transporting light-emitting layer, electron-transporting light-emitting layer, and positive hole-blocking layer described above may form each layer alone; or may be dissolved or dispersed in a solvent-soluble resin such as polyvinyl chloride, polycarbonate, polystyrene, polystyrenesulfonic acid, poly(N-vinylcarbazole), poly(methyl) (meth)acrylate, polybutylmethacrylate, polyester, polysulfone, polyphenylene oxide, polybutadiene, hydrocarbon resin, ketone resin, phenoxy resin, polysulfone, polyamide, ethylcellulose, vinyl acetate, ABS resin, or polyurethane resin or in a curable resin such as phenolic resin, xylene resin, petroleum resin, urea resin, melamine resin, unsaturated polyester resin, alkyd resin, epoxy resin, or silicone resin as a polymer binder.

The basic skeleton compound may be used as a light-emitting material, and if so, it is used, for example, in the following device configurations:

(a) A positive hole-transporting layer is formed on a common conductive substrate, and the compound according to the invention is laminated alone or as a dopant together with an electron-transporting host material (host material for light-emitting material; the same shall apply hereinafter) thereon;

(b) A positive hole-transporting layer is formed on a common conductive substrate, and the compound according to the invention is laminated alone or as a dopant together with a host material (positive hole-transporting, electron-transporting, or dual-purpose compound material), and an electron-transporting layer is formed additionally thereon; and (c) The compound according to the invention is laminated alone or as a dopant together with a positive hole-transporting host material on a common conductive substrate, and an electron-transporting layer is formed additionally thereon. Needless to say, a positive hole-injecting layer, an electron-injecting layer, a positive hole-blocking layer, or the like may be formed additionally on these devices as needed.

When the basic skeleton compound is used as a light-emitting material, configuration (b) is preferable; lamination as a dopant together with a host material (positive hole-transporting, electron-transporting, or dual-purpose compound material) is preferable; and the thin film is formed preferably by vacuum deposition.

The basic skeleton compound is favorably used as a positive hole-injecting material. Use of the compound leads to decrease in the threshold voltage during light emission and increase in power efficiency. Thus, it allows decrease in electric consumption of the device and improvement in stability of the light-emitting device.

When used as a positive hole-injecting material, the compound is used, for example, in the following device configuration: The basic skeleton compound is laminated alone as a positive hole-injecting material on a common conductive substrate. As described above, thin films such as positive hole-transporting layer, light-emitting layer, and electron-transporting layer are formed thereon respectively if needed, to form an organic layer. An electron-injecting layer, a positive hole-blocking layer, or others may be formed additionally as needed. Additional formation of metal or other electrodes thereon gives a light-emitting device according to the invention.

The method of forming an organic thin film according to the invention is not particularly limited, and examples thereof include resistance-heating vapor deposition, electron beam vapor deposition, sputtering, molecule lamination, coating of a solution or dispersion in solvent, resin, or the like (spin coating, casting or dip coating, etc.), LB method, inkjet method, and the like; but normally, resistance-heating vapor deposition and electron beam vapor deposition are preferable from the point of the properties of the resulting thin film. The resistance-heating vapor deposition is more preferable in the invention from the points of the homogeneity of film and others. Although many aromatic group-substituted derivatives have steric hindrance, it is possible to form a uniform film with such a compound by vacuum deposition. Because the basic skeleton compound is more soluble in organic solvents, it is also possible to form a thin film by dissolving the compound according to the invention in a solvent and coating the resulting solution, for example, by spin coating.

The thickness of each layer varies according to the configuration of the layers and the resistance of the materials and thus cannot be defined specifically, but is usually selected in the range of 0.5 to 5,000 nm, preferably 1 to 1,000 nm, and more preferably 5 to 500 nm. When used alone as a light-emitting layer, the compound according to the invention has a thickness of 0.5 to 300 nm, preferably 1 to 100 nm, and more preferably 3 to 30 nm. When the compound according to the invention is used as a dopant in the light-emitting layer, the layer has a thickness of 0.5 to 300 nm, preferably 1 to 200 nm, and more preferably 3 to 100 nm, although the thickness may vary according to the host material. The amount of the compound used is approximately 0.01 to 50 wt %, usually 0.1 to 20 wt %, and preferably 0.2 to 5 wt % with respect to the host.

When used as a positive hole-injecting layer, the compound has a thickness of 0.5 to 300 nm, preferably 1 to 100 nm, and more preferably 3 to 30 nm.

In the invention, the electric energy means mainly direct current, but pulse or alternating current may also be used. The current and the voltage are not particularly limited, but it is preferable to use the energy as low as possible for maximizing brightness, considering the electric consumption and lifetime of the device.

The basic skeleton compound can emit white light, for example, in combined use of a conventional blue to green light-emitting material. Preferable examples of the blue to green light-emitting materials include anthracene compounds, stilbene compounds, quinoline compounds, and the like. Examples of the white light-emitting devices include devices in combination of a light-emitting device using the blue to green or blue and green light-emitting materials and a red to orange light-emitting device using the basic skeleton compound; devices in combination of a blue or blue-and-green light-emitting material and the basic skeleton compound; and the like. More preferable in the latter is a device having a blue/green light-emitting material or blue-and-green light-emitting materials as host materials and the basic skeleton compound as a dopant material. The basic skeleton compound is preferably used in an amount of normally 0.01 to 2 wt %, more preferably 0.1 to 1.0 wt %, with respect to the host material at the time. Addition of the basic skeleton compound in the range above mentioned averages the extent of degradation of each light-emitting materials and elongates the lifetime of the white light-emitting device.

In the invention, the matrix means picture devices (pixels) for display arranged in the lattice form, and a set of pixels displays a character or an image. Each pixel is formed by using one or more light-emitting devices according to invention. The shape and size of each pixel are determined according to applications. For example, a pixel normally having a side of 300 μm or less in the square or circular form is used for displaying image and character in personal computer, monitor, and television set, while a pixel having a side which can be measured in mm is used for large-screen displays such as display panels. Pixels in the same color may be used for monochrome display, but combination of red, green, and blue pixels is needed for color display. Color displays are typically grouped into delta type and stripe type. A line-sequential drive method (passive type) or an active matrix method may be used for driving the matrix. The line-sequential drive method is advantageous because of its simplicity of structure, and the active matrix method is advantageous, considering the operational properties; and thus, the driving method may be selected suitably according to applications.

The segment-mode display of the invention is a display that emits light from a particular predetermined range on a pattern previously formed for displaying predetermined information. Examples of such displays include displays on digital watch and thermometer for displaying time and temperature, displays on audio visual apparatus, electromagnetic cooker, and the like for displaying operational conditions, panel displays in vehicles, and the like. The light-emitting device according to the invention may be used as the light-emitting face of these displays.

The matrix and segment displays may be present on the same panel.

The light-emitting device according to the invention is also used favorably as backlight. In such a case, any light-emitting devices emitting a color or white light may be used. It is also used favorable for illumination. White light can be obtained by emitting light simultaneously in combination with another conventional blue to green light-emitting material, as described above. In particular for use as backlight or illumination, combined use with blue and green light-emitting materials is preferable considering the color rendering properties, while, for use as direct vision displays, the light-emitting material according to the invention may be used in combination only with a blue to green light-emitting material. Backlight is mainly used for improving the visibility of non-self-luminous display devices, more specifically of liquid crystal display devices, watches, audio visual apparatuses, vehicle panels, display plates, signs, and the like. In particular, it is difficult to reduce the thickness of the backlight units in conventional liquid crystal display devices, especially those for personal computer application in which thinner models are demanded, that contain a fluorescence lamp and optical waveguides, but backlights using the light-emitting device according to the invention are thinner and lighter.

The light-emitting device according to the invention emits orange or red light higher in color purity and sufficiently higher in brightness even at application of low energy. It is also possible to emit high-efficiency white light by combined use with a blue to green light-emitting material commonly used in the art.

Further, use of the condensed polycyclic compound according to the invention as the positive hole-transporting layer allows production of a high-brightness, high-efficiency light-emitting device that has a lower threshold voltage during light emission and operates at a lower voltage.

The compound having the basic skeleton according to the invention is favorably used as an organic electronic material, especially as an organic EL material. In addition, it is possible to produce a high-purity condensed polycyclic compound and increase the purity thereof easily, by the method of producing the compound according to the invention. Further, in a preferable embodiment of the invention, the reaction is carried out in a solvent, which improves the workability drastically.

EXAMPLE

Hereinafter, the invention will be described in more detail with reference to Examples and Comparative Examples, but it should be understood that the invention is not restricted by these examples. In the Examples, "part" means a part by weights and "%", a wt %, unless specified otherwise.

Synthesis Example 1

(Synthesis of Compound No. 3 in Table 1)
(1) In a nitrogen atmosphere, 3 parts of 4-ethylphenol and 1.3 parts of potassium hydroxide were dissolved in 60 parts of toluene and refluxed under heat. After stirring for 5 hours, the solution was allowed to cool, and the solid precipitated was collected by filtration. Then, under a nitrogen stream, the precipitate, 2 parts of 1,5-dichloroanthraquinone and 0.6 part of copper powder were dissolved in 10 parts of DMF, and refluxed under heat for 3 hours. The reaction solution was poured into an aqueous potassium hydroxide solution, and the resulting precipitated solid was filtered, washed, and dried. Then, after removal of inorganic materials with toluene, the solid obtained was recrystallized from 2-ethoxyethanol, filtered, washed, and dried, to give 1.8 parts of 1,5-bis(4-ethylphenoxy)anthraquinone as an intermediate.

(2) A mixture of 0.5 part of the intermediate obtained in (1) above mentioned, 6 parts of anhydrous aluminum chloride, 0.7 part of hydroquinone, and 4.8 parts of sodium chloride was stirred under heat at 180° C. for 10 minutes, and additionally at 160° C. for 15 minutes. A dilute hydrochloric acid was added to the reaction product obtained, and the precipitated solid was filtered and washed with an aqueous hydrosulfite-sodium hydroxide (5 wt %: 7 wt %) solution. The solid obtained was purified by silica gel chromatography and then crystallized from toluene, to give 0.1 part of a desired compound (compound No. 3). The molecular weight of the compound was 414.

Mass spectrometric value: 414 (as determined in SSQ-7000 manufactured by ThermoQuest)
Absorption maximum ($3.3 \times 10^{-4}$ M, in DMF): 507 nm, 542 nm
Emission maximum at an excitation wavelength of 566 nm ($3.3 \times 10^{-4}$ M, in DMF): 585 nm, 609 nm Synthesis Example 2

(Synthesis of Compound No. 125 in Table 2)
(1) In a nitrogen atmosphere, 3.3 parts of benzenethiol and 1.9 parts of potassium hydroxide were dissolved in 70 parts of toluene, and the mixture was refluxed under heat. After stirred for 4 hours, the solution was allowed to cool, and the precipitated solid was filtered. Then, under a nitrogen stream, the precipitate, 3.5 parts of 1,5-dichloroanthraquinone and 0.6 part of copper powder were dissolved in 20 parts of DMF and refluxed under heat for 3 hours. The reaction solution obtained was poured into an aqueous potassium hydroxide solution, and the precipitated solid was filtered, washed, and dried. Then, after removal of inorganic materials with toluene, the solid obtained was recrystallized from 2-ethoxyethanol, filtered, washed, and dried, to give 3.1 parts of 1,5-bis(phenylthio)anthraquinone as an intermediate.

(2) A mixture of 1 part of the intermediate obtained, 12 parts of anhydrous aluminum chloride, 1.2 parts of hydroquinone, and 2.4 parts of sodium chloride was stirred under heat at 130° C. for 150 minutes. Dilute hydrochloric acid was added to the reaction product obtained, and the precipitated solid was filtered and washed with an aqueous hydrosulfite-sodium hydroxide solution. The solid obtained was purified by silica gel chromatography and then crystallized from toluene, to give 0.1 part of a desired compound (compound No. 125). The molecular weight of the compound was 390.

Mass spectrometric value: 390
Absorption maximum ($3.3 \times 10^{-4}$ M, in DMF): 536 nm
Emission maximum at an excitation wavelength of 577 nm ($3.3 \times 10^{-4}$ M, in DMF): 618 nm Synthesis Example 3

A compound No. 55 was prepared according to the method described in J. Chem. Soc., (1956), 2652.
In a 50-ml four-necked flask equipped with a stirrer, a thermometer, and a reflux condenser, placed were 13.5 parts of anhydrous aluminum chloride, 2.7 parts of sodium chloride, and 1 part of 1,5-bis-(1-naphthyloxy)anthraquinone obtained in Example 1(1), and the mixture was stirred under heat at 180° C. for 10 minutes and additionally at 145° C. for 15 minutes. Dilute hydrochloric acid was added to the reaction product, and the precipitated solid was filtered and washed with an aqueous hydrosulfite-sodiumhydroxide solution. The solid obtained was purified by silica gel chromatography and then crystallized from toluene, to give 0.1 part of powder. The molecular weight of the compound was 458. The mass spectrum revealed presence of the desired product as well as a by product chloride. Derivatives of the desired products with one and two molecules of chlorine were indicated in parenthesis respectively as Cl and $Cl_2$ after the following mass spectrometric value (the same shall apply hereinafter).

Mass spectrometric value: 458, 492(Cl), 526($Cl_2$)
Melting point: 278 to 293° C.

Example 1

(Synthesis of Compound No. 55 by the Production Method According to the Invention)
(1) Under a nitrogen atmosphere, 50 parts of 1-naphthol and 17 parts of potassium hydroxide were dissolved in 500 parts of toluene, and the mixture was refluxed under heat. After stirred for 4 hours, the solution was allowed to cool, and the precipitated solid was filtered. Then, under a nitrogen stream, the precipitate obtained, 24 parts of 1,5-dichloroanthraquinone and 7.2 parts of copper powder were dissolved in 500 parts of DMF, and the mixture was refluxed under heat for 5 hours. The reaction solution poured into an aqueous potassium hydroxide solution, and the precipitated solid was filtered, washed, and dried. Then, after removal of inorganic materials with toluene, the solid obtained was recrystallized from 2-ethoxyethanol, filtered, washed, and dried, to give 21 parts of 1,5-bis(1-naphthyloxy)anthraquinone as an intermediate.

(2) In a 500-ml four-necked flask equipped with a stirrer, a thermometer, and a reflux condenser, placed were 84 parts sulfuric acid, 126 parts acetic acid, and 21 parts of the intermediate obtained in (1), and the mixture was stirred under heat at 135° C. for 4 hours. The reaction solution was poured into 1.2 L of ice water. After stirring for 30 minutes, the precipitated solid was filtered and washed with an aqueous hydrosulfite-sodiumhydroxide solution. The solid obtained was purified by silica gel chromatography and then crystallized from toluene, to give 2 parts of a desired compound (compound No. 55). The molecular weight of the compound was 458. Analysis by mass spectrometry, $^1$H-NMR, and others confirmed that the desired product was provided at high purity.

Mass spectrometric value: 458
Melting point: 331 to 332° C.
$^1$H-NMR (CDCl$_3$, TMS): 7.10 (d, 2H), 7.40 (dd, 2H), 7.52-7.65 (m, 6H), 7.84 (dd, 2H), 8.18 (d, 2H), 8.28 (d, 2H), and 8.52 (dd, 2H)
Absorption maximum ($3.3 \times 10^{-4}$M, in DMF): 572 nm,
Emission maximum at an excitation wavelength of 587 nm ($3.3 \times 10^{-4}$M, in DMF): 607 nm, 641 nm Synthesis Example 4

(Synthesis of Compound No. 51)

A compound No. 51 was prepared according to the method described in J. Chem. Soc., (1956), 2652.

In a 50-ml four-necked flask equipped with a stirrer, a thermometer, and a reflux condenser, placed were 13.5 parts of anhydrous aluminum chloride, 2.7 parts of sodium chloride, and 1 part of 1,5-bis(2-naphthyloxy)anthraquinone obtained in Example 2(1) below, and the mixture was stirred under heat at 180° C. for 10 minutes and additionally at 145° C. for 15 minutes. Dilute hydrochloric acid was added to the reaction product, and the precipitated solid was filtered and washed with an aqueous hydrosulfite-sodiumhydroxide solution. The solid obtained was purified by silica gel chromatography and then crystallized from toluene, to give 0.1 parts of powder. The molecular weight of the compound was 458. The mass spectrum revealed presence of a desired product and a by product chloride.

Mass spectrometric value: 458, 492 (Cl)

Example 2

(Synthesis of Compound No. 51 by the Production Method According to the Invention)

(1) Under a nitrogen atmosphere, 50 parts of 2-naphthol and 17 parts of potassium hydroxide were dissolved in 500 parts of toluene, and the mixture was refluxed under heat. After stirred for 4 hours, the solution was allowed to cool, and the precipitated solid was filtered. Then, under a nitrogen stream, the precipitate, 24 parts of 1,5-dichloroanthraquinone and 7.2 parts of copper powder were dissolved in 500 parts of DMF, and the mixture was refluxed under heat for 5 hours. The reaction solution poured into an aqueous potassium hydroxide solution, and the precipitated solid was filtered, washed, and dried. Then, after removal of inorganic materials with toluene, the solid obtained was recrystallized from 2-ethoxyethanol, filtered, washed, and dried, to give 19 parts of 1,5-bis(2-naphthyloxy)anthraquinone as an intermediate.

(2) In a 30-ml four-necked flask equipped with a stirrer, a thermometer, and a reflux condenser, placed were 25 parts of methanesulfonic acid and 1 part of the intermediate obtained (1), and the mixture was stirred under heat at 140° C. for 5 hours. The reaction solution was poured into 200 ml of ice water, and after the mixture was stirred for 30 minutes, the precipitated solid was filtered and washed with an aqueous hydrosulfite-sodium hydroxide solution. The solid obtained was purified by silica gel chromatography and then crystallized from toluene, to give 0.1 part of a desired compound. The molecular weight of the compound was 458. Analysis by mass spectrometry, $^1$H-NMR, and others confirmed that the desired product was provided at high purity.

Mass spectrometric value: 458
$^1$H-NMR (CDCl$_3$, TMS): 7.09 (d, 2H), 7.58 (d, 2H), 7.31 (dd, 2H), 7.41 (dd, 2H), 7.51 (dd, 2H), 7.59 (d, 2H), 7.72 (d, 2H), 8.01 (d, 2H), and 8.09(d, 2H)
Absorption maximum ($1.3 \times 10^{-5}$M, in DMF): 566 nm,
Emission maximum at an excitation wavelength of 568 nm ($1.3 \times 10^{-5}$M, in DMF): 606 nm Condensed polycyclic compounds relatively higher in purity with a smaller amount of by products were obtained and more easily purified in Examples 1 and 2 than in Synthesis Examples 3 and 4. In addition, as the reaction was carried out in a solvent, it was possible to improve workability drastically and expand the scale of the reaction.

Example 3

(Synthesis of Compound No. 9 in Table 1: a Compound According to the Invention Represented by Formula (5))

(1) Under a nitrogen atmosphere, 4.3 parts of 4-phenylphenol and 1.5 parts of potassium hydroxide were dissolved in 80 parts of toluene and the solution was refluxed under heat. After stirred for 5 hours, the solution was allowed to cool, and the precipitated solid was filtered. Then, under a nitrogen stream, the precipitate, 2 parts of 1,5-dichloroanthraquinone and 0.6 part of copper powder were dissolved in 10 parts of DMF, and the mixture was refluxed under heat for 3 hours. The reaction solution was poured into an aqueous potassium-hydroxide solution, and the precipitated solid was filtered, washed, and dried. Then, after removal of inorganic materials with toluene, the solid obtained was recrystallized from 2-ethoxyethanol, filtered, washed, and dried, to give 0.6 part of 1,5-bis(4-phenylphenoxy)anthraquinone as an intermediate.

(2) A mixture of 0.6 part of the intermediate obtained, 6 parts of anhydrous aluminum chloride, 0.7 part of hydroquinone and 1.2 parts of sodium chloride was stirred under heat at 180° C. for 10 minutes and additionally at 160° C. for 15 minutes. Dilute hydrochloric acid was added to the reaction product, and the precipitated solid was filtered and washed with an aqueous hydrosulfite-sodiumhydroxide solution. The solid obtained was purified by silica gel chromatography and then crystallized from toluene, to give 0.1 part of a desired compound (compound No. 9). The molecular weight of the compound was 510.

Mass spectrometric value: 510 (as determined in SSQ-7000 manufactured by ThermoQuest, the same shall apply hereinafter).

Absorption maximum ($3.3 \times 10^{-4}$M, in DMF): 521 nm, 558 nm
Emission maximum at an excitation wavelength of 585 nm ($3.3 \times 10^{-4}$M, in DMF): 604 nm, 630 nm Example 4

(Synthesis of Compound No. 10 in Table 1: a Compound According to the Invention Represented by Formula (5))

Three parts of an intermediate [1,5-bis(2-phenylphenoxy)anthraquinone] was prepared in a similar manner to Example 3 except that 4-phenylphenol used in the preparation of compound No. 9 was replaced with 2-phenylphenol; and then, 0.1 part of a desired compound (compound No. 10) was prepared similarly from 1 part of the intermediate obtained. The molecular weight of the compound was 510.

Mass spectrometric value: 510

Absorption maximum ($3.3 \times 10^{-4}$M, in DMF): 518 nm, 554 nm

Emission maximum at an excitation wavelength of 581 nm ($3.3 \times 10^{-4}$M, in DMF): 601 nm, 624 nm Example 5

(Synthesis of Compound No. 39 by the Production Method According to the Invention: a Compound According to the Invention Represented by Formula (5))

(1) Under a nitrogen atmosphere, 1 part of 2,4-diphenylphenol and 0.8 part of potassium hydroxide were dissolved in 60 parts of toluene, and the solution was refluxed under heat. After stirred for 5 hours, the solution was allowed to cool, and the precipitated solid was filtered. Then, under a nitrogen stream, the precipitate obtained, 1 part of 1,5-dichloroanthraquinone and 0.3 part of copper powder were dissolved in 10 parts of DMF, and the mixture was refluxed under heat for 3 hours. The reaction solution poured into an aqueous potassium hydroxide solution, and the precipitated solid was filtered, washed, and dried. Then, after removal of inorganic materials with toluene, the solid obtained was recrystallized from toluene, filtered, washed, and dried, to give 1.3 parts of an intermediate.

(2) 1.2 parts of the intermediate obtained was added to 30 parts of methanesulfonic acid, and the mixture was stirred under heat at 130° C. for 3 hours. The reaction solution poured into 100 ml of ice water, and after the mixture was stirred for 30 minutes, the precipitated solid was filtered and washed with an aqueous hydrosulfite-sodiumhydroxide solution. The solid obtained was purified by silica gel chromatography and then crystallized from toluene, to give 0.5 part of a desired compound (compound No. 39).

Mass spectrometry: M=662 (mw=662) (as determined in SSQ-7000 manufactured by ThermoQuest)

$^1$H-NMR (CDCl$_3$, TMS): 6.90 (d, 2H), 7.33-7.80 (m, 24H), 8.24 (d, 2H), and 8.43 (d, 1H)

Absorption maximum ($3.3 \times 10^{-5}$M, in DMF): 553 nm

Emission maximum at an excitation wavelength of 557 nm ($3.3 \times 10^{-5}$M, in DMF): 584 nm Example 6

(Synthesis of Compound No. 40 by the Production Method According to the Invention: a Compound According to the Invention Represented by Formula (5))

(1) Under a nitrogen atmosphere, 3.2 parts of 4-fluorophenol and 1.6 parts of potassium hydroxide were dissolved in 40 parts of toluene, and the solution was refluxed under heat. After stirred for 5 hours, the solution was allowed to cool, and the precipitated solid was filtered. Then, under a nitrogen stream, the precipitate, 1 part of 1,5-dichloroanthraquinone and 0.5 part of copper powder were dissolved in 20 parts of DMF, and the mixture was refluxed under heat for 3 hours. The reaction solution poured into an aqueous potassium hydroxide solution, and the precipitated solid was filtered, washed, and dried. Then, after removal of inorganic materials with toluene, the solid obtained was recrystallized from toluene, filtered, washed, and dried, to give 2 parts of an intermediate.

(2) 1.5 parts of the intermediate obtained was added to 37 parts of methanesulfonic acid, and the mixture was stirred under heat at 140° C. for 4 hours. The reaction solution was poured into 200 ml of ice water, and after the mixture was stirred for 30 minutes, the precipitated solid was filtered and washed with an aqueous hydrosulfite-sodium hydroxide solution. The solid obtained was purified by silica gel chromatography and then crystallized from toluene, to give 0.4 part of a desired compound (compound No. 40).

Mass spectrometry: M=394 (mw=394) (as determined in SSQ-7000 manufactured by ThermoQuest)

$^1$H-NMR (CDCl$_3$, TMS): 6.97 (d, 2H), 7.01-7.08 (m, 2H), 7.15-7.20 (m, 2H), 7.42 (dd, 2H), 7.90-7.95 (m, 2H), and 8.09 (d, 2H)

Absorption maximum ($3.3 \times 10^{-5}$M, in DMF): 552 nm

Emission maximum at an excitation wavelength of 553 nm ($3.3 \times 10^{-5}$M, in DMF): 580 nm Example 7

(Synthesis of Compound No. 97 by the Production Method According to the Invention: a Compound According to the Invention Represented by Formula (5))

(1) Under a nitrogen atmosphere, 5.2 parts of 4-chloro-1-naphthol and 1.5 parts of potassium hydroxide were dissolved in 50 parts of toluene, and the solution was refluxed under heat. After stirred for 5 hours, the solution was allowed to cool, and the precipitated solid was filtered. Then, under a nitrogen stream, the precipitate, 1 part of 1,5-dichloroanthraquinone and 0.5 part of copper powder were dissolved in 20 parts of DMF, and the mixture was refluxed under heat for 3 hours. The reaction solution poured into an aqueous potassium hydroxide solution, and the precipitated solid was filtered, washed, and dried. Then, after removal of inorganic materials with toluene, the solid obtained was recrystallized from toluene and, filtered, washed, and dried, to give 1.9 parts of an intermediate.

(2) One part of the intermediate obtained was added to 25 parts of methanesulfonic acid, and the mixture was stirred under heat at 150° C. for 3 hours. The reaction solution was poured into 150 ml of ice water, and after the mixture was stirred for 30 minutes, the precipitated solid was filtered and washed with an aqueous hydrosulfite-sodium hydroxide solution. The solid obtained was purified by silica gel chromatography and then crystallized from toluene, to give 0.2 part of a desired compound (compound No. 97).

Absorption maximum ($3.3 \times 10^{-5}$M, in DMF): 580 nm

Emission maximum at an excitation wavelength of 582 nm ($3.3 \times 10^{-5}$M, in DMF): 607 nm Example 8

(Synthesis of Compound No. 43 by the Production Method According to the Invention: a Compound According to the Invention Represented by Formula (5))

(1) Under a nitrogen atmosphere, 13 parts of 4-bromophenol and 4 parts of potassium hydroxide were dissolved in 100 parts of toluene, and the solution was refluxed under heat. After stirred for 5 hours, the solution was allowed to cool, and the precipitated solid was filtered. Then, under a nitrogen stream, the precipitate, 5 parts of 1,5-dichloroanthraquinone and 2 parts of copper powder were dissolved in 100 parts of DMF, and the mixture was refluxed under heat for 3 hours. The reaction solution poured into an aqueous potassium hydroxide solution, and the precipitated solid was filtered, washed, and dried. Then, after removal of inorganic materials with toluene, the solid obtained was recrystallized from toluene and, filtered, washed, and dried, to give 2 parts of an intermediate.

(2) 1 part of the intermediate obtained was added to 25 parts of methanesulfonic acid, and the mixture was stirred under heat at 150° C. for 2.5 hours. The reaction solution poured into 100 ml of ice water, and after the mixture was stirred for 30 minutes, the precipitated solid was filtered and washed with an aqueous hydrosulfite-sodiumhydroxide solution. The solid obtained was purified by silica gel chromatography and then crystallized from toluene, to give 0.1 part of a desired compound (compound No. 43).

Mass spectrometry: M=516 (mw=516) (as determined in SSQ-7000 manufactured by ThermoQuest)

Absorption maximum ($3.3 \times 10^{-5}$M, in DMF): 553 nm

Emission maximum at an excitation wavelength of 555 nm ($3.3 \times 10^{-5}$M, in DMF): 579 nm Example 9

(Synthesis of Compound No. 93 by the Production Method According to the Invention: a Compound According to the Invention Represented by Formula (5))

(1) Under a nitrogen atmosphere, 4.5 parts of 4-fluoro-4'-hydroxybiphenyl, 1.3 parts of potassiumhydroxide, and 1.7 parts of 1,4-dichloroanthraquinone were dissolved in 20 parts of DMF, and the solution was stirred under heat at 130° C. for 3 hours. The reaction solution was poured into water, and the precipitated solid was filtered, washed, and dried, to give 2.6 parts of 1,4-bis(4-(4'-fluorophenyl)phenoxyanthraquinone).

(2) 2.6 parts of 1,4-bis(4-(4'-fluorophenyl)phenoxyanthraquinone) obtained in (1) was added to 60 parts of methanesulfonic acid, and the mixture was stirred under heat at 110° C. for 3 hours. The reaction solution was poured into 200 ml of ice water, and after the mixture was stirred for 30 minutes, the precipitated solid was filtered and washed with an aqueous hydrosulfite-sodium hydroxide solution. The solid obtained was purified by silica gel chromatography and then crystallized from toluene, to give 0.2 part of a desired compound (compound No. 93). Analysis by mass spectrometry, $^1$H-NMR, and others confirmed that the desired product was provided at high purity.

Mass spectrometry: M=546 (mw=546) (as determined in SSQ-7000 manufactured by ThermoQuest)

$^1$H-NMR (CDCl$_3$, TMS): 6.99 (d, 2H), 7.16 (dd, 4H), 7.35-7.64 (m, 12H), 8.19 (d, 2H), and 8.55-8.36 (s, 2H)

Example 10

(Preparation of the Derivative (Intermediate) of Formula (15), Compound No. 126: a Compound According to the Invention Represented by Formula (6))

(1) 10 parts of 1,5-bis(4-bromophenoxy)anthraquinone, 8 parts of potassium hydroxide, and 9 parts of 4-toluenethiol were added to 100 parts of DMF, and the mixture was stirred under heat at 110° C. for 3 hours. The precipitated solid after cooling was filtered, washed, and dried, to give 6.5 parts of an intermediate (1,5-bis(4-methylphenylthio)anthraquinone).

(2) A mixture of 6.5 parts of the intermediate, 73 parts of anhydrous aluminum chloride, 7.3 parts of hydroquinone, and 15 parts of sodium chloride was stirred under heat at 130° C. for 150 minutes. Water was added to the reaction product, and the precipitated solid was filtered and washed with an aqueous hydrosulfite-sodiumhydroxide solution. The solid obtained was purified by silica gel chromatography and then crystallized from toluene, to give 1.6 part of a desired compound (compound No. 126).

Mass spectrometry: M=418 (mw=418) (as determined in SSQ-7000 manufactured by ThermoQuest)

$^1$H-NMR (CDCl$_3$, TMS): 2.40 (s, 6H), 7.06 (d, 2H), 7.20-7.39 (m, 6H), 7.71 (d, 2H), and 8.12(d, 2H)

Absorption maximum ($1.0 \times 10^{-5}$M, in DMF): 537 nm

Emission maximum ($1.0 \times 10^{-5}$M, in DMF): 609 nm

Example 11

(Synthesis of Compound No. 129: a Compound According to the Invention Represented by Formula (6))

A mixture of 10 parts of 1,5-bis(2-methylphenylthio)anthraquinone and 112 parts of anhydrous aluminum chloride, 11 parts of hydroquinone and 24 parts of sodium chloride were stirred under heat at 130° C. for 150 minutes. Water was added to the reaction product, and the precipitated solid was filtered and washed with an aqueous hydrosulfite-sodiumhydroxide solution. The solid obtained was purified by silica gel chromatography and then crystallized from toluene, to give 2.4 parts of a desired compound (compound No. 129).

Mass spectrometry: M=418 (mw=418) (as determined in SSQ-7000 manufactured by ThermoQuest)

$^1$H-NMR (CDCl$_3$, TMS): 2.80 (s, 6h), 7.06 (s, 2H), 7.19-7.37 (m, 6H), 7.70 (d, 2H), and 8.13 (d, 2H)

Absorption maximum ($1.1 \times 10^{-5}$M, in DMF): 537 nm

Emission maximum ($1.1 \times 10^{-5}$M, in DMF): 610 nm

Example 12

(Synthesis of Compound No. 133: a Compound According to the Invention Represented by Formula (6))

A mixture of 1 part of 1,5-bis(4-phenylphenylthio)anthraquinone, 12 parts of anhydrous aluminum chloride, 7.3 parts hydroquinone, and 15 parts sodium chloride were stirred under heat at 130° C. for 150 minutes. Water was added to the reaction product, and the precipitated solid was filtered and washed with an aqueous hydrosulfite-sodiumhydroxide solution. The solid obtained was purified by silica gel chromatography and then crystallized from toluene, to give 0.2 parts of a desired compound (compound No. 133).

Mass spectrometry: M=542 (mw=542) (as determined in SSQ-7000 manufactured by ThermoQuest)

Absorption maximum ($1.1 \times 10^{-5}$ M, in DMF): 555 nm

Emission maximum ($1.1 \times 10^{-5}$ M, in DMF): 637 nm

Example 13

(Synthesis of Compound No. 134: a Compound According to the Invention Represented by Formula (6))

A mixture of parts of 1,5-bis(2-phenylphenylthio)anthraquinone, 48 parts of anhydrous aluminum chloride, 4.8 parts of hydroquinone and 9.4 parts of sodium chloride were stirred under heat at 130° C. for 150 minutes. Water was added to the reaction product, and the precipitated solid was filtered and washed with an aqueous hydrosulfite-sodium hydroxide solution. The solid obtained was purified by silica gel chromatography and then crystallized from toluene, to give 0.9 part of a desired compound (compound No. 134).

Mass spectrometry: M=542 (mw=542) (as determined in SSQ-7000 manufactured by ThermoQuest)

$^1$H-NMR (CDCl$_3$, TMS): 7.30 (m, 2H), 7.41 (m, 4H), 7.49 (m, 6H), 7.67 (m, 6H), 7.90 (d, 2H), and 8.21 (d, 2H)

Absorption maximum ($1.0 \times 10^{-5}$M, in DMF): 553 nm

Emission maximum ($1.0 \times 10^{-5}$M, in DMF): 635 nm

Example 14

(Synthesis of Compound No. 311 by the Production Method According to the Invention: a Compound According to the Invention Represented by Formula (7))

(1) Under a nitrogen atmosphere, 6 parts of 4-phenylphenol and 1.8 parts of potassium hydroxide were dissolved in 60 parts of toluene, and the solution was refluxed under heat. After stirred for 5 hours, the solution was allowed to cool, and the precipitated solid was filtered. Then, under a nitrogen stream, the precipitate obtained, 2.5 parts of 1,4-dichloroanthraquinone and 0.9 part of copper powder were dissolved in 20 parts of DMF, and the mixture was refluxed under heat for 3 hours. There action solution poured into an aqueous potassium hydroxide solution, and the precipitated solid was filtered, washed, and dried. Then, after removal of inorganic materials with toluene, the solid obtained was recrystallized from 2-ethoxyethanol, filtered, washed, and dried, to give 2 parts of 1,4-bis-(4-phenylphenoxyanthraquinone).

(2) Two parts of 1,4-bis-(4-phenylphenoxyanthraquinone) obtained in (1) above mentioned was added to 50 parts of methanesulfonic acid, and the mixture was stirred under heat at 110° C. for 3 hours. The reaction solution was poured into 200 ml of ice water, and after the mixture was stirred for 30 minutes, the precipitated solid was filtered and washed with an aqueous hydrosulfite-sodium hydroxide solution. The solid obtained was purified by silica gel chromatography and then crystallized from toluene, to give 0.1 part of a desired compound (compound No. 311 in Table 5). Analysis by mass spectrometry, $^1$H-NMR, and others confirmed that the desired product was provided at high purity.

Mass spectrometry: M=510 (mw=510) (as determined in SSQ-7000 manufactured by ThermoQuest)

$^1$H-NMR (CDCl$_3$, TMS): 6.74 (s, 2H), 7.15 (d, 2H), 7.35-7.53 (m, 10H), 7.57-7.64 (m, 4H), 8.18 (d, 2H), and 8.55-8.63 (m, 2H)

Absorption maximum ($3.3 \times 10^{-4}$M, in DMF): 610 nm

Emission maximum at an excitation wavelength of 610 nm ($3.3 \times 10^{-4}$M, in DMF): 646 nm

Example 15

(Thermal Analysis of the Compounds According to the Invention)

Thermal analysis of the compounds for use in the device according to the invention was performed by using a differential scanning calorimeter (DSC). The melting point and, if possible, the Tg point of each compound were determined. Measurement results are summarized in Table 9.

TABLE 9

| Compound No. | Tg point (° C.) | Melting point (° C.) |
|---|---|---|
| 1 | 74 | 265 |
| 2 | 90 | 282 |
| 9 | 118 | 234 |
| 10 | 124 | 287 |
| 40 | — | 345 |
| 41 | — | 354 |
| 43 | — | 373 |
| 51 | 162 | 265 |
| 55 | 115 | 331 |
| 93 | — | 343 |
| 95 | 121 | 277 |
| 96 | 162 | 291 |
| 99 | 163 | 296 |

As apparent from the results, the compounds according to the invention showed increase in melting point and Tg point by incorporation of a halogen atom, an aliphatic hydrocarbon residue which may be substituted, or an aromatic residue which may be substituted. In particular, the compounds represented by Formula (5) became more thermally stable by incorporation of a halogen atom or an aromatic residue which may be substituted. In addition, the compounds represented by Formula (6) became sufficiently thermally stable by incorporation of an aliphatic hydrocarbon residue which may be substituted. Accordingly, these compounds may be used favorably as organic electronic materials, in particular as the materials for organic EL devices, and would be effective for improvement in durability and the like.

Example 16

(Preparation and Evaluation of the Device Having Compound No. 1 as the Light-emitting Layer)

A glass substrate carrying an ITO transparent conductive film having a thickness of 150 nm thereon (manufactured by Tokyo Sanyo Vacuum Industries Co., Ltd., 14Ω/□ or less) was cut into pieces of 25×25 mm in size and etched. The substrate obtained was washed ultrasonically with a neutral detergent for 10 minutes, with ion-exchange water twice for 5 minutes, with acetone twice for 5 minutes, and additionally with isopropyl alcohol twice for 5 minutes, and cleaned with UV-ozone for 10 minutes immediately before preparation of a device. The cleaned substrate was placed in a vacuum metallizer, which was evacuated to a vacuum of $3.0 \times 10^{-4}$ Pa or less. A positive hole-injecting material, copper phthalocyanine, was first deposited to a thickness of 10 nm, and then a positive hole-transporting material, N,N'-dinaphthyl-N,N'-diphenyl-4,4'-diphenyl-1,1'-diamine (aNPD), was deposited to a thickness of 50 nm by the resistance-heating vapor deposition method, forming a positive hole-transporting layer. A light-emitting material, compound No. 1 in Table 1, was then deposited to a thickness of 30 nm, forming a light-emitting layer, and then tris(8-quinolinolato)aluminum (AlQ3) was deposited to a thickness of 30 nm as an electron-transporting layer. Further, a Mg—Ag alloy (91:9%) was deposited to a thickness of 200 nm as a cathode, to give a light-emitting device of 2×2 mm square.

The light-emitting device emitted a homogeneous light of 90 cd/m$^2$ without any dark spots at a voltage of 16 V. The emitted light was red orange at x: 0.57 and y: 0.41 in XYZ emission chromaticity coordinates (the same shall apply hereinafter).

Example 17

(Preparation and Evaluation of the Device Having Compound No. 1 as the Dopant for Light-emitting Layer)

A substrate processed in a similar manner to Example 16 was placed in a vacuum metallizer, which was evacuated to a vacuum of $3.0 \times 10^{-4}$ Pa or less. A positive hole-transporting material, N,N'-diphenyl-N,N'-a-naphthyl-1,1'-diphenyl-4,4'-diamine (a-NPD), was deposited to a thickness of 50 nm, forming a positive hole-transporting layer by the resistance-heating vapor deposition method. A host material for light-emitting material, tris(8-quinolinolato)aluminum (AlQ3) and a dopant, compound No. 1 (in an amount of 2.5% with respect to the host material) were deposited together to a thickness of 30 nm, forming a light-emitting layer. Then, tris(8-quinolinolato)aluminum (AlQ3) was deposited to a thickness of 30 nm as an electron-transporting layer. Then, a Mg—Ag alloy (91:9%) was deposited to a thickness of 200 nm, as a cathode, to give a light-emitting device of 2×2 mm square. The light-emitting device emitted a homogeneous light of 3,320 cd/m$^2$ without any dark spots at a voltage of 18 V. The emitted light at 100 cd/m$^2$ was orange at 0.55 and 0.45 in the XYZ emission chromaticity coordinates (see FIG. 1).

Example 18

(Preparation and Evaluation of the Device Having Compound No. 3 as the Dopant for Light-emitting Layer)

A light-emitting device was prepared in a similar manner to Example 17, except that compound No. 1 used as the dopant for light-emitting material was replaced with compound No. 3. The light-emitting device emitted a homogeneous light of 432 cd/m$^2$ without any dark spots at a voltage of 20 V. The emitted light at 100 cd/m$^2$ was orange at 0.55 and 0.45 in the XYZ emission chromaticity coordinates.

Example 19

(Preparation and Evaluation of the Device Having Compound No. 9 as the Dopant for Light-emitting Layer)

A light-emitting device was prepared in a similar manner to Example 17, except that compound No. 1 used as the dopant for light-emitting material was replaced with compound No. 9. The light-emitting device emitted a homogeneous light of 3,480 cd/m$^2$ without any dark spots at a voltage of 16 V. The emitted light at 100 cd/m$^2$ was red orange at 0.62 and 0.37 in the XYZ emission chromaticity coordinates.

Example 20

(Preparation and Evaluation of the Device Having Compound No. 9 as Light-emitting Layer)

A substrate processed in a similar manner to Example 16 was placed in a vacuum metallizer, which was evacuated to a vacuum of 3.0×10$^{-4}$ Pa or less. A positive hole-transporting material, N,N'-diphenyl-N,N'-a-naphthyl-1,1'-diphenyl-4,4'-diamine (a-NPD), was deposited to a thickness of 50 nm, forming a positive hole-transporting layer by the resistance-heating vapor deposition method. A light-emitting material, compound No. 9 in Table 1, was then deposited to a thickness of 30 nm and tris(8-quinolinolato)aluminum (AlQ3) was deposited to a thickness of 30 nm as an electron-transporting layer. Then, a Mg—Ag alloy (91:9%) was deposited to a thickness of 200 nm as a cathode, to give a light-emitting device of 2×2 mm square. The light-emitting device emitted a homogeneous light of 98 cd/m$^2$ without any dark spots at a voltage of 18 V. The emitted light was red at 0.63 and 0.36 in the XYZ emission chromaticity coordinates.

Example 21

(Preparation and Evaluation of the Device Having Compound No. 55 as the Dopant for Light-emitting Layer)

A light-emitting device was prepared in a similar manner to Example 17, except that compound No. 1 used as the dopant for light-emitting material was replaced with compound No. 55. The light-emitting device emitted a homogeneous light of 1,220 cd/m$^2$ without any dark spots at a voltage of 17 V. The emitted light at 100 cd/m$^2$ was red at 0.65 and 0.35 in the XYZ emission chromaticity coordinates.

Example 22

(Preparation and Evaluation of the Device Having Compound No. 51 as the Dopant for Light-emitting Layer)

A light-emitting device was prepared in a similar manner to Example 17, except that compound No. 1 used as the dopant for light-emitting material was replaced with the compound No. 51 obtained in Synthesis Example 4. The light-emitting device emitted a homogeneous light of 1,230 cd/m$^2$ without any dark spots at a voltage of 19 V. The emitted light at 100 cd/m$^2$ was red at 0.63 and 0.36 in the XYZ emission chromaticity coordinates.

Example 23

(Preparation and Evaluation of the Device Having Compound No. 51 Obtained According to the Method Described in Literature as the Dopant for Light-emitting Layer)

A light-emitting device was prepared in a similar manner to Example 22, except that the compound No. 51 obtained in Synthesis Example 4 was used as the dopant for light-emitting material in an amount of 1% with respect to the host material. The light-emitting device emitted a homogeneous light of 4,030 cd/m$^2$ without any dark spots at a voltage of 16 V. The emitted light at 100 cd/m$^2$ was red at 0.61 and 0.37 in the XYZ emission chromaticity coordinates.

Example 24

(Preparation and Evaluation of the Device Having Compound No. 51 Obtained According to the Production Method of the Invention as the Dopant for Light-emitting Layer)

A light-emitting device was prepared in a similar manner to Example 23, except that the compound No. 51 obtained in Example 2 was used as the dopant for light-emitting material in an amount of 1% with respect to the host material. The light-emitting device emitted a homogeneous light of 4,320 cd/m$^2$ without any dark spots at a voltage of 16 V. The emitted light at 100 cd/m$^2$ was red at 0.64 and 0.36 in the XYZ emission chromaticity coordinates.

Comparison of Examples 23 and 24 suggests that the compound obtained by the production method according to the invention is more favorable as it is more effective in improvement in brightness and red shift of emission color.

Example 25

(Preparation and Evaluation of the Device Having Compound No. 55 as the Dopant for Light-emitting Layer)

A light-emitting device was prepared in a similar manner to Example 17, except that AlQ3 used as host material for light-emitting material was replaced with the compound No. 537 represented by the following Formula and compound No. 1 used as a dopant with compound No. 55. The light-emitting device emitted a homogeneous light of 233 cd/m$^2$ without any dark spots at a voltage of 15 V. The emitted light was red at 0.66 and 0.34 in the XYZ emission chromaticity coordinates.

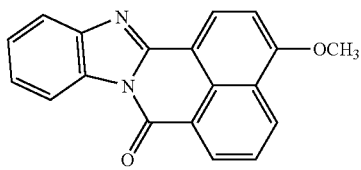

No. 537

Example 26

(Preparation and Evaluation of the Device Having Compound No. 10 as the Dopant for Light-emitting Layer)

A light-emitting device was prepared in a similar manner to Example 17, except that compound No. 1 used as the dopant for light-emitting material was replaced compound No. 10 with Table 1. The light-emitting device emitted a homogeneous light of 2,400 cd/m$^2$ without any dark spots at a voltage of 18 V. The emitted light at 100 cd/m$^2$ was red orange at 0.62 and 0.38 in the XYZ emission chromaticity coordinates.

Example 27

(Preparation and Evaluation of the Device Having Compound No. 125 as the Dopant for Light-emitting Layer)

A light-emitting device was prepared in a similar manner to Example 17, except that compound No. 1 used as the dopant for light-emitting material was replaced with compound No. 125. The light-emitting device emitted a homogeneous light of 2,810 cd/m$^2$ without any dark spots at a voltage of 19 V. The emitted light at 100 cd/m$^2$ was red orange at 0.64 and 0.36 in the XYZ emission chromaticity coordinates.

Example 28

(Preparation and Evaluation of the Device Having Compound No. 125 as Light-emitting Layer)

A light-emitting device was prepared in a similar manner to Example 20, except that compound No. 9 used as light-emitting material was replaced with compound No. 125. The light-emitting device emitted a homogeneous light of 136 cd/m$^2$ without any dark spots at a voltage of 17 V. The emitted light at 100 cd/m$^2$ was red orange at 0.63 and 0.35 in the XYZ emission chromaticity coordinates.

Example 29

(Preparation and Evaluation of the White Light-emitting Device Having Compound No. 9 as the Dopant for Light-emitting Layer)

On a substrate processed in a similar manner to Example 16, a positive hole-transporting material, N,N'-diphenyl-N, N'-a-naphthyl-1,1'-diphenyl-4,4'-diamine (a-NPD), was first deposited to a thickness of 50 nm, forming a positive hole-transporting layer by the resistance-heating vapor deposition method. Then, a host material for light-emitting material, 4,4'-bis(diphenylvinylenyl)-biphenyl (DPVBi), and a dopant, compound No. 9 (in an amount of 0.42% with respect to the host material), were deposited together to a thickness of 30 nm, forming a light-emitting layer, and then tris(8-quinolinolato)aluminum (AlQ3) was deposited to a thickness of 30 nm as an electron-transporting layer. Then, a Mg—Ag alloy (91: 9%) was deposited to a thickness of 200 nm as a cathode, to give a light-emitting device of 2×2 mm square. The light-emitting device emitted a homogeneous light of 13,500 cd/m$^2$ without any dark spots at a voltage of 18 V. The emitted light at 4,500 cd/m$^2$ was white at 0.38 and 0.35 in the XYZ emission chromaticity coordinates.

Example 30

(Preparation and Evaluation of the Device Having Compound No. 39 as the Dopant for Light-emitting Layer)

A light-emitting device was prepared in a similar manner to Example 17, except that the compound No. 1 used as the dopant for light-emitting material was replaced with compound No. 39 in an amount of 1% with respect to the host material. The light-emitting device emitted a homogeneous light of 22,400 cd/m$^2$ without any dark spots at a voltage of 18 V. The emitted light at 100 cd/m$^2$ was orange at 0.57 and 0.43 in the XYZ emission chromaticity coordinates.

Example 31

(Preparation and Evaluation of the Device Having Compound No. 40 as the Dopant for Light-emitting Layer)

A light-emitting device was prepared in a similar manner to Example 30, except that the compound No. 39 used as the dopant for light-emitting material was replaced with compound No. 40. The light-emitting device emitted a homogeneous light of 10,200 cd/m$^2$ without any dark spots at a voltage of 15 V. The emitted light at 100 cd/m$^2$ was orange at 0.59 and 0.41 in the XYZ emission chromaticity coordinates.

Example 32

(Preparation and Evaluation of the Device Having Compound No. 43 as the Dopant for Light-emitting Layer)

A light-emitting device was prepared in a similar manner to Example 30, except that the compound No. 39 used as the dopant for light-emitting material was replaced with compound No. 43. The light-emitting device emitted a homogeneous light of 8,000 cd/m$^2$ without any dark spots at a voltage of 15 V. The emitted light at 100 cd/m$^2$ was orange at 0.57 and 0.42 in the XYZ emission chromaticity coordinates.

Example 33

(Preparation and Evaluation of the Device Having Compound No. 97 as the Dopant for Light-emitting Layer)

A light-emitting device was prepared in a similar manner to Example 30, except that the compound No. 39 used as the dopant for light-emitting material was replaced with compound No. 97.

The light-emitting device emitted a homogeneous light of 4,420 cd/m$^2$ without any dark spots at a voltage of 16 V. The emitted light at 100 cd/m$^2$ was red at 0.63 and 0.35 in the XYZ emission chromaticity coordinates.

Example 34

(Preparation and Evaluation of the Device Having Compound No. 126 as the Dopant for Light-emitting Layer)

A light-emitting device was prepared in a similar manner to Example 30, except that the compound No. 39 used as the dopant for light-emitting material was replaced with compound No. 126 in an amount of 4 mass % with respect to the host material.

Example 35

(Preparation and Evaluation of the Device Having Compound No. 129 as the Dopant for Light-emitting Layer)

A light-emitting device was prepared in a similar manner to Example 34, except that the compound No. 126 used as the dopant for light-emitting material was replaced with compound No. 129.

The light-emitting device emitted a light having the maximum brightness of 3,320 cd/m$^2$ without any dark spots at a voltage of 16 V. The emitted light at 100 cd/m$^2$ was red at 0.65 and 0.35 in the XYZ emission chromaticity coordinates.

Example 36

(Preparation and Evaluation of the Device Having Compound No. 133 as the Dopant for Light-emitting Layer)

A light-emitting device was prepared in a similar manner to Example 34, except that the compound No. 126 used as the dopant for light-emitting material was replaced with compound No. 133 in an amount of 1.5% with respect to the host material.

The light-emitting device emitted a light having the maximum brightness of 3,160 cd/m$^2$ without any dark spots at a voltage of 17 V. The emitted light at 100 cd/$^2$was red at 0.65 and 0.34 in the XYZ emission chromaticity coordinates.

Example 37

(Preparation and Evaluation of the Device Having Compound No. 134 as the Dopant for Light-emitting Layer)

A light-emitting device was prepared in a similar manner to Example 34, except that the compound No. 126 used as the dopant for light-emitting material was replaced with compound No. 134 in an amount of 3% with respect to the host material.

The light-emitting device emitted a light having the maximum brightness of 1,740 cd/m$^2$ without any dark spots at a voltage of 18 V. The emitted light at 100 cd/m$^2$ was red at 0.66 and 0.34 in the XYZ emission chromaticity coordinates.

Example 38

(Preparation and Evaluation of the Device Having Compound No. 311 as the Dopant for Light-emitting Layer)

A light-emitting device was prepared in a similar manner to Example 17, except that the compound No. 1 used as the dopant for light-emitting material was replaced with compound No. 311.

The light-emitting device emitted a homogeneous light of 887 cd/m$^2$ without any dark spots at a voltage of 18 V. The emitted light at 100 cd/m$^2$ was red at 0.65 and 0.34 in the XYZ emission chromaticity coordinates.

Example 39

(Preparation and Evaluation of the Device Having Compound No. 10 as the Dopant for Light-emitting Layer)

A substrate processed in a similar manner to Example 16 was placed in a vacuum metallizer, which was evacuated to a vacuum of $3.0 \times 10^{-4}$ Pa or less. A positive hole-transporting material, N,N'-dinaphthyl-N,N'-diphenyl-4,4'-diphenyl-1,1'-diamine (aNPD), was deposited to a thickness of 50 nm, forming a positive hole-transporting layer by the resistance-heating vapor deposition method. Then, a host, 4,4'-bis(9-carbazolyl)-biphenyl, and a dopant, compound No. 10 (in an amount of 3% with respect to the host material), were co-deposited to a thickness of 30 nm as the light-emitting materials, forming a light-emitting layer. Tris(8-quinolinolato) aluminum (AlQ3) was then deposited thereon to a thickness of 30 nm as an electron-transporting layer. Then, a Mg—Ag alloy (91:9%) was deposited to a thickness of 200 nm as a cathode, to give a light-emitting device of 2×2 mm square.

The light-emitting device emitted a homogeneous light of 2,290 cd/m$^2$ without any dark spots at a voltage of 16 V. The emitted light at 100 cd/m$^2$ was yellow at 0.54 and 0.44 in the XYZ emission chromaticity coordinates.

Example 40

(Preparation and Evaluation of the Device Having Compound No. 10 as the Dopant for Light-emitting Layer)

A light-emitting device was prepared in a similar manner to Example 39, except that 4,4'-bis(9-carbazolyl)-biphenyl used as the host material for light-emitting material was replaced with 9,10-bis(2-naphthalenyl)anthracene. The light-emitting device emitted a homogeneous light of 5,400 cd/m$^2$ without any dark spots at a voltage of 15 V. The emitted light at the time was orange at 0.56 and 0.44 in the XYZ emission chromaticity coordinates.

Example 41

(Preparation and Evaluation of the Device Having Compound No. 10 as the Dopant for Positive Hole-transporting Light-emitting Layer)

A substrate processed in a similar manner to Example 16 was placed in a vacuum metallizer, which was evacuated to a vacuum of $3.0 \times 10^{-4}$ Pa or less. A host for positive hole-transporting light-emitting layer, N,N'-diphenyl-N,N'-a-naphthyl-1,1'-diphenyl-4,4'-diamine (a-NPD), and a dopant, compound No. 10, (in an amount of 3% with respect to the host material), were co-deposited to a thickness of 50 nm, by the resistance-heating vapor deposition method, forming a positive hole-transporting light-emitting layer. Tris(8-quinolinolato)aluminum (AlQ3) was then deposited to a thickness of 60 nm as an electron-transporting layer. Then, a Mg—Ag alloy (91:9%) was deposited to a thickness of 200 nm, as a cathode, to give a light-emitting device of 2×2 mm square. The light-emitting device emitted a homogeneous light of 15,400 cd/m$^2$ without any dark spots at a voltage of 17 V. The emitted light at 100 cd/m$^2$ was yellow orange at 0.55 and 0.45 in the XYZ emission chromaticity coordinates.

Example 42

(Preparation and Evaluation of the Device Having Compound No. 10 as the Dopant for Positive Hole-transporting Light-emitting Layer)

A light-emitting device was prepared in a similar manner to Example 41, except that compound No. 10 was co-deposited as the dopant for positive hole-transporting light-emitting layer in an amount of 50% with respect to the host material, forming a positive hole-transporting light-emitting layer. The light-emitting device emitted a homogeneous light of 2,280 cd/m² without any dark spots at a voltage of 16 V. The emitted light at 100 cd/m² was orange at 0.62 and 0.37 in the XYZ emission chromaticity coordinates.

The result indicates that the compound according to the invention functions as a dopant for positive hole-transporting light-emitting layer.

Example 43

(Preparation and Evaluation of the Device Having Compound No. 1 as Positive Hole-transporting and Light-emitting Layers)

A substrate processed in a similar manner to Example 16 was placed in a vacuum metallizer, which was evacuated to a vacuum of $3.0 \times 10^{-4}$ Pa or less. The compound No. 1 in Table 1 was deposited to a thickness of 40 nm as a positive hole-transporting layer and also as a light-emitting layer and tris (8-quinolinolato)aluminum (AlQ3) to a thickness of 60 nm as an electron-transporting layer by the resistance-heating vapor deposition method. Then, a Mg—Ag alloy (91:9%) was deposited to a thickness of 200 nm, as a cathode, to give a light-emitting device of 2×2 mm square. The light-emitting device emitted a homogeneous light of 546 cd/m² without any dark spots at a voltage of 15 V. The emitted light at 100 cd/m² was red at 0.64 and 0.35 in the XYZ emission chromaticity coordinates.

The result indicates that the compound according to the invention functions as a positive hole-transporting layer as well as a light-emitting layer.

Example 44

(Preparation and Evaluation of the Device Having Compound No. 1 as a Positive Hole-injecting Material)

A substrate processed in a similar manner to Example 16 was placed in a vacuum metallizer, which was evacuated to a vacuum of $3.0 \times 10^{-4}$ Pa or less. The compound No. 1 was deposited to a thickness of 10 nm as a positive hole-injecting material and then N,N'-dinaphthyl-N,N'-diphenyl-4,4'-diphenyl-1,1'-diamine (aNPD) to a thickness of 50 nm as a positive hole-transporting material, by the resistance-heating vapor deposition method, forming a positive hole-transporting layer. Then, tris(8-quinolinolato)aluminum (AlQ3) was deposited to a thickness of 60 nm as an electron-transporting light-emitting layer as alight-emitting material. Then, a Mg—Ag alloy (91:9%) was deposited to a thickness of 200 nm, as a cathode, to give a light-emitting device of 2×2 mm square.

Figure 2:
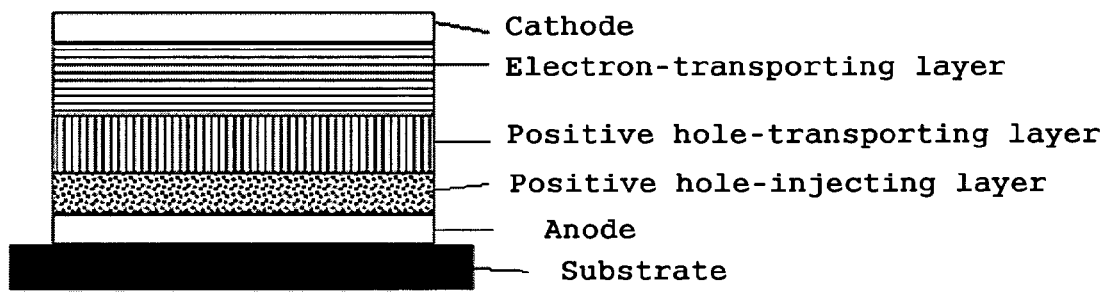

The light-emitting device emitted a homogeneous light of 15,000 cd/m² without any dark spots at a voltage of 14 V at the highest brightness. The current efficiency was 3.44 cd/A at 100 mA/cm², and the power efficiency 1.5 lm/W at 10 mA/cm². The threshold voltage when the luminescence brightness became 1 cd/m² or more was 4.5 V (see FIG. 2).

Examples 45 to 50

Light-emitting devices were prepared in a similar manner to Example 44. The compound No. 1 in Example 44 for the positive hole-injecting layer was replaced with the compound shown in the Table. Results are summarized in Table 9. Current efficiency (cd/A) is a value at 100 mA/cm², and the threshold voltage (V) is a voltage when the luminescence brightness becomes 1 cd/m² or more, and the power efficiency (lm/W) is a value at 10 mA/cm².

Comparative Examples 1 and 2

Light-emitting devices are prepared in a similar manner to Example 1. The compound No. 1 in Example 1 for the positive hole-injecting layer was replaced with copper phthalocyanine in Comparative Example 1, while the positive hole-injecting layer was not formed in Comparative Example 2. Results are summarized in Table 9.

TABLE 9

| | Compound No. | Current efficiency | Threshold voltage | Power efficiency |
|---|---|---|---|---|
| Example | | | | |
| 44 | 1 | 3.4 | 4.5 | 1.5 |
| 45 | 2 | 3.4 | 5.3 | 1.3 |
| 46 | 9 | 3.1 | 5.3 | 1.3 |
| 47 | 39 | 3.4 | 5.0 | 1.3 |
| 48 | 40 | 3.2 | 3.3 | 1.5 |
| 49 | 126 | 3.3 | 4.8 | 1.4 |
| 50 | 129 | 3.1 | 4.8 | 1.3 |
| Comparative Example | | | | |
| 1 | Copper phthalocyanine | 3.0 | 5.5 | 1.2 |
| 2 | None | 3.0 | 7.2 | 1.1 |

As apparent from comparison of the results in Examples and Comparative Examples, use of the compounds according to the invention leads to decrease in threshold voltage and increase in power efficiency, which in turn leads to decrease in the electric consumption of the device and improvement in stability of the light-emitting devices.

INDUSTRIAL APPLICABILITY

The light-emitting devices obtained by using the compounds according to the invention emit orange or red light higher in color purity and sufficiently higher in brightness even at low energy application. In addition, the device, which operates at low voltage, provides light-emitting devices higher in luminous efficiency. Further, the compounds for use in the invention, which are favorable in coating properties, provides light-emitting devices having practical stability and lifetime.

The invention claimed is:

1. A light-emitting device emitting light by electric energy having one or more layers of organic thin films formed between an anode and a cathode, characterized in that the organic thin film contains a compound represented by the following General Formula (3) or (4):

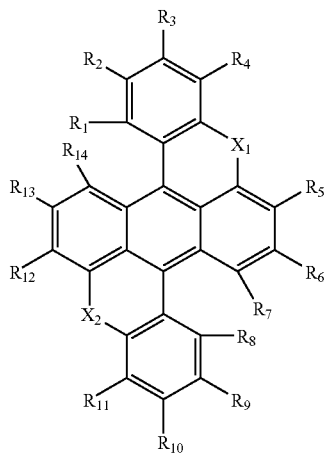

(3)

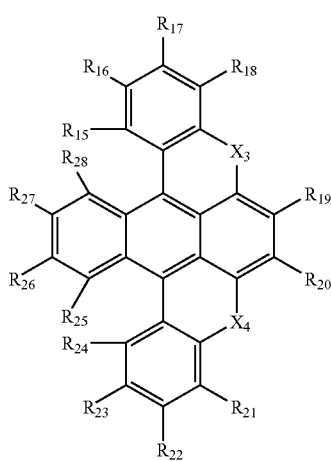

(4)

(wherein, $X_1$, $X_2$, $X_3$ and $X_4$ each independently represent an oxygen, sulfur, selenium, or tellurium atom, or $NR_{29}$; and $R_{29}$ represents a hydrogen atom, an alkyl group having 1 to 6 carbon atoms which may be substituted with at least one group selected from the group consisting of a halogen atom, phenyl, biphenyl, naphthyl, pyridino, thienyl, and furyl groups, and phenyl, biphenyl, naphthyl, pyridino, thienyl, or furyl groups which may be substituted with at least one group selected from the group consisting of an alkyl group having 1 to 6 carbon atoms, a halogen atom, and phenyl, biphenyl, naphthyl, pyridino, thienyl, and furyl groups; $R_1$ to $R_{28}$ each independently represent a hydrogen atom; a halogen atom; an alkyl group having 1 to 6 carbon atoms which may be substituted with at least one group selected from the group consisting of a halogen atom, phenyl, biphenyl, naphthyl, pyridino, thienyl, and furyl groups;

and a phenyl, biphenyl, naphthyl, pyridino, thienyl, or furyl group which may be substituted with at least one group selected from the group consisting of an alkyl group having 1 to 6 carbon atoms, a halogen atom, and phenyl, biphenyl, naphthyl, pyridino, thienyl, and furyl groups, and the neighboring groups among the substituent groups represented by $R_1$ to $R_{14}$ and $R_{29}$ in Formula (3) and $R_{15}$ to $R_{29}$ in Formula (4) may bind to each other to form a benzene or naphthalene ring).

2. The light-emitting device according to claim 1, wherein $X_1$, $X_2$, $X_3$ and $X_4$ in Formula (3) or (4) each represent an oxygen or sulfur atom.

3. The light-emitting device according to claim 1, wherein the neighboring groups among $R_1$ to $R_4$, $R_8$ to $R_{11}$, $R_{15}$ to $R_{18}$, and $R_{21}$ to $R_{24}$ in Formula (3) or (4) bind to each other, forming a benzene or naphthalene ring.

4. The light-emitting device according to claim 1, wherein $R_1$ and $R_2$ and/or $R_3$ and $R_4$ and/or $R_8$ and $R_9$ and/or $R_{10}$ and $R_{11}$ and/or $R_{15}$ and $R_{16}$ and/or $R_{17}$ and $R_{18}$ and/or $R_{21}$ and $R_{22}$ and/or $R_{23}$ and $R_{24}$ in Formula (3) or (4) bind to each other, forming a benzene or naphthalene ring.

5. The light-emitting device according to claim 1, wherein the substituent groups represented by $R_1$ to $R_{29}$ in Formula (3) or (4) each are an alkyl group having 1 to 6 carbon atoms which may be substituted with at least one group selected from the group consisting of a halogen atom, phenyl, biphenyl, naphthyl, pyridino, thienyl, and furyl groups; or phenyl or naphthyl group which may be substituted with at least one group selected from the group consisting of an alkyl group having 1 to 6 carbon atoms, a halogen atom, and phenyl, biphenyl, naphthyl, pyridino, thienyl, and furyl groups.

6. The light-emitting device according to claim 1, wherein the substituent groups represented by $R_1$ to $R_{28}$ in Formulae (3) and (4) each are a halogen atom; a phenyl or naphthyl group having a halogen atom; or a C1-C6 alkyl group having a halogen atom and the substituent groups represented by $R_{29}$ in Formulae (3) and (4) is a phenyl or naphthyl group having a halogen atom; or a C1-C6 alkyl group having a halogen atom.

7. The light-emitting device according to claim 1, wherein the halogen atom is a bromine or fluorine atom.

8. The light-emitting device according to any one of claims 1 or 2 to 7 wherein the organic thin film has a laminate structure at least containing a positive hole-transporting layer and a light-emitting layer.

9. The light-emitting device according to any one of claims 1 or 2 to 7, wherein an anode, a positive hole-transporting layer, a light-emitting layer, an electron-transporting layer, and a cathode are laminated in that order.

10. The light-emitting device according to any one of claims 1 or 2 to 7, wherein at least a positive hole-injecting layer, a positive hole-transporting layer, and an electron-transporting layer are formed between the anode and the cathode.

11. The light-emitting device according to any one of claims 1 or 2 to 7, wherein the compound represented by Formula (3) or (4) is contained as the host material of the light-emitting material in the light-emitting layer.

12. The light-emitting device according to any one of claims 1 or 2 to 7, wherein the compound represented by Formula (3) or (4) is contained as the dopant for the light-emitting layer.

13. The light-emitting device according to any one of claims 1 or 2 to 7, wherein a white light is emitted by combined use of a blue to green light-emitting material.

14. The light-emitting device according to any one of claims 1 or 2 to 7, wherein one of organic thin films is a positive hole-injecting layer and the positive hole-injecting layer contains a compound represented by the Formula (3) or (4).

15. The light-emitting device according to any one of claims 1 or 2 to 7, wherein the light-emitting device is a device for a display in a matrix mode and/or a segment mode.

16. A condensed polycyclic compound represented by Formula (5):

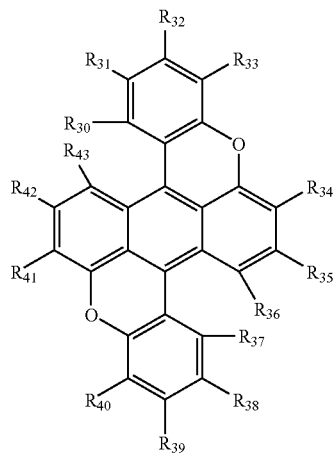

(5)

(wherein, $R_{30}$ to $R_{43}$ each independently represent a hydrogen atom; a halogen atom; an aromatic residue which may be substituted with a halogen atom; at least one of $R_{31}$, $R_{33}$, $R_{38}$ and $R_{40}$ is a phenyl which may be substituted with a halogen atom; and $R_{30}$ and $R_{31}$, and, $R_{37}$ and $R_{38}$, or, $R_{32}$ and $R_{33}$, and, $R_{39}$ and $R_{40}$, may bind to each other forming benzene ring(s), however excluding the case where $R_{30}$ and $R_{31}$ and $R_{37}$ and $R_{38}$, or $R_{32}$ and $R_{33}$ and $R_{39}$ and $R_{40}$, bind to each other forming unsubstituted benzene rings and all of $R_{30}$ to $R_{43}$ that do not form a ring are a hydrogen atom).

17. A condensed polycyclic compound represented by Formula (6):

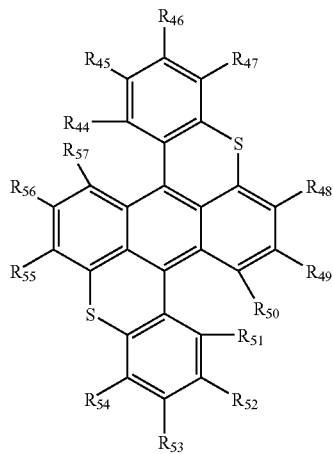

(6)

(wherein, $R_{44}$ to $R_{57}$ each independently represent a hydrogen atom, a halogen atom, a C1-C6 alkyl group, or a phenyl group; at least one of $R_{45}$, $R_{47}$, $R_{52}$, and $R_{54}$ is a C1-C6 alkyl group, or a phenyl group).

18. A condensed polycyclic compound represented by the following General Formula (7):

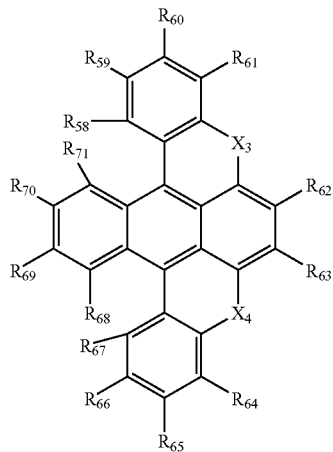

(7)

(wherein, $X_3$ and $X_4$ each independently represent an oxygen, $R_{58}$ to $R_{71}$ each represent a hydrogen atom, or a phenyl; at least one of $R_{59}$, $R_{61}$, $R_{64}$, and $R_{66}$ represents a phenyl group.

* * * * *